US011773077B2

(12) United States Patent
Sharma et al.

(10) Patent No.: US 11,773,077 B2
(45) Date of Patent: *Oct. 3, 2023

(54) COMPOUNDS CONTAINING CARBON-CARBON LINKER AS GPR120 AGONISTS

(71) Applicant: PIRAMAL ENTERPRISES LIMITED, Mumbai (IN)

(72) Inventors: Rajiv Sharma, Fremont, CA (US); Sanjay Kumar, Mumbai (IN); Vishal Mahajan, Thane (IN); Komal Bajaj, Mumbai (IN); Pallavi Godse, Pune (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 262 days.

This patent is subject to a terminal disclaimer.

(21) Appl. No.: 17/087,144

(22) Filed: Nov. 2, 2020

(65) Prior Publication Data

US 2021/0053938 A1 Feb. 25, 2021

Related U.S. Application Data

(62) Division of application No. 15/548,628, filed as application No. PCT/IN2016/000035 on Feb. 2, 2016, now Pat. No. 10,941,133.

(Continued)

(51) Int. Cl.

| | |
|---|---|
| ***C07D 401/10*** | (2006.01) |
| ***A61P 3/00*** | (2006.01) |
| ***A61P 29/00*** | (2006.01) |
| ***A61K 31/192*** | (2006.01) |
| ***C07D 333/24*** | (2006.01) |
| ***C07D 333/60*** | (2006.01) |
| ***C07D 409/10*** | (2006.01) |
| ***C07D 277/60*** | (2006.01) |
| ***C07D 213/64*** | (2006.01) |
| ***C07D 307/79*** | (2006.01) |
| ***C07C 57/62*** | (2006.01) |
| ***A61K 45/06*** | (2006.01) |
| ***A61K 31/381*** | (2006.01) |
| ***A61K 31/428*** | (2006.01) |

(Continued)

(52) U.S. Cl.

CPC .......... *C07D 401/10* (2013.01); *A61K 31/192* (2013.01); *A61K 31/381* (2013.01); *A61K 31/428* (2013.01); *A61K 31/4418* (2013.01); *A61K 45/06* (2013.01); *A61P 3/00* (2018.01); *A61P 29/00* (2018.01); *C07C 57/62* (2013.01); *C07D 213/64* (2013.01); *C07D 277/60* (2013.01); *C07D 277/66* (2013.01); *C07D 307/79* (2013.01); *C07D 333/08* (2013.01); *C07D 333/24* (2013.01); *C07D 333/60* (2013.01); *C07D 339/06* (2013.01); *C07D 409/10* (2013.01); *C07C 2601/04* (2017.05); *C07C 2601/14* (2017.05); *C07C 2601/16* (2017.05); *C07C 2602/06* (2017.05); *C07C 2602/10* (2017.05)

(58) Field of Classification Search

CPC .. C07D 301/10; C07D 213/64; C07D 277/60; C07D 277/66; C07D 307/79; C07D 333/08; C07D 333/24; C07D 333/60; C07D 339/06; C07D 409/10; A61K 31/192; A61K 31/381; A61K 31/428; A61K 31/4418; A61K 45/06; A61P 3/00; A61P 29/00; C07C 57/62; C07C 2601/04; C07C 2601/14; C07C 2601/16; C07C 2602/06; C07C 2602/10

See application file for complete search history.

(56) References Cited

FOREIGN PATENT DOCUMENTS

| | | | |
|---|---|---|---|
| WO | 2012058649 | A1 | 5/2012 |
| WO | 2014069963 | A1 | 5/2014 |

(Continued)

OTHER PUBLICATIONS

Danziger, Automated site-directed drug design: a general algorithm for knowledge acquisition about hydrogen-bonding regions at protein surfaces, Proc. R. Soc. Lond., 1989, 236, pp. 101-113 (Year: 1989).*

(Continued)

*Primary Examiner* — Clinton A Brooks
*Assistant Examiner* — Andrew P Lee
(74) *Attorney, Agent, or Firm* — CARTER, DELUCA & FARRELL LLP

(57) ABSTRACT

The present invention relates to compound of Formula (I)

(I)

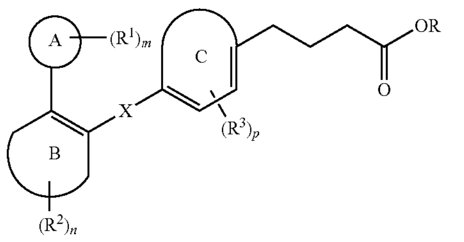

containing carbon-carbon linker, a stereoisomer, a tautomer, a pharmaceutically acceptable salt, a pharmaceutically acceptable solvate, a prodrug, a polymorph, N-oxide, S-oxide, or a carboxylic acid isostere thereof; processes for their preparation; pharmaceutical compositions comprising said compounds; and their use for the treatment of the diseases or disorders mediated by GPR120 receptor.

23 Claims, No Drawings

Related U.S. Application Data

(60) Provisional application No. 62/112,285, filed on Feb. 5, 2015.

(51) Int. Cl.

| | |
|---|---|
| ***A61K 31/4418*** | (2006.01) |
| ***C07D 339/06*** | (2006.01) |
| ***C07D 277/66*** | (2006.01) |
| ***C07D 333/08*** | (2006.01) |

(56) References Cited

FOREIGN PATENT DOCUMENTS

| | | | |
|---|---|---|---|
| WO | 2014209034 | A1 | 12/2014 |
| WO | 2015125085 | A1 | 8/2015 |
| WO | 2016012965 | A2 | 1/2016 |
| WO | 2016038540 | A1 | 3/2016 |

OTHER PUBLICATIONS

Simone, Oncology: Introduction, Textbook of Medicine, 1997, 14, pp. 1004-1010 (Year: 1997).*

International Search Report for International Application No. PCT/IN2016/000035 dated May 5, 2016.

Yu et al., "Physical characterization of polymorphic drugs: an integrated characterization strategy" PSTT, vol. 1 (3), 118-127, 1998.

Braga etal., "Making crystals from crystals: a green route to crystal engineering and polymorphism" J. Royal Soc. Chem. Commun. p. 3635-3645. (Year: 2005).

Bernstein, "Polymorphism in Molecular Crystals" p. 115-118, 272. (Year: 2002).

Davidovich et al., "Detection of Polymorphism by Powder X-Ray Diffraction: Interference by Preferred Orientation" Am. Pharm. Rev. vol. 2 (1) p. 10,12, 14, 16,100. (Year: 2004).

Dean "Analytical Chem Handbook" p. 10.24-10.26. (Year: 1995).

Ivanisevic et al. "Use of X-ray Powder Diffraction In the Pharmaceutical Industry" Pharm. Sci. Encycl. p. 1-42. (Year: 2010).

Seddon "Pseudopolymorph: A Polemic" Crystal Growth & Design v.4(6) 1087 (2 pages from internet) (Year: 2004).

Jain et al., "Polymorphism in Pharmacy", Indian Drugs 23(6) 315-329. (Year: 1986).

Jordan "Tamoxifen: A Most Likely Pioneering Medicine" Nature Rev. v.2, p. 205-213. (Year: 2003).

Kirk-Othmer Encyclopedia of Chemical Technology, 8, pp. 95-147. (Year: 2002).

Vippagunta et al., "Crystalline Solids", Advanced Drug Delivery Reviews 48 3-26. (Year: 2001).

Guillory (in Brittain ed.), "Polymorphism in Pharmaceutical Solids.," NY: Marcel Dekker, Inc., 1-2, 125-181, 183-226. (Year: 1999).

Ettmayer et al., "Lessons Learned from Marketed and Investigational Prodrugs" J. Med. Chem., 47(10): 2393-2404. (Year: 2004).

Stella, "Prodrugs as therapeutics", Expert Opin. Ther. Patents, 14(3): 277-280. (Year: 2004).

Testa, "Prodrug Research: futile or fertile?" Biochemical Pharmacology, 68:2097-2106 (Year: 2004).

Balant, et al., "Metabolic Considerations in Prodrug Design", Burger's Medicinal Chemistry and Drug Discovery, 5th Edition, NY: John Wiley & Sons, 1996, vol. 1, p. 949-976.

Bundgaard, Design of Prodrugs, Chapter 1, p. 1. (Year: 1985).

Silverman, Prodrugs and Drug Delivery Systems, The Organic Chemistry of Drug Design and Drug Action, Chapter 8, pp. 352-400. (Year: 1992).

Banker et al., "Prodrugs, Modern Pharmaceutics", 3rd edition, Revised and Expanded, pp. 451 and 596. (Year: 1986).

* cited by examiner

COMPOUNDS CONTAINING CARBON-CARBON LINKER AS GPR120 AGONISTS

CROSS REFERENCE TO RELATED APPLICATIONS

This application is a divisional of U.S. patent application Ser. No. 15/548,628, filed Aug. 3, 2017, which is a national stage application of International Application No. PCT/IN2016/000035, filed Feb. 2, 2016, which claims the benefit and priority of U.S. Patent Application No. 62/112,285, filed Feb. 5, 2015, the entire contents of each of which are hereby incorporated by reference herein in their entirety.

FIELD OF THE INVENTION

The present invention relates to compounds containing carbon-carbon linker represented by the compounds of Formula (I) (as described herein); processes for their preparation; pharmaceutical compositions comprising said compounds; and methods of using said compounds for the treatment or prophylaxis of the diseases or disorders mediated by GPR120 receptor.

BACKGROUND OF THE INVENTION

Metabolic diseases or disorders are caused by an abnormal metabolic process and may either be congenital due to an inherited enzyme abnormality, or acquired due to a disease of an endocrine organ or failure of a metabolically important organ such as the liver or the pancreas.

Among the metabolic disorders, diabetes mellitus is the most prevalent and is considered to be one of the five leading causes of death in the world (*Diabetes Care*, vol. 27, 2004, pp. 1047-1053). Diabetes mellitus is typically classified into two main subtypes: Type 1 and Type 2 diabetes mellitus. Type 1 diabetes mellitus (otherwise known as Insulin Dependent Diabetes Mellitus, IDDM), which generally occurs in adolescents under 20 years of age, is an auto-immune disease causing an insulitis with the subsequent destruction of insulin-producing β-cells of the pancreas. Further, in latent autoimmune diabetes in adults (LADA), β-cells are destroyed due to autoimmune attack. The subsequent lack of insulin leads to elevated levels of blood and urine glucose (hyperglycemia). Although the exact trigger for this autoimmune response is not known, patients with Type 1 diabetes have high levels of antibodies against pancreatic beta cells (hereinafter "beta cells"). However, it cannot be ascertained that all patients with high levels of these antibodies develop Type 1 diabetes. Type 2 diabetes mellitus or non-insulin-dependent diabetes mellitus (NIDDM) is developed when human muscles, fat and liver cells are not able to respond normally to insulin that body secretes. This inability to respond, otherwise known as insulin resistance, may be due to restriction on the numbers of insulin receptors on these cells, or a dysfunctional behaviour of signalling pathways within the cells, or both. Initially, the β-cells which are responsible for the production of insulin, compensate for this insulin resistance by increasing their insulin secretion. However, gradually these cells become unable to produce enough insulin to facilitate the normal glucose homeostasis, causing the progression to Type 2 diabetes (*Am J Med.* 108(6), *Supplement* 1, 2000, pp. 25-8). Type 2 diabetes (T2D) is characterised by fasting hyperglycemia which occurs as an effect of the combined lesions of insulin resistance and β-cell dysfunction. There are two types of defects associated with the β-cells: the first component, an increase in the basal insulin release which usually occurs in the presence of low, non-stimulatory glucose concentrations. The second component is a failure to enhance the insulin release in response to a hyperglycaemic challenge.

Obesity is another risk factor for developing metabolic diseases or disorders such as diabetes, cardiovascular disorders, hypertension, hyperlipidemia and an increased mortality. Diabetes caused by insulin resistance and obesity are part of the "metabolic syndrome" which is defined as the linkage between several diseases (also referred to as syndrome X, insulin-resistance syndrome, or deadly quartet). These often occur in the same patients and are major risk factors for the development of Type 2 diabetes and cardiovascular diseases (Frontiers in Endocrinology, vol. 4, 2013, pp. 1-11). It has been suggested that the control of lipid levels and/or glucose levels is required to treat type 2 diabetes and cardiovascular diseases. Even though lifestyle changes like exercise and healthy diet are regarded as the most efficient ways to prevent and manage the disease, pharmaceutical intervention is frequently necessary.

Current treatment options for diabetes, particularly T2D include use of hypoglycaemic agents and insulin. Metformin is one such hypoglycaemic agent, which is used in the treatment of Type 2 diabetes. It is, in fact, one of the oldest drugs used for the treatment of T2D and it continues to remain the drug of choice despite associated gastrointestinal (GI) side effects including anorexia, nausea, diarrhoea and vomiting commonly associated with it. In fact, metformin should be used with caution in patients with renal impairment because of the slight risk of lactic acidosis. Sulfonylureas (SUs) e.g. glimepiride, glipizide, are insulin secretagogues, which act on β-cells to increase insulin release, are commonly used in the treatment of Type 2 diabetes. However, use of sulfonylureas is also associated with adverse effects in that they increase the risk of hypoglycaemia and lead to weight gain. Insulin treatment also carries the same side-effects. Thiazolidinedione compounds e.g. rosiglitazone, pioglitazone, are insulin sensitizers which bind to peroxisome proliferator-activated receptors (PPARs) in cells and thereby increase the insulin sensitivity. Though, thiazolidinedione compounds have also been widely used, the enhanced risks of cardiovascular disease and hepatotoxicity have resulted in stringent limitations on their use. Relatively recently, regulatory authorities approved new classes of anti-diabetic agents such as GLP-1 agonists (exenatide and liraglutide) and DPP-4 inhibitors (linagliptin and alogliptin).

It is a known fact that metabolic processes are regulated by fatty acids which are important biological molecules that serve both as a source of energy and as signalling molecules. Generally, it is believed that fatty acids produce their biological effects through interacting with intracellular targets including, for example, the family of peroxisome proliferator-activated receptors (PPARs). However, in the recent years it has become clear that fatty acids also serve as agonists for a group of cell surface G protein-coupled receptors (GPCRs). Free fatty acids (FFAs) have been demonstrated to act as ligands of several GPCRs including GPR40 (FFAR1), GPR43, GPR84, GPR119 and GPR120. One of the GPCR namely GPR40 facilitates glucose-stimulated insulin secretion from pancreatic β-cells, whereas the other GPCR namely GPR120 regulates the secretion of glucagon-like peptide-1 (GLP-1) in the intestine, as well as insulin sensitivity in macrophages. GPR120 is localized to intestinal enteroendocrine cells, such as colonic L cells. Certain research studies conducted relative recently, identified that loss-of-function GPR120 human variant is associated with obesity, diabetes and other insulin resistance, and related metabolic disorders, and also with inflammatory disorders. These findings establish GPR120 as a potential target for the treatment of diabetes, other metabolic disorders, and inflammatory disorders as well (*Trends Pharmacol Sci. vol.* 32(9), 2011 pp. 543-550).

Various patent documents describe compounds which are reported to be GPR120 modulators. Examples of patent documents describing GPR120 modulators include PCT Application Publications WO2008103500, WO2009038204, WO2010008831, WO2010048207, WO2010080537, WO2010104195, WO2011072132, WO2013139341 and WO2013185766; European Published Patent Application EP2125758A1; US Published Patent Application US2011065739 and U.S. Pat. No. 8,367,708.

Thus, in view of the role of GPR120 receptor in potentiating metabolic disorders such as diabetes and related disorders, and also, inflammatory disorders, there is a continuing need to develop compounds that act by modulating the GPR120 receptor pathways.

SUMMARY OF THE INVENTION

In one aspect, the present invention relates to a compound of Formula (I) (as described herein), or a stereoisomer, a tautomer, a pharmaceutically acceptable salt, a pharmaceutically acceptable solvate, a prodrug, a polymorph, N-oxide, S-oxide, or a carboxylic acid isostere thereof.

In another aspect, the present invention relates to a process for the preparation of the compound of Formula (I) or a pharmaceutically acceptable salt thereof.

In a further aspect, the present invention relates to a pharmaceutical composition comprising a therapeutically effective amount of a compound of Formula (I) or a stereoisomer, a tautomer, a pharmaceutically acceptable salt, or a pharmaceutically acceptable solvate thereof; and at least one pharmaceutically acceptable carrier or excipient.

In a further aspect, the present invention relates to a pharmaceutical composition comprising a therapeutically effective amount of a compound of Formula (I) or a stereoisomer, a tautomer, a pharmaceutically acceptable salt, or a pharmaceutically acceptable solvate thereof; and one further therapeutically active agent and at least one pharmaceutically acceptable carrier or excipient.

In an aspect, the present invention relates to the compound of Formula (I) or a tautomer, a stereoisomer, a pharmaceutically acceptable salt or a pharmaceutically acceptable solvate thereof; for use as GPR120 agonist.

In another further aspect, the present invention relates to a method for modulating GPR120 function in a cell, comprising contacting a cell with an effective amount of a compound of Formula (I) or a stereoisomer, a tautomer or a pharmaceutically acceptable salt, or a pharmaceutically acceptable solvate thereof.

In yet another further aspect, the present invention relates to a method for the treatment or prophylaxis of a disease or a disorder mediated by GPR120, comprising administering to a subject in need thereof; a therapeutically effective amount of the compound of Formula (I) or a stereoisomer, a tautomer, a pharmaceutically acceptable salt, or a pharmaceutically acceptable solvate thereof.

In yet another aspect, the present invention relates to a compound of Formula (I) or a stereoisomer, a tautomer, a pharmaceutically acceptable salt, or a pharmaceutically acceptable solvate thereof; for use in the treatment or prophylaxis of a disease or a disorder mediated by GPR120.

In a still further aspect, the present invention relates to use of the compound of Formula (I) or a stereoisomer, a tautomer, a pharmaceutically acceptable salt or a pharmaceutically acceptable solvate thereof; in the manufacture of a medicament, for the treatment or prophylaxis of a disease or a disorder mediated by GPR120.

In another further aspect, the present invention relates to use of the compound of Formula (I) or a stereoisomer, a tautomer, or a pharmaceutically acceptable salt or a pharmaceutically acceptable solvate thereof; in combination with one further therapeutically active agent for the treatment or prophylaxis of a disease or a disorder mediated by GPR120.

These and other objectives and advantages of the present invention will be apparent to those skilled in the art from the following description.

DETAILED DESCRIPTION OF THE INVENTION

It should be understood that the detailed description and specific examples, while indicating embodiments of the invention, are given by way of illustration only, since various changes and modifications within the spirit and scope of the invention will become apparent to those skilled in the art.

One skilled in the art, based upon the definitions herein, may utilize the present invention to its fullest extent. The following specific embodiments are to be construed as merely illustrative, and not limitative of the remainder of the disclosure in any way whatsoever.

Except as defined herein, all the technical and scientific terms used herein have the same meaning as commonly understood by one of ordinary skill in the art to which the invention relates.

Definitions

For the purpose of the disclosure, listed below are definitions of various terms used to describe the present invention. Unless otherwise indicated, these definitions apply to the terms as they are used throughout the specification and the appended claims, either individually or as part of a larger group. These definitions should not be interpreted in the literal sense as they are not general definitions, and are relevant only for this application.

The singular forms "a", "an" and "the" include plural aspects unless the context clearly dictates otherwise. For instance, the terms "a", "an" and "the" refers to "one or more" when used in the subject specification, including the claims. Thus, for example, reference to "a compound" may include a plurality of such compounds, or reference to "a disease" or "a disorder" includes a plurality of diseases or disorders.

Also, use of "(s)" as part of a term, includes reference to the term singly or in plurality, for example the term salt(s) indicates a single salt or more than one salt of the compound of formula (I).

The term "or" is generally employed in its sense including "and/or" unless the content clearly dictates otherwise.

A symbol (—) is used to indicate a point of attachment to the atom, for example —COOH is attached through the carbon atom.

Unless indicated otherwise, the term "optionally substituted" when used means "substituted or unsubstituted," and therefore, the generic structural formulae described herein encompasses compounds containing the specified optional substituent as well as compounds that do not contain the optional substituent. For example, the phrase "heteroaryl is optionally substituted with one or more groups" encompasses unsubstituted heteroaryl ring, and heteroaryl ring substituted with one or more groups as described.

Within the context of the present application and as used herein, the term "unsaturated" means that a moiety has one or more units of unsaturation.

Within the context of the present application and as used herein, the term "partially unsaturated" refers to a ring moiety that includes at least one double bond between ring atoms but is not aromatic.

The term "independently" when used in the context of selection of substituents for a variable, it means that where more than one substituent is selected from a number of possible substituents, those substituents can be the same or different.

As used herein, the term "halogen" refers to chlorine, fluorine, bromine or iodine atom.

As used herein, the term "($C_1$-$C_6$)alkyl" or "alkyl" alone or as part of a substituent group, refers to the radical of saturated aliphatic groups, including straight or branched-chain alkyl groups. A straight-chain or branched chain alkyl has six or fewer carbon atoms in its backbone, for instance, $C_1$-$C_6$ for straight chain and $C_3$-$C_6$ for branched chain. As used herein, ($C_1$-$C_6$)alkyl refers to an alkyl group having from 1 to 6 carbon atoms. Representative examples of alkyl include, but are not limited to, methyl, ethyl, n-propyl, n-butyl, n-pentyl, n-hexyl, isopropyl, sec-butyl, isobutyl, tert-butyl, isopentyl, 2-methylbutyl and 3-methylbutyl. In the "($C_1$-$C_6$)alkyl" group, one or more carbon atoms can be optionally replaced with one or more heteroatoms independently selected from the group consisting of N, O and S.

Furthermore, unless stated otherwise, the alkyl group can be unsubstituted or substituted with one or more groups, for example, from one to four groups, independently selected from the group consisting of ($C_1$-$C_6$)alkyl, ($C_1$-$C_6$)alkenyl, halogen, halo($C_1$-$C_6$)alkyl, hydroxy, ($C_1$-$C_6$)alkoxy, halo ($C_1$-$C_6$)alkoxy, ($C_3$-$C_{10}$)cycloalkyl, ($C_6$-$C_{10}$)aryl, ($C_6$-$C_{10}$) aryloxy, heterocyclyl, heteroaryl, amino, cyano, nitro, —NH ($C_1$-$C_6$)alkyl, —N[($C_1$-$C_6$)alkyl]$_2$, —C(O)($C_1$-$C_6$)alkyl, —C(O)O($C_1$-$C_6$)alkyl, —C(O)$NH_2$, —C(O)NH($C_1$-$C_6$)alkyl, —C(O)N[($C_1$-$C_6$)alkyl]2 and —C(O)$NHSO_2$($C_1$-$C_6$) alkyl.

Examples of substituted alkyl include, but are not limited to, hydroxymethyl, 2-chlorobutyl, trifluoromethyl, aminoethyl or benzyl.

As used herein, the term "halo($C_1$-$C_6$)alkyl" or "haloalkyl" refers to alkyl groups as defined above wherein one or more hydrogen atom of same or different carbon atoms of the alkyl group are substituted with same or different halogens. A monohalo($C_1$-$C_6$)alkyl radical, for example, can have a chlorine, bromine, iodine or fluorine atom. Dihalo or polyhalo($C_1$-$C_6$)alkyl radicals can have two or more of the same or different halogen atoms. Representative examples of halo($C_1$-$C_6$)alkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl or difluoropropyl.

As used herein, the term "($C_1$-$C_6$)alkoxy" or "alkoxy" refers to a ($C_1$-$C_6$)alkyl having an oxygen radical attached thereto. The terms "($C_1$-$C_6$)alkoxy" or "—O($C_1$-$C_6$)-alkyl" or alkoxy wherever used in this specification have the same meaning. Representative examples of alkoxy groups include, but are not limited to, methoxy, ethoxy, propoxy, isopropoxy, n-butoxy, isobutoxy and tert-butoxy. Furthermore, unless stated otherwise, the alkoxy groups can be unsubstituted or substituted with one or more groups. A substituted alkoxy refers to a ($C_1$-$C_6$)alkoxy substituted with one or more groups, particularly one to four groups independently selected from the groups indicated above as the substituents for the alkyl group.

As used herein, the term ($C_3$-$C_{10}$)cycloalkyl" or "cycloalkyl" whether used alone or as part of a substituent group, refers to a saturated or partially unsaturated cyclic hydrocarbon radical including 1, 2 or 3 rings and including a total of 3 to 10 carbon atoms; preferably 3 to 8 carbon atoms forming the rings i.e. ($C_3$-$C_{10}$)cycloalkyl or ($C_3$-$C_8$)cycloalkyl group. The term cycloalkyl includes bridged, fused and spiro ring systems. For example, ($C_3$-$C_{10}$)cycloalkyl refers to a cycloalkyl group having 3 to 10 (both inclusive) carbon atoms. Representative examples of cycloalkyl include, but are not limited to, cyclobutyl, cyclopentyl, cyclohexyl, 1,2,3,3a-tetrahydropentalene, adamantyl, norbornyl, tetrahydronaphthalene, bicyclo[2.1.0]pentane, bicyclo[4.2.0]octane, bicyclo[2.2.1]heptyl, bicyclo[2.2.1]hept-2-ene, spiro[3.3]heptane, and the like. Unless stated otherwise, ($C_4$—C)cycloalkyl may be unsubstituted or substituted with one or more groups independently selected from the group consisting of ($C_1$-$C_6$)alkyl, halogen, halo($C_1$-$C_6$)alkyl, hydroxy, —O($C_1$-$C_6$)alkyl, halo($C_1$-$C_6$)alkoxy, ($C_3$-$C_{10}$)cycloalkyl, ($C_6$-$C_{10}$)aryl, heterocyclyl, heteroaryl, amino and cyano.

The term "($C_6$-$C_{10}$)aryl" or "aryl" as used herein refers to a monocyclic or bicyclic hydrocarbon groups having 6 to 10 ring carbon atoms, wherein at least one carbocyclic ring is having a 7 electron system. Examples of ($C_6$-$C_{10}$)aryl ring include, but are not limited to, phenyl or naphthyl. Unless indicated otherwise, aryl group may be unsubstituted or substituted with one or more groups. A substituted aryl refers to a ($C_6$-$C_{10}$)aryl substituted with one or more groups, preferably 1 to 7 groups, and more preferably 1 to 3 groups independently selected from the group consisting of ($C_1$-$C_6$)alkyl, ($C_2$-$C_5$)alkenyl, ($C_2$-$C_5$)alkynyl, halogen, halo($C_1$-$C_6$)alkyl, hydroxy, —O—($C_1$-$C_6$)alkyl, halo($C_1$-$C_6$)alkoxy, ($C_3$-$C_{10}$)cycloalkyl, ($C_6$-$C_{10}$)aryl, heterocyclyl, heteroaryl, amino and cyano. Aryl groups can be substituted in any desired position. For example, in monosubstituted aryl such as phenyl, the substituent can be located in the 2-position, the 3-position, the 4-position or the 5-position. If the phenyl carries two substituents, they can be located in 2,3-position, 2,4-position, 2,5-position, 2,6-position, 3,4-position or 3,5-position. Examples of monosubstituted phenyl groups include, but are not limited to, 2-fluorophenyl, 2-ethoxyphenyl, 2-ethylphenyl, 4-morpholinophenyl, (4-ethylpiperazin-1-yl)phenyl or 4-(2-dimethylaminoethyl)phenyl. Examples of disubstituted phenyl groups include, but are not limited to, 2,6-difluorophenyl or 3,5-difluorophenyl.

As used herein, the term "heteroaryl", whether used alone or as part of a substituent group, refers to saturated or partially unsaturated 5- to 12-membered, preferably 5- to 10-membered monocyclic or bicyclic aromatic ring system containing 1, 2, 3 or 4 heteroatoms independently selected from the group consisting of oxygen, nitrogen and sulfur atom. Representative examples of heteroaryls include, but are not limited to, furan, pyrrole, thiophene, imidazole, oxazole, thiazole, triazole, tetrazole, benzofuran, indole, benzoxazole, benzothiazole, isoxazole, triazine, purine, pyridine, pyrazine, quinoline, isoquinoline, phenazine, oxadiazole, pteridine, pyridazine, quinazolinyl, pyrimidine, isothiazole, quinoxaline (benzopyrazine), tetrazole, pyrido[2,3-b]pyrazine. The oxidized form of the ring nitrogen and sulfur atom contained in the heteroaryl to provide the corresponding N-oxide, S-oxide or S,S-dioxide is also encompassed in the scope of the present invention.

Furthermore, the heteroaryl groups can be unsubstituted or substituted with one or more groups; preferably 1 to 7 groups, more preferably 1 to 3 groups independently selected from the group consisting of halogen, hydroxy, $(C_1-C_6)$alkyl, halo$(C_1-C_6)$alkyl, $(C_1-C_6)$alkoxy, halo$(C_1-C_6)$ alkoxy, $(C_3-C_{10})$cycloalkyl, $(C_6-C_{10})$aryl, heterocyclyl, heteroaryl, amino, cyano and oxo. The representative examples of heteroaryl include, but are not limited to, pyrrole, pyrazole, imidazole, isothiazole, pyrazine, furan, thiophene, triazole, benzothiazole, benzofuran, indole, purine, pyridine, quinoline, isoquinoline, pyridazine, quinazolinyl, pyrimidine and azocine.

The term "heteroatom" as used herein, includes nitrogen (N), oxygen (O) and sulfur (S). Any heteroatom with unsatisfied valency is assumed to have a hydrogen atom to satisfy the valency or when the heteroatom is N, it may be substituted with a group selected from $(C_1-C_6)$alkyl, —C(O)$(C_1-C_6)$alkyl, —C(O)O$(C_1-C_6)$alkyl or —$S(O)_2(C_1-C_6)$alkyl. Suitable $(C_1-C_6)$alkyl groups include, but are not limited to, methyl, ethyl, propyl, butyl, pentyl, hexyl, isopropyl or isobutyl.

As used herein, the term "heterocycloalkyl" refers to saturated or partially unsaturated 5- to 12 membered, preferably 5- to 10-membered monocyclic or bicyclic ring containing at least one heteroatom, preferably, 1, 2, 3 or 4 heteroatoms independently selected from the group consisting of nitrogen, oxygen, and sulfur. The representative examples of heterocyclyl include, but are not limited to, tetrahydropyranyl, piperidinyl, piperidino, N-methylpiperidin-3-yl, piperazinyl, N-methylpyrrolidin-3-yl, 3-pyrrolidinyl, 2-pyrrolidon-1-yl, pyrrolidinyl, aziridinyl, pyrrolidino, piperazino, morpholinyl, morpholino, thiomorpholinyl, thiomorpholino, tetrahydrofuranyl, tetrahydrothiofuranyl, and pyranyl.

Furthermore, the heterocycloalkyl groups can be unsubstituted or substituted with one or more groups; preferably 1 to 7 groups, more preferably 1 to 3 groups independently selected from the group consisting of halogen, hydroxy, $(C_1-C_6)$alkyl, halo$(C_1-C_6)$alkyl, $(C_1-C_6)$alkoxy, halo$(C_1-C_6)$ alkoxy, $(C_3-C_{10})$cycloalkyl, $(C_6-C_{10})$aryl, heterocyclyl, heteroaryl, amino, cyano and oxo As used herein, the term "isotopic forms" or "isotopically labeled forms" is a general term used for isotopic forms of the compounds of Formula (I), wherein one or more atoms of the compounds of Formula (I) are replaced by their respective isotopes. All isotopes of any particular atom or element as specified are contemplated within the scope of the compounds of the invention. Examples of isotopes that can be incorporated into the compounds disclosed herein include, but are not limited to, isotopes of hydrogen such as $^2H$ (deuterium or D) and $^3H$, carbon such as $^{11}C$, $^{13}C$ and $^{14}C$, nitrogen such as $^{13}N$ and $^{15}N$, oxygen such as $^{15}O$, $^{17}$ and $^{18}O$, chlorine such as $^{36}Cl$, fluorine such as $^{18}F$ and sulfur such as $^{35}S$. Substitution with heavier isotopes, for example, replacing one or more key carbon-hydrogen bonds with carbon-deuterium bond may show certain therapeutic advantages, resulting from longer metabolism cycles, (e.g., increased in vivo half life or reduced dosage requirements), improved safety or greater effectiveness and hence, may be preferred in certain circumstances.

In the context of the present invention, the term "the compounds of the present invention" or "the compounds encompassed in the present invention" are used interchangeably; and refer to the compounds of Formula (I) and/or the compounds of Formula (IA) and/or the compounds of Formula (IB) and/or the compounds of Formula (IC) as described herein, and encompass within its/their scope a stereoisomer, a tautomer, a pharmaceutically acceptable salt, a pharmaceutically acceptable solvate, a prodrug, a polymorph or an N-oxide thereof. The compound(s) of the present invention can also be referred to herein as "the active compound" or "the active ingredient".

Within the context of the present invention and as used herein, the term "stereoisomer" is a general term used for all isomers of individual compounds that differ only in the orientation of their atoms in space. The term stereoisomer includes mirror image isomers (enantiomers), mixtures of mirror image isomers (racemates, racemic mixtures), geometric (cis/trans, syn/anti or E/Z) isomers, and isomers of compounds with more than one chiral center that are not mirror images of one another (diastereoisomers).

As used herein, the term "tautomer" refers to the coexistence of two or more compounds that differ from each other only in the position of one (or more) mobile atoms and in electron distribution. For example, proton tautomers (also known as prototropic tautomers) include interconversions via migration of a proton, such as keto-enol and imine-enamine tautomers.

Within the context of the present invention and as used herein, the term "pharmaceutically acceptable" means that the carrier, diluent, excipients, and/or salt must be compatible with the other ingredients of the formulation or composition, and not deleterious to the recipient thereof.

The term "pharmaceutically acceptable salt(s)" as used herein includes a salt or salts of the active compounds i.e. the compounds of Formula (I) and are prepared with suitable acids or bases, depending on the particular substituents found on the compounds described herein.

As used herein, the term "pharmaceutically acceptable solvate" or "solvate(s)" describe a complex wherein the compound of Formula (I) of the present invention, is coordinated with a proportional amount of a solvent molecule. Specific solvates, wherein the solvent is water, are referred to as hydrates.

As used herein, the term "prodrug" refers to a compound that is drug precursor, which, when administered to a subject undergoes transformation through metabolic process or chemical transformation in vivo to form an active compound, for example, a prodrug after being brought to the physiological pH or through enzyme action is converted to active compounds, that is, compound of Formula (I) of the present invention. In context of the present invention prodrugs can be esters of the compound of Formula (I), which on metabolism can form an active compound of Formula (I).

As used herein, the term "polymorph" or "polymorphic form" or "polymorphs" refers to crystals of the same compound that differs only in the arrangement and/or conformation of the molecule in the crystal lattice.

As used herein, the term "N-oxide" refers to the oxide of the nitrogen atom of a nitrogen-containing heteroaryl or heterocycloalkyl. N-oxide can be formed in the presence of an oxidizing agent for example peroxide such as m-chloro-perbenzoic acid or hydrogen peroxide. N-oxide refers to an amine oxide, also known as amine-N-oxide, and is a chemical compound that contains N→O bond.

As used herein, the term "S-oxide" refers to an oxide of the sulfur atom (S-oxide) or a dioxide of the sulfur atom (S,S-dioxide) of a sulfur-containing heteroaryl or heterocycloalkyl. S-oxide and S,S-dioxides can be formed in the presence of an oxidizing agent, for example, a peroxide such as m-chloro-perbenzoic acid or oxone.

As used herein, the term "carboxylic acid isostere" refers to a functional group or a moiety that elicits similar physical, biological and/or chemical properties as a carboxylic acid moiety. Representative examples of carboxylic acid isostere include, but are not limited to:

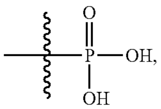 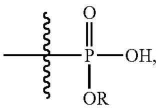

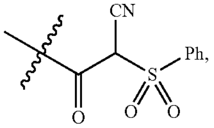 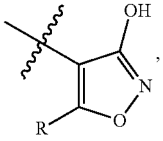

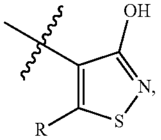 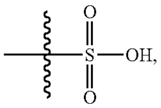 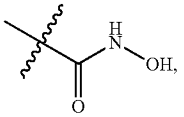

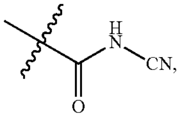 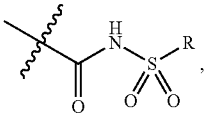

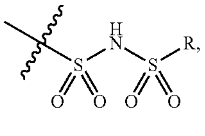 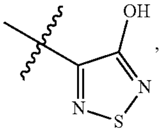

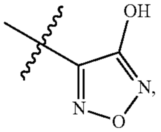 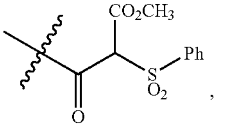

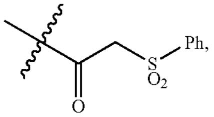 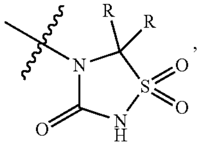

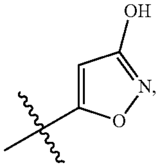 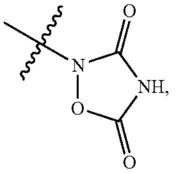 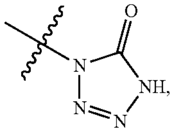

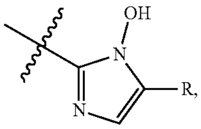 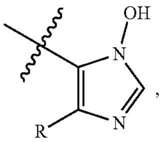

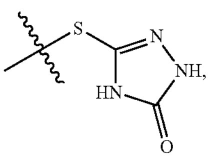 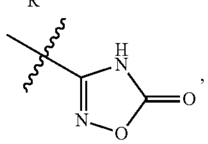

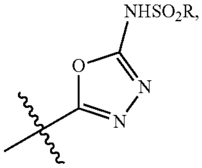 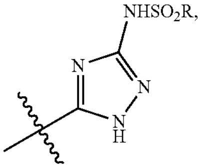

-continued

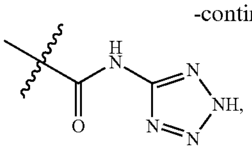 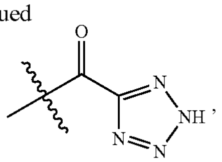

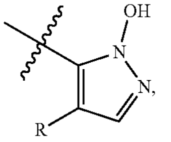 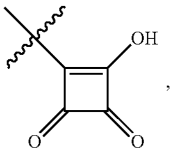

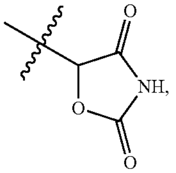 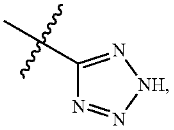

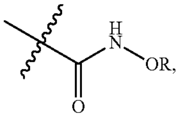 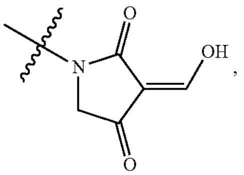

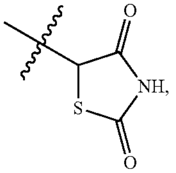 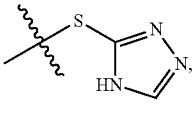

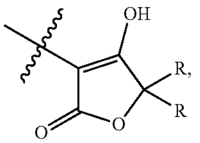 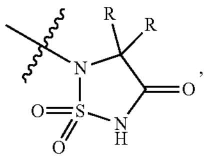

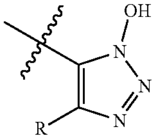 and 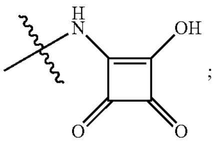

wherein R is hydrogen or ($C_1$-$C_3$)alkyl.

The term "pharmaceutically acceptable carrier" as used herein means a nontoxic, inert, solid, semi-solid, diluent, encapsulating material or formulation auxiliary of any type. A few examples of materials, which can serve as pharmaceutically acceptable carriers include, sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be used in the composition, according to the judgment of the formulator.

As used herein, the term "a disease or a disorder mediated by GPR120" or "GPR120 mediated disease(s) or disorder(s)" refers to a disease or a disorder or a condition characterized by inappropriate, for example, less than or greater than normal GPR120 activity. A GPR120-mediated disease or disorder may be completely or partially mediated by inappropriate GPR120 activity.

The term "metabolic disorder" as used herein refers to a disorder relating to abnormality of metabolism. Accordingly, in the context of the present invention all the disorders relating to abnormality of metabolism are encompassed in the term "metabolic disorders".

The term "metabolic syndrome" refers to a cluster of metabolic abnormalities including abdominal obesity, insulin resistance, glucose intolerance, diabetes, hypertension and dyslipidemia. These abnormalities are known to be associated with an increased risk of vascular events.

The term "diabetes mellitus" or "diabetes" refers to a chronic disease or condition, which occurs when the pancreas does not produce enough insulin, or when the body cannot effectively use the insulin it produces. This leads to an increased concentration of glucose in the blood (hyperglycaemia). Two major forms of diabetes are Type 1 diabetes (Insulin-dependent diabetes mellitus) and Type 2 diabetes (Non-insulin dependent diabetes mellitus (NIDDM)). Type 1 diabetes is an autoimmune condition in which the insulin-producing β-cells of the pancreas are destroyed which generally results in an absolute deficiency of insulin, the hormone that regulates glucose utilization. Type 2 diabetes often occurs in the face of normal or even elevated levels of insulin and can result from the inability of tissues to respond appropriately to insulin. Other categories of diabetes include gestational diabetes (a state of hyperglycemia which develops during pregnancy) and "other" rarer causes (genetic syndromes, acquired processes such as pancreatitis, diseases such as cystic fibrosis, exposure to certain drugs, viruses, and unknown causes).

The term "subject" as used herein refers to an animal, preferably a mammal, and most preferably a human. The term "mammal" used herein refers to warm-blooded vertebrate animals of the class 'mammalia', including humans, characterized by a covering of hair on the skin and, in the female, milk-producing mammary glands for nourishing the young. The term mammal includes animals such as cat, dog, rabbit, bear, fox, wolf, monkey, deer, mouse, pig and human. In the context of the present invention, the phrase "a subject in need thereof" means a subject (patient) in need of the treatment for the disease or disorder that is mediated by GPR120. Alternatively, the phrase "a subject in need thereof" means a subject (patient) diagnosed having a disease or a disorder that is mediated by GPR120.

As used herein, the terms "treatment", "treat", "treating" and "therapy" and the like refer to alleviate, slow the progression, attenuation, or cure of existing diseases or condition (e.g. diabetes). Treatment also includes curing, preventing development of or alleviating to some extent, one or more of the symptoms of the diseases or condition.

As used herein, the term "prophylaxis", used interchangeably with the terms "prevention" or "preventing" means preventing or reducing the probability of the occurrence of a clinical disease-state. Subjects are selected for preventative therapy based on factors that are known to increase risk of suffering a clinical disease state or a condition compared to the general population. "Prophylaxis" therapies can be divided into (a) primary prevention and (b) secondary prevention. Primary prevention is defined as treatment in a subject that has not yet presented with a clinical disease state or a condition, whereas secondary prevention is defined as preventing a second occurrence of the same or similar clinical disease state.

The term "compound(s) for use" as used herein embrace any one or more of the following: (1) use of compound(s), (2) method of use of compound(s), (3) use in the treatment of, (4) the use for the manufacture of pharmaceutical composition/medicament for treatment/treating or (5) method of treatment/treating/preventing/reducing/inhibiting comprising administering an effective amount of the compound of the present invention to a subject in need thereof.

As used herein, the term, "therapeutically effective amount" refers to an amount of a compound of Formula (I) or a pharmaceutically acceptable salt thereof or a composition comprising a compound of Formula (I) or a salt thereof, effective in producing the desired therapeutic response in a subject suffering from a disease or disorder mediated by GPR120. An example of a disease or disorder mediated by GPR120 is diabetes such as type 2 diabetes. Particularly, the term "therapeutically effective amount" includes the amount of a compound (in the context of the present invention, the compound of Formula (I) or a pharmaceutically acceptable salt thereof), when administered that induces a positive modification in the disease or disorder to be treated or is sufficient to prevent development of, or alleviate to some extent one or more of the symptoms of the disease or disorder being treated in a subject. In respect of the therapeutic amount of the compound, consideration is also given that the amount of the compound used for the treatment of a subject is low enough to avoid undue or severe side effects, within the scope of sound medical judgment. The therapeutically effective amount of the compound or composition will vary with the particular condition (in the context of the present invention, the disease or disorder that is mediated by GPR120) being treated, the age and physical condition of the subject, the severity of the condition being treated or prevented, the duration of the treatment, the nature of concurrent therapy, the specific compound or composition employed, the particular pharmaceutically acceptable carrier utilized and other related factors.

As used herein, the term "GPR120 agonist(s)" refers to the compound(s) of Formula (I) of the present invention or a tautomer, a stereoisomer, a pharmaceutically acceptable salt, a pharmaceutically acceptable solvate, a prodrug, a polymorph, an N-oxide, a S-oxide or a carboxylic acid isostere thereof; which binds to, activates, increases, stimulates, potentiates, sensitizes or upregulates GPR120 receptor and promotes insulin sensitization.

In one aspect, the present invention relates to a compound of Formula (I),

Formula (I)

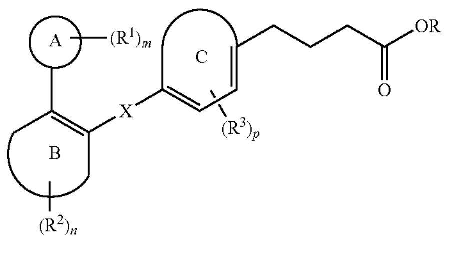

(I)

wherein,

Ring A is 3- to 10-membered cycloalkyl, 5- to 12-membered heterocycloalkyl; $(C_6-C_{10})$aryl or 5- to 12-membered heteroaryl; wherein the heterocycloalkyl and the heteroaryl contain 1, 2, 3 or 4 heteroatoms independently selected from the group consisting of N, O and S;

Ring B and Ring C are independently selected from $(C_6-C_{10})$aryl or 5- to 12-membered heteroaryl containing 1, 2 or 3 heteroatoms independently selected from the group consisting of N, O and S;

X is

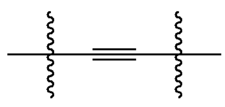,
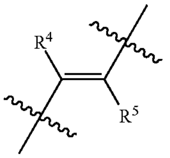
or
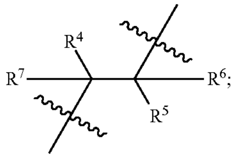

wherein ⌇ represents a point of attachment;

R is hydrogen or $(C_1\text{-}C_6)$alkyl;

$R^1$, $R^2$ and $R^3$ at each occurrence are independently selected from the group consisting of hydrogen, halogen, $(C_1\text{-}C_6)$alkyl, halo$(C_1\text{-}C_6)$alkyl, 3- to 10-membered cycloalkyl and 5- to 12-membered heterocycloalkyl; or two $R^1$ are combined together with Ring A to form a 3- to 6-membered cycloalkyl or 5- to 12-membered heterocycloalkyl;

$R^4$ and $R^7$ are independently selected from the group consisting of hydrogen and $(C_1\text{-}C_6)$alkyl;

$R^5$ and $R^6$ are independently selected from the group consisting of hydrogen, halogen and $(C_1\text{-}C_6)$alkyl;

m, n and p are each integer independently selected from 1, 2 and 3;

wherein, $(C_1\text{-}C_6)$alkyl is unsubstituted or substituted with one or more groups independently selected from the group consisting of halogen, hydroxy, cyano, nitro, $(C_1\text{-}C_6)$alkyl, halo$(C_1\text{-}C_6)$alkyl, —O$(C_1\text{-}C_6)$alkyl, $(C_3\text{-}C_8)$cycloalkyl, $(C_6\text{-}C_{10})$aryl, heterocycloalkyl and heteroaryl;

cycloalkyl is a 3- to 10-membered ring, which is unsubstituted or substituted with one or more groups independently selected from the group consisting of $(C_1\text{-}C_6)$alkyl, halogen, hydroxy, —O—$(C_1\text{-}C_6)$alkyl, $(C_3\text{-}C_{10})$cycloalkyl, $(C_6\text{-}C_{10})$aryl, heterocycloalkyl, heteroaryl, amino and cyano;

heteroaryl is a 5- to 12-membered ring, which is unsubstituted or substituted with one or more groups independently selected from the group consisting of $(C_1\text{-}C_6)$alkyl, halogen, hydroxy, —O—$(C_1\text{-}C_6)$alkyl, $(C_3\text{-}C_{10})$cycloalkyl, $(C_6\text{-}C_{10})$aryl, heterocycloalkyl, heteroaryl, amino and cyano;

heterocycloalkyl is a 5- to 12-membered ring, which is unsubstituted or substituted with one or more groups independently selected from the group consisting of $(C_1\text{-}C_6)$alkyl, halogen, hydroxy, —O—$(C_1\text{-}C_6)$alkyl, $(C_3\text{-}C_{10})$cycloalkyl, $(C_6\text{-}C_{10})$aryl, heterocycloalkyl, heteroaryl, amino and cyano;

halogen is chlorine, bromine, iodine or fluorine;

or a stereoisomer, a tautomer, a pharmaceutically acceptable salt, a pharmaceutically acceptable solvate, a prodrug, a polymorph, N-oxide, S-oxide, or a carboxylic acid isostere thereof.

In an embodiment, the present invention encompasses a compound of Formula (I), wherein Ring A is unsubstituted or substituted 3- to 10-membered cycloalkyl.

In one embodiment, the present invention encompasses a compound of Formula (I), wherein Ring A is unsubstituted or substituted 5- to 12-membered heterocycloalkyl containing 1, 2, 3 or 4 heteroatoms independently selected from the group consisting of N, O and S.

In an embodiment, the present invention encompasses a compound of Formula (I), wherein Ring A is unsubstituted or substituted $(C_6\text{-}C_{10})$aryl.

In an embodiment, the present invention encompasses a compound of Formula (I), wherein Ring A is 5- to 12-membered heteroaryl containing 1, 2, 3 or 4 heteroatoms independently selected from the group consisting of N, O and S.

In an embodiment, the present invention encompasses a compound of Formula (I), wherein Ring A is unsaturated or partially unsaturated $(C_6\text{-}C_{10})$aryl.

In an embodiment, the present invention encompasses a compound of Formula (I), wherein Ring A is unsaturated or partially unsaturated 5- to 12-membered heteroaryl.

In an embodiment, the present invention encompasses a compound of Formula (I), wherein Ring A is

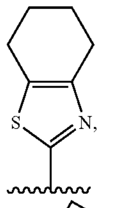
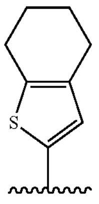,
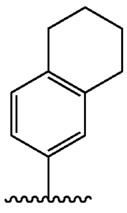
or
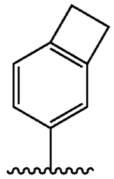

⌇ represents a point of attachment to Ring B.

In an embodiment, the present invention encompasses a compound of Formula (I), wherein Ring B is unsubstituted or substituted $(C_6\text{-}C_{10})$aryl.

In an embodiment, the present invention encompasses a compound of Formula (I), wherein Ring B is 5- to 12-membered heteroaryl containing 1, 2 or 3 heteroatoms independently selected from the group consisting of N, O and S.

In an embodiment, the present invention encompasses a compound of Formula (I), wherein Ring B is unsubstituted or substituted phenyl.

In an embodiment, the present invention encompasses a compound of Formula (I), wherein Ring B is unsubstituted or substituted phenyl, and $R^2$ is located at para position to Ring A and is as defined above; and n is 1.

In an embodiment, the present invention encompasses a compound of Formula (I), wherein Ring B is phenyl and $R^2$ is halogen located at para position to Ring A and is as defined above; and n is 1.

In an embodiment, the present invention encompasses a compound of Formula (I), wherein Ring C is unsubstituted or substituted $(C_6\text{-}C_{10})$aryl.

In an embodiment, the present invention encompasses a compound of Formula (I), wherein Ring C is 5- to 12-membered heteroaryl containing 1, 2 or 3 heteroatoms independently selected from the group consisting of N, O and S.

In an embodiment, the present invention encompasses a compound of Formula (I), wherein Ring C is unsubstituted or substituted phenyl, or unsubstituted or substituted 5- to 6-membered heteroaryl.

In an embodiment, the present invention encompasses a compound of Formula (I), wherein Ring C is unsubstituted or substituted phenyl.

In an embodiment, the present invention encompasses a compound of Formula (I), wherein Ring C is unsubstituted or substituted 5- to 6-membered heteroaryl.

In an embodiment, the present invention encompasses a compound of Formula (I), wherein Ring C is unsubstituted or substituted phenyl, or unsubstituted or substituted 6-membered heteroaryl.

In an embodiment, the present invention encompasses a compound of Formula (I), wherein two $R^1$ are combined together with Ring A to form a 3- to 6-membered cycloalkyl or 5- to 12-membered heterocycloalkyl.

In an embodiment, the present invention encompasses a compound of Formula (I), wherein two $R^1$ are combined together with Ring A to form a 3- to 6-membered cycloalkyl.

In an embodiment, the present invention encompasses a compound of Formula (I), wherein Ring B is unsubstituted or substituted phenyl; Ring C is unsubstituted or substituted phenyl, or unsubstituted or substituted 5- to 6-membered heteroaryl; $R^2$ is located at para position to Ring A and is as defined above; $R^3$ is hydrogen; and m & n are 1.

In an embodiment, the present invention encompasses a compound of Formula (I), wherein Ring B is unsubstituted or substituted phenyl; Ring C is unsubstituted or substituted phenyl, $R^2$ is halogen located at para position to Ring A; $R^3$ is hydrogen; and m & n are 1.

In an embodiment, the present invention encompasses a compound of Formula (I), wherein Ring B is unsubstituted or substituted phenyl; Ring C is unsubstituted or substituted 5- to 6-membered heteroaryl; $R^2$ is located at para position to Ring A and is as defined above; $R^3$ is hydrogen; and m & n are 1.

In an embodiment, the present invention encompasses a compound of Formula (I), wherein Ring B is unsubstituted or substituted $(C_6-C_{10})$aryl or 5- to 12-membered heteroaryl; Ring C is unsubstituted or substituted $(C_6-C_{10})$aryl or 5- to 12-membered heteroaryl; Ring A is saturated or partially unsaturated 5- to 12-membered bicyclic heteroaryl or 5- to 12-membered bicyclic heterocycloalkyl; X, $R^1$, $R^2$, $R^3$, m, n & p are as defined above.

In an embodiment, the present invention encompasses a compound of Formula (I), wherein Ring B is unsubstituted or substituted $(C_6-C_{10})$aryl or 5- to 12-membered heteroaryl; Ring C is unsubstituted or substituted $(C_6-C_{10})$aryl or 5- to 12-membered heteroaryl; Ring A is 5- to 6-membered monocyclic heteroaryl; $R^1$ is 3- to 10-membered cycloalkyl; X, $R^2$, $R^3$, m, n & p are as defined above.

In an embodiment, the present invention encompasses a compound of Formula (I), wherein X is

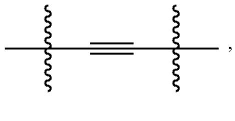 [SMILES: *C#C*]

wherein ⦚ represents a point of attachment.

In an embodiment, the present invention encompasses a compound of Formula (I), wherein X is

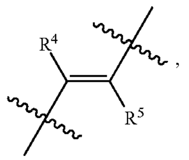

wherein $R^4$ and $R^5$ are as defined above, and ⦚ represents a point of attachment.

In an embodiment, the present invention encompasses a compound of Formula (I), wherein X is

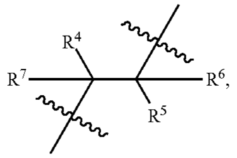

wherein $R^4$, $R^5$, $R^6$ and $R^7$ are as defined above, and ⦚ represents a point of attachment.

In another embodiment, the present invention encompasses a compound of Formula (I), wherein R is hydrogen.

In another embodiment, the present invention encompasses a compound of Formula (I), wherein R is $(C_1-C_6)$ alkyl.

In an embodiment, the compound of Formula I encompasses a compound of Formula IA;

Formula IA

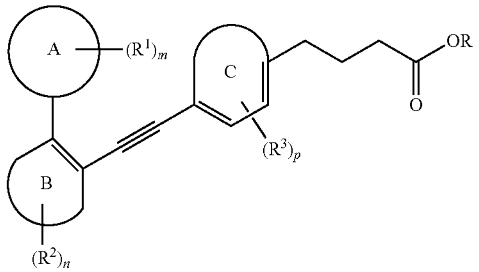

(IA)

wherein,

Ring A is 3- to 10-membered cycloalkyl, 5- to 12-membered heterocycloalkyl; $(C_6-C_{10})$aryl or 5- to 12-membered heteroaryl, wherein the heterocycloalkyl and the heteroaryl contain 1, 2, 3 or 4 heteroatoms independently selected from the group consisting of N, O and S;

Ring B and Ring C are independently selected from $(C_6-C_{10})$aryl or 5- to 12-membered heteroaryl containing 1, 2 or 3 heteroatoms independently selected from the group consisting of N, O and S;

R is hydrogen or $(C_1-C_6)$alkyl;

$R^1$, $R^2$ and $R^3$ at each occurrence are independently selected from the group consisting of hydrogen, halogen, $(C_1-C_6)$ alkyl, halo$(C_1-C_6)$alkyl, 3- to 10-membered cycloalkyl and 5- to 12-membered heterocycloalkyl;

m, n and p are each an integer independently selected from 1, 2 and 3;

wherein, $(C_1-C_6)$alkyl is unsubstituted or substituted with one or more groups independently selected from the group consisting of halogen, hydroxy, cyano, nitro, $(C_1-C_6)$alkyl, halo $(C_1-C_6)$alkyl, —$O(C_1-C_6)$alkyl, $(C_3-C_{10})$cycloalkyl, $(C_6-C_{10})$aryl, heterocycloalkyl and heteroaryl;

cycloalkyl is a 3- to 10-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino and cyano;

heteroaryl is a 5- to 12-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino and cyano;

heterocycloalkyl is a 5- to 12-membered ring, which is unsubstituted or substituted with one or more groups independently selected from the group consisting of $(C_1-C_6)$ alkyl, halogen, hydroxy, —O—$(C_1-C_6)$alkyl, $(C_3-C_{10})$cycloalkyl, $(C_6-C_{10})$aryl, heterocycloalkyl, heteroaryl, amino and cyano;

halogen is chlorine, bromine, iodine or fluorine;

or a stereoisomer, a tautomer, a pharmaceutically acceptable salt, a pharmaceutically acceptable solvate, a prodrug, a polymorph, N-oxide, S-oxide, or a carboxylic acid isostere thereof.

In an embodiment, the compound of Formula (I) encompasses the compound of Formula IA, wherein Ring A is 3- to 10-membered cycloalkyl, 5- to 12-membered heterocycloalkyl; $(C_6-C_{10})$aryl or 5- to 12-membered heteroaryl;

Ring B is $(C_6-C_{10})$aryl;

Ring C is $(C_6-C_{10})$aryl or 5- to 12-membered heteroaryl;

$R^1$, $R^2$ and $R^3$ at each occurrence are independently selected from the group consisting of hydrogen, halogen, $(C_1-C_6)$ alkyl, 3- to 10-membered cycloalkyl and 5- to 12-membered heterocycloalkyl;

m, n and p are each integer independently selected from 1 or 2, and

R is hydrogen or $(C_1-C_6)$alkyl.

In an embodiment, the compound of Formula (I) encompasses the compound of Formula IA, wherein Ring A is 5- to 12-membered heterocycloalkyl, $(C_6-C_{10})$aryl or 5- to 12-membered heteroaryl;

Ring B is $(C_6-C_{10})$aryl;

Ring C is $(C_6-C_{10})$aryl or 5- to 6-membered heteroaryl;

$R^1$ is hydrogen, halogen, $(C_1-C_6)$alkyl, 3- to 10-membered cycloalkyl or 5- to 12-membered heterocycloalkyl;

$R^2$ and $R^3$ at each occurrence are independently selected from the group consisting of hydrogen, halogen and $(C_1-C_6)$alkyl;

m, n and p are each integer independently selected from 1 or 2; and

R is hydrogen or $(C_1-C_6)$alkyl.

In an embodiment, the compound of Formula (I) encompasses the compound of Formula IA, wherein Ring A is 5- to 12-membered heterocycloalkyl or 5- to 12-membered heteroaryl;

Ring B is phenyl;

Ring C is phenyl or 5- to 6-membered heteroaryl;

$R^1$ is hydrogen, halogen, $(C_1-C_6)$alkyl, 3- to 10-membered cycloalkyl or 5- to 12-membered heterocycloalkyl;

$R^2$ and $R^3$ at each occurrence are independently selected from the group consisting of hydrogen and halogen;

m, n and p are 1; and

R is hydrogen or $(C_1-C_6)$alkyl.

In an embodiment, the compound of Formula (I) encompasses the compound of Formula IA, wherein Ring A is 5- to 12-membered heterocycloalkyl or 5- to 12-membered heteroaryl;

Ring B is phenyl;

Ring C is phenyl or 6-membered heteroaryl;

$R^1$ is hydrogen, halogen, $(C_1-C_6)$alkyl, 3- to 10-membered cycloalkyl or 5- to 12-membered heterocycloalkyl;

$R^2$ is halogen;

$R^3$ is hydrogen or halogen;

m, n and p are 1; and

R is hydrogen or $(C_1-C_6)$alkyl.

In an embodiment, the compound of Formula (I) encompasses the compound of Formula IA, wherein Ring B is unsubstituted or substituted phenyl.

In an embodiment, the compound of Formula (I) encompasses the compound of Formula IA, wherein Ring B is unsubstituted or substituted phenyl, and $R^2$ is located at para position to Ring A and is as defined above; and n is 1.

In an embodiment, the compound of Formula (I) encompasses the compound of Formula IA, wherein Ring B is phenyl and $R^2$ is halogen located at para position to Ring A; and n is 1.

In an embodiment, the compound of Formula (I) encompasses the compound of Formula IA, wherein Ring C is unsubstituted or substituted phenyl, or unsubstituted or substituted 5- to 6-membered heteroaryl.

In an embodiment, the compound of Formula (I) encompasses the compound of Formula IA, wherein Ring C is unsubstituted or substituted phenyl.

In an embodiment, the compound of Formula (I) encompasses the compound of Formula IA, wherein Ring C is unsubstituted or substituted 5- to 6-membered heteroaryl.

In an embodiment, the compound of Formula (I) encompasses the compound of Formula IA, wherein Ring B is unsubstituted or substituted phenyl; Ring C is unsubstituted or substituted phenyl, or unsubstituted or substituted 5- to 6-membered heteroaryl; $R^2$ is located at para position to Ring A and is as defined above; $R^3$ is hydrogen; and m & n are 1.

In an embodiment, the compound of Formula (I) encompasses the compound of Formula IA, wherein Ring B is unsubstituted or substituted phenyl; Ring C is unsubstituted or substituted phenyl, or unsubstituted or substituted 6-membered heteroaryl; $R^2$ is halogen located at para position to Ring A; $R^3$ is hydrogen; and m & n are 1.

In another aspect, the compound of Formula I encompasses a compound of Formula IB;

Formula IB (IB)

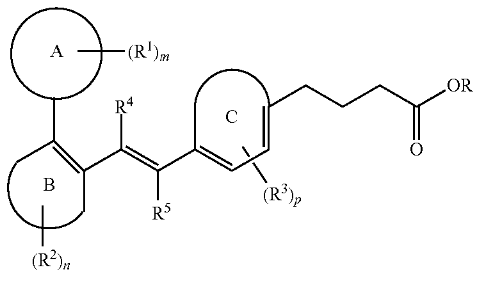

Ring A is 3- to 10-membered cycloalkyl, 5- to 12-membered heterocycloalkyl; $(C_6-C_{10})$aryl or 5- to 12-membered heteroaryl, wherein the heterocycloalkyl and the heteroaryl contain 1, 2, 3 or 4 heteroatoms independently selected from the group consisting of N, O and S;

Ring B and Ring C are independently selected from the group consisting of $(C_6-C_{10})$aryl or 5- to 12-membered heteroaryl containing 1, 2 or 3 heteroatoms independently selected from the group consisting of N, O and S;

R is hydrogen or $(C_1-C_6)$alkyl;

$R^1$, $R^2$ and $R^3$ at each occurrence are independently selected from the group consisting of hydrogen, halogen, $(C_1-C_6)$alkyl, halo$(C_1-C_6)$alkyl, 3- to 10-membered cycloalkyl, and 5- to 12-membered heterocycloalkyl;

$R^4$ is independently selected from hydrogen or $(C_1-C_6)$alkyl;

$R^5$ is independently selected from hydrogen, halogen or $(C_1-C_6)$alkyl;

m, n and p are each an integer independently selected from 1, 2 and 3;

wherein, $(C_1-C_6)$alkyl is unsubstituted or substituted with one or more groups independently selected from the group consisting of halogen, hydroxy, cyano, nitro, $(C_1-C_6)$alkyl, halo $(C_1-C_6)$alkyl, —O$(C_1-C_6)$alkyl, $(C_3-C_{10})$cycloalkyl, $(C_6-C_{10})$aryl, heterocycloalkyl and heteroaryl;

cycloalkyl is a 3- to 10-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino and cyano;

heteroaryl is a 5- to 12-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino and cyano;

heterocycloalkyl is a 5- to 12-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino and cyano;

halogen is selected from chlorine, bromine, iodine or fluorine;

or a stereoisomer, a tautomer, a pharmaceutically acceptable salt, a pharmaceutically acceptable solvate, a prodrug, a polymorph, N-oxide, S-oxide, or a carboxylic acid isostere thereof.

In an embodiment, the compound of Formula (I) encompasses the compound of Formula IB, wherein Ring A is 3- to 10-membered cycloalkyl, 5- to 12-membered heterocycloalkyl; $(C_6-C_{10})$aryl or 5- to 12-membered heteroaryl;

Ring B is $(C_6-C_{10})$aryl;

Ring C is $(C_6-C_{10})$aryl and 5- to 12-membered heteroaryl;

$R^1$, $R^2$ and $R^3$ at each occurrence are independently selected from the group consisting of hydrogen, halogen, $(C_1-C_6)$alkyl, 3- to 10-membered cycloalkyl and heterocycloalkyl;

m, n and p are each integer independently selected from 1 or 2, $R^4$ is independently selected from hydrogen or $(C_1-C_6)$alkyl;

$R^5$ is independently selected from hydrogen, halogen or $(C_1-C_6)$alkyl and

R is hydrogen or $(C_1-C_6)$alkyl.

In an embodiment, the compound of Formula (I) encompasses the compound of Formula IB, wherein Ring A is 5- to 10-membered heterocycloalkyl or 5- to 10-membered heteroaryl;

Ring B is $(C_6-C_{10})$aryl;

Ring C is $(C_6-C_{10})$aryl or 5- to 6-membered heteroaryl;

$R^1$ is hydrogen, halogen, $(C_1-C_6)$alkyl, 3- to 10-membered cycloalkyl or 5- to 12-membered heterocycloalkyl;

$R^2$ and $R^3$ at each occurrence are independently selected from the group consisting of hydrogen, halogen and $(C_1-C_6)$alkyl;

m, n and p are each integer independently selected from 1 or 2;

$R^4$ and $R^5$ are hydrogen, and

R is hydrogen or $(C_1-C_6)$alkyl.

In an embodiment, the compound of Formula (I) encompasses the compound of Formula IB, wherein Ring A is 5- to 10-membered heterocycloalkyl or 5- to 10-membered heteroaryl;

Ring B is $(C_6-C_{10})$aryl;

Ring C is $(C_6-C_{10})$aryl or 5- to 6-membered heteroaryl;

$R^1$ is hydrogen, halogen, $(C_1-C_6)$alkyl, 3- to 10-membered cycloalkyl or 5- to 12-membered heterocycloalkyl;

$R^2$ and $R^3$ at each occurrence are independently selected from the group consisting of hydrogen and halogen;

m, n and p are 1;

$R^4$ and $R^5$ are hydrogen, and

R is hydrogen or $(C_1-C_6)$alkyl.

In an embodiment, the compound of Formula (I) encompasses the compound of Formula IB, wherein Ring A is 5- to 12-membered heterocycloalkyl or 5- to 12-membered heteroaryl;

Ring B is phenyl;

Ring C is phenyl or 5- to 6-membered heteroaryl;

$R^1$ is hydrogen, halogen, $(C_1-C_6)$alkyl, 3- to 10-membered cycloalkyl or 5- to 12-membered heterocycloalkyl;

$R^2$ and $R^3$ are independently selected from the group consisting hydrogen and halogen;

m, n and p are 1;

$R^4$ and $R^5$ are hydrogen, and

R is hydrogen or $(C_1-C_6)$alkyl.

In an embodiment, the compound of Formula (I) encompasses the compound of Formula IB, wherein Ring A is 5- to 10-membered heterocycloalkyl or 5- to 10-membered heteroaryl;

Ring B and Ring C are phenyl;

$R^1$ is hydrogen, halogen, $(C_1-C_6)$alkyl, 3- to 10-membered cycloalkyl or 5- to 12-membered heterocycloalkyl;

$R^2$ and $R^3$ are independently selected from hydrogen or halogen;

m, n and p are 1;

$R^4$ and $R^5$ are hydrogen, and

R is hydrogen or $(C_1-C_6)$alkyl.

In an embodiment, the compound of Formula (I) encompasses the compound of Formula IB, wherein Ring B is unsubstituted or substituted phenyl.

In an embodiment, the compound of Formula (I) encompasses the compound of Formula IB, wherein Ring B is unsubstituted or substituted phenyl, and $R^2$ is located at para position to Ring A; and n is 1.

In an embodiment, the compound of Formula (I) encompasses the compound of Formula IB, wherein Ring B is phenyl and $R^2$ is halogen located at para position to Ring A; and n is 1.

In an embodiment, the compound of Formula (I) encompasses the compound of Formula IB, wherein Ring C is unsubstituted or substituted phenyl, or unsubstituted or substituted 5- to 6-membered heteroaryl.

In an embodiment, the compound of Formula (I) encompasses the compound of Formula IB, wherein Ring C is unsubstituted or substituted phenyl.

In an embodiment, the compound of Formula (I) encompasses the compound of Formula IB, wherein Ring C is unsubstituted or substituted 5- to 6-membered heteroaryl.

In an embodiment, the compound of Formula (I) encompasses the compound of Formula IB, wherein Ring B is unsubstituted or substituted phenyl; Ring C is unsubstituted or substituted phenyl, or unsubstituted or substituted 5- to 6-membered heteroaryl; $R^2$ is located at para position to Ring A and is as defined above; $R^3$ is hydrogen; and m & n are 1.

In an embodiment, the compound of Formula (I) encompasses the compound of Formula IB, wherein Ring B is unsubstituted or substituted phenyl; Ring C is unsubstituted or substituted phenyl, or unsubstituted or substituted 5- to 6-membered heteroaryl; $R^2$ is halogen located at para position to Ring A; $R^3$ is hydrogen; and m & n are 1.

In an embodiment, the compound of Formula (I) encompasses the compound of Formula IB, wherein Ring B is unsubstituted or substituted phenyl; Ring C is unsubstituted or substituted phenyl, or unsubstituted or substituted 6-membered heteroaryl; $R^2$ is halogen located at para position to Ring A; $R^3$ is hydrogen; m & n are 1; and $R^4$ and $R^5$ are hydrogen.

In another aspect, the compound of Formula I encompasses a compound of Formula IC, Formula IC (IC)

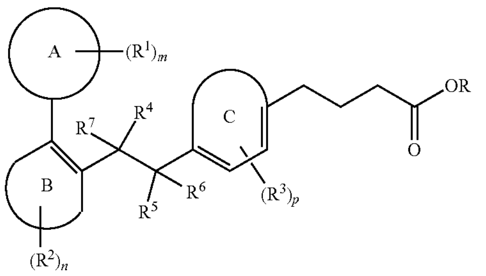

wherein,

Ring A is 3- to 10-membered cycloalkyl, 5- to 12-membered heterocycloalkyl; $(C_6\text{-}C_{10})$aryl or 5- to 12-membered heteroaryl, wherein the heterocycloalkyl and the heteroaryl contain 1, 2, 3 or 4 heteroatoms independently selected from the group consisting of N, O and S;

Ring B and Ring C are independently selected from the group consisting of $(C_6\text{-}C_{10})$aryl or 5- to 12-membered heteroaryl containing 1, 2 or 3 heteroatoms independently selected from the group consisting of N, O and S;

R is hydrogen or $(C_1\text{-}C_6)$alkyl;

$R^1$, $R^2$ and $R^3$ at each occurrence is independently selected from the group consisting of hydrogen, halogen, $(C_1\text{-}C_6)$ alkyl, halo$(C_1\text{-}C_6)$alkyl, 3- to 10-membered cycloalkyl and 5- to 12-membered heterocycloalkyl;

$R^4$ and $R^7$ are independently selected from hydrogen or $(C_1\text{-}C_6)$alkyl;

$R^5$ and $R^6$ are independently selected from the group consisting of hydrogen, halogen and $(C_1\text{-}C_6)$alkyl;

m, n and p are each an integer independently selected from 1, 2 or 3;

wherein, $(C_1\text{-}C_6)$alkyl is unsubstituted or substituted with one or more groups independently selected from the group consisting of halogen, hydroxy, cyano, nitro, $(C_1\text{-}C_6)$alkyl, halo $(C_1\text{-}C_6)$alkyl, —O$(C_1\text{-}C_6)$alkyl, $(C_3\text{-}C_{10})$cycloalkyl, $(C_6\text{-}C_{10})$aryl, heterocyclyl and heteroaryl;

cycloalkyl is a 3- to 10-membered ring, which is unsubstituted or substituted with one or more groups independently selected from the group consisting of $(C_1\text{-}C_6)$alkyl, halogen, hydroxy, —O—$(C_1\text{-}C_6)$alkyl, $(C_3\text{-}C_{10})$cycloalkyl, $(C_6\text{-}C_{10})$aryl, heterocyclyl, heteroaryl, amino and cyano;

heteroaryl is a 5- to 12-membered ring, which is unsubstituted or substituted with one or more groups independently selected from the group consisting of $(C_1\text{-}C_6)$alkyl, halogen, hydroxy, —O—$(C_1\text{-}C_6)$alkyl, $(C_3\text{-}C_{10})$cycloalkyl, $(C_6\text{-}C_{10})$aryl, heterocycloalkyl, heteroaryl, amino and cyano;

heterocycloalkyl is a 5- to 12-membered ring, which is unsubstituted or substituted with one or more groups independently selected from the group consisting of $(C_1\text{-}C_6)$ alkyl, halogen, hydroxy, —O—$(C_1\text{-}C_6)$alkyl, $(C_3\text{-}C_{10})$cycloalkyl, $(C_6\text{-}C_{10})$aryl, heterocycloalkyl, heteroaryl, amino and cyano;

halogen is selected from chlorine, bromine, iodine or fluorine;

or a stereoisomer, a tautomer, a pharmaceutically acceptable salt, a pharmaceutically acceptable solvate, a prodrug, a polymorph, N-oxide, S-oxide, or a carboxylic acid isostere thereof.

In an embodiment, the compound of Formula (I) encompasses the compound of Formula IC, wherein Ring A is 3- to 10-membered cycloalkyl, 5- to 12-membered heterocycloalkyl; $(C_6\text{-}C_{10})$aryl or 5- to 12-membered heteroaryl;

Ring B is $(C_6\text{-}C_{10})$aryl;

Ring C is $(C_6\text{-}C_{10})$aryl or 5- to 12-membered heteroaryl;

$R^1$, $R^2$ and $R^3$ at each occurrence are independently selected from the group consisting of hydrogen, halogen, $(C_1\text{-}C_6)$ alkyl, 3- to 10-membered cycloalkyl and heterocycloalkyl;

m, n and p are each integer independently selected from 1 or 2, $R^4$ and $R^7$ are independently selected from hydrogen or $(C_1\text{-}C_6)$alkyl;

$R^5$ and $R^6$ are independently selected from hydrogen or halogen; and

R is hydrogen or $(C_1\text{-}C_6)$alkyl.

In an embodiment, the compound of Formula (I) encompasses the compound of Formula IC, wherein Ring A is 3- to 8-membered cycloalkyl, 5- to 10-membered heterocycloalkyl or 5- to 10-membered heteroaryl;

Ring B is $(C_6\text{-}C_{10})$aryl;

Ring C is $(C_6\text{-}C_{10})$aryl or 5- to 6-membered heteroaryl;

$R^1$ is hydrogen, halogen, $(C_1\text{-}C_6)$alkyl, 3- to 10-membered cycloalkyl or 5- to 12-membered heterocycloalkyl;

$R^2$ and $R^3$ at each occurrence are independently selected from the group consisting of hydrogen, halogen and $(C_1\text{-}C_6)$alkyl;

m, n and p are each integer independently selected from 1 or 2;

$R^4$ and $R^7$ are hydrogen;

$R^5$ and $R^6$ are independently selected from hydrogen or halogen; and

R is hydrogen or $(C_1\text{-}C_6)$alkyl.

In an embodiment, the compound of Formula (I) encompasses the compound of Formula IC, wherein Ring A is 5- to 10-membered heterocycloalkyl or 5- to 10-membered heteroaryl;

Ring B is phenyl;

Ring C is phenyl or 5- to 6-membered heteroaryl;

$R^1$ is hydrogen, halogen, $(C_1\text{-}C_6)$alkyl, 3- to 10-membered cycloalkyl or 5- to 12-membered heterocycloalkyl;

$R^2$ and $R^3$ are independently selected from hydrogen or halogen;

m, n and p are 1;

$R^4$ and $R^7$ are hydrogen;

$R^5$ and $R^6$ are halogen; and

R is hydrogen or $(C_1\text{-}C_6)$alkyl.

In an embodiment, the compound of Formula (I) encompasses the compound of Formula IC, wherein Ring A is 5- to 10-membered heterocycloalkyl or 5- to 10-membered heteroaryl;

Ring B and Ring C are phenyl;

$R^1$ is hydrogen, halogen, $(C_1\text{-}C_6)$alkyl, 3- to 10-membered cycloalkyl or 5- to 12-membered heterocycloalkyl;

$R^2$ and $R^3$ are hydrogen or halogen;

m, n and p are 1;

$R^4$ and $R^7$ are hydrogen;

$R^5$ and $R^6$ are halogen; and

R is hydrogen or $(C_1\text{-}C_6)$alkyl.

In an embodiment, the compound of Formula (I) encompasses the compound of Formula IC, wherein Ring B is unsubstituted or substituted phenyl.

In an embodiment, the compound of Formula (I) encompasses the compound of Formula IC, wherein Ring B is unsubstituted or substituted phenyl, and $R^2$ is located at para position to Ring A and is as defined above; and n is 1.

In an embodiment, the compound of Formula (I) encompasses the compound of Formula IC, wherein Ring B is phenyl and $R^2$ is halogen located at para position to Ring A; and n is 1.

In an embodiment, the compound of Formula (I) encompasses the compound of Formula IC, wherein Ring C is unsubstituted or substituted phenyl, or unsubstituted or substituted 5- to 6-membered heteroaryl.

In an embodiment, the compound of Formula (I) encompasses the compound of Formula IC, wherein Ring C is unsubstituted or substituted phenyl.

In an embodiment, the compound of Formula (I) encompasses the compound of Formula IC, wherein Ring C is unsubstituted or substituted 5- to 6-membered heteroaryl.

In an embodiment, the compound of Formula (I) encompasses the compound of Formula IC, wherein Ring B is unsubstituted or substituted phenyl; Ring C is unsubstituted or substituted phenyl, or unsubstituted or substituted 5- to 6-membered heteroaryl; $R^2$ is located at para position to Ring A and is as defined above; $R^3$ is hydrogen; and m & n are 1.

In an embodiment, the compound of Formula (I) encompasses the compound of Formula IC, wherein Ring B is unsubstituted or substituted phenyl; Ring C is unsubstituted or substituted phenyl, or unsubstituted or substituted 5- to 6-membered heteroaryl; $R^2$ is halogen located at para position to Ring A; $R^3$ is hydrogen; and m & n are 1.

In an embodiment, the compound of Formula (I) encompasses the compound of Formula IC, wherein Ring B is unsubstituted or substituted phenyl; Ring C is unsubstituted or substituted phenyl, or unsubstituted or substituted 5- to 6-membered heteroaryl; $R^2$ is halogen located at para position to Ring A; $R^3$ is hydrogen; m & n are 1; $R^4$ and $R^7$ are hydrogen; and $R^5$ and $R^6$ are halogen.

In an embodiment, the compound of Formula (I) encompasses the compound of Formula ID, Formula ID (ID)

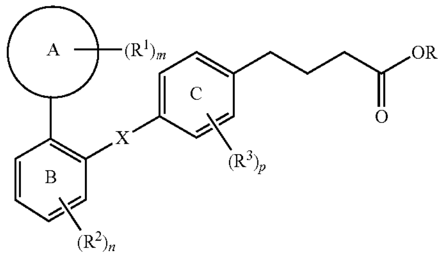

wherein,

Ring A is 3- to 10-membered cycloalkyl, 5- to 12-membered heterocycloalkyl; $(C_6\text{-}C_{10})$aryl or 5- to 12-membered heteroaryl; wherein the heterocycloalkyl and the heteroaryl contain 1, 2, 3 or 4 heteroatoms independently selected from the group consisting of N, O and S;

Ring B and Ring C are independently selected from $(C_6\text{-}C_{10})$aryl or 5- to 12-membered heteroaryl containing 1, 2 or 3 heteroatoms independently selected from the group consisting of N, O and S;

X is

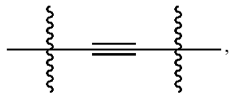,

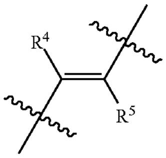

or

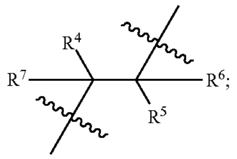

wherein ⌇ represents a point of attachment;

R is hydrogen or $(C_1\text{-}C_6)$alkyl;

$R^1$, $R^2$ and $R^3$ at each occurrence are independently selected from the group consisting of hydrogen, halogen, $(C_1\text{-}C_6)$alkyl, halo$(C_1\text{-}C_6)$alkyl, 3- to 10-membered cycloalkyl and 5- to 12-membered heterocycloalkyl;

$R^4$ and $R^7$ are independently selected from the group consisting of hydrogen and $(C_1\text{-}C_6)$alkyl;

$R^5$ and $R^6$ are independently selected from the group consisting of hydrogen, halogen and $(C_1\text{-}C_6)$alkyl;

m, n and p are each integer independently selected from 1, 2 and 3;

wherein, $(C_1\text{-}C_6)$alkyl is unsubstituted or substituted with one or more groups independently selected from the group consisting of halogen, hydroxy, cyano, nitro, $(C_1\text{-}C_6)$alkyl, halo$(C_1\text{-}C_6)$alkyl, —O$(C_1\text{-}C_6)$alkyl, $(C_3\text{-}C_8)$cycloalkyl, $(C_6\text{-}C_{10})$aryl, heterocycloalkyl and heteroaryl;

cycloalkyl is a 3- to 10-membered ring, which is unsubstituted or substituted with one or more groups independently selected from the group consisting of $(C_1\text{-}C_6)$alkyl, halogen, hydroxy, —O—$(C_1\text{-}C_6)$alkyl, $(C_3\text{-}C_{10})$cycloalkyl, $(C_6\text{-}C_{10})$aryl, heterocycloalkyl, heteroaryl, amino and cyano;

heteroaryl is a 5- to 12-membered ring, which is unsubstituted or substituted with one or more groups independently selected from the group consisting of $(C_1\text{-}C_6)$alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino and cyano;

heterocycloalkyl is a 5- to 12-membered ring, which is unsubstituted or substituted with one or more groups independently selected from the group consisting of ($C_1$-$C_6$) alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino and cyano;

halogen is chlorine, bromine, iodine or fluorine;

or a stereoisomer, a tautomer, a pharmaceutically acceptable salt, a pharmaceutically acceptable solvate, a prodrug, a polymorph, N-oxide, S-oxide, or a carboxylic acid isostere thereof.

Representative compounds of Formula (I) encompassed in accordance with the present invention include:

4-(5-((5-Fluoro-2-(6-methoxypyridin-3-yl)phenyl)ethynyl) pyridin-2-yl)butanoic acid;

4-(5-(5-Fluoro-2-(6-methoxypyridin-3-yl)phenethyl)pyridin-2-yl)butanoic acid;

4-(5-((5-Fluoro-2-(5-methylthiophen-2-yl)phenyl)ethynyl) pyridin-2-yl)butanoic acid;

4-(5-(5-Fluoro-2-(5-methylthiophen-2-yl)phenethyl)pyridin-2-yl)butanoic acid;

4-(4-(1,1-Difluoro-2-(5-fluoro-2-(5-methylthiophen-2-yl) phenyl)ethyl)phenyl)butanoic acid;

4-(4-(1,1-Difluoro-2-(5-fluoro-2-(5-(1-methylcyclopropyl) thiophen-2-yl)phenyl)ethyl)phenyl)butanoic acid;

4-(4-(1,1-Difluoro-2-(4-fluoro-4'-methyl-[1,1'-biphenyl]-2-yl)ethyl)phenyl)butanoic acid;

4-(4-(2-(2-(5-Cyclopropylthiophen-2-yl)-5-fluorophenyl)-1,1-difluoroethyl)phenyl)butanoic acid;

4-(4-(2-(2-(2,3-Dihydrobenzofuran-5-yl)-5-fluorophenyl)-1,1-difluoroethyl)phenyl)butanoic acid;

4-(4-(2-(4'-Cyclopropyl-4-fluoro-[1,1'-biphenyl]-2-yl)-1,1-difluoroethyl)phenyl)butanoic acid;

4-(4-((2-(5-(1-Cyanocyclopropyl)thiophen-2-yl)-5-fluorophenyl)ethynyl)phenyl)butanoic acid;

4-(4-(5-fluoro-2-(4,5,6,7-tetrahydrobenzo[d]thiazol-2-yl) phenethyl)phenyl)butanoic acid;

4-(4-(2-(5-cyclopropylthiophen-2-yl)-5-fluorophenethyl) phenyl)butanoic acid;

4-(4-(5-fluoro-2-(5-(1-methylcyclopropyl)thiophen-2-yl) styryl)phenyl)butanoic acid;

4-(4-(2-(5-(1-cyanocyclopropyl)thiophen-2-yl)-5-fluorostyryl)phenyl)butanoic acid;

4-(4-(5-fluoro-2-(4,5,6,7-tetrahydrobenzo[b]thiophen-2-yl) styryl)phenyl)butanoic acid;

4-(4-(5-fluoro-2-(4,5,6,7-tetrahydrobenzo[d]thiazol-2-yl) styryl)phenyl)butanoic acid;

4-(4-((2-(5-cyclopropylthiophen-2-yl)-5-fluorophenyl)ethynyl)phenyl)butanoic acid;

4-(4-((5-fluoro-2-(4,5,6,7-tetrahydrobenzo[d]thiazol-2-yl) phenyl)ethynyl)phenyl)butanoic acid;

4-(4-(1,1-difluoro-2-(5-fluoro-2-(6-methoxypyridin-3-yl) phenyl)ethyl)phenyl)butanoic acid;

4-(4-(1,1-difluoro-2-(5-fluoro-2-(5,6,7,8-tetrahydronaphthalen-2-yl)phenyl)ethyl)phenyl)butanoic acid;

4-(4-(2-(2-(bicyclo[4.2.0]octa-1(6),2,4-trien-3-yl)-5-fluorophenyl)-1,1-difluoroethyl)phenyl)butanoic acid;

or a stereoisomer, a tautomer, a pharmaceutically acceptable salt or a pharmaceutically acceptable solvate thereof.

Specific compounds encompassed in the present invention can also be found in the examples set out below.

The compounds of the present invention also include stereoisomeric and tautomeric forms and mixtures thereof and their pharmaceutically acceptable salts, pharmaceutically acceptable solvates, pharmaceutically acceptable prodrugs, pharmaceutically acceptable polymorphs and N-oxides thereof.

In an aspect of the present invention, there are provided processes for the preparation of the compounds of Formula (I) or pharmaceutically acceptable salts thereof.

The compounds of Formula (I) can be prepared by various methods including using methods well known to a person skilled in the art. Examples of processes for the preparation of a compound of Formula (I) are described below and illustrated in the following schemes but are not limited thereto. It will be appreciated by the persons skilled in the art that within the processes described herein, the order of the synthetic steps employed may be varied and will depend inter alia on factors such as the nature of functional groups present in a particular substrate and the protecting group strategy (if any) to be adopted. Clearly, such factors will also influence the choice of reagents such as bases, solvents, coupling agents to be used in the reaction steps.

The reagents, reactants and intermediates used in the following processes are either commercially available or can be prepared according to standard procedures known in the art, for instance those reported in the literature references.

In the following schemes and the description of the processes, the starting compounds and the intermediates used for the synthesis of the compounds of the present invention are referred to by the symbols 1a, 1b, 1c, 1d, 1e, 1f, 1g, 1h, 1i, 1j, 1k, 1l, 1m, 1n, 2a, 2b, 2c, 2d, 2e, 2f, 2g, 2h, 2i, 2j, 2j, 2k, 2l, 2m, 2n, 3a, 3b, 3c, 3d, 3e, 3f and 3g respectively, for ease of reference.

Unless stated otherwise, throughout the process description, the corresponding substituent groups in the various formulae representing starting compounds and/or intermediates have the same meaning as that of the compound of Formula I as described in one or more embodiments of the invention.

Processes for the preparation of the compounds of Formula I in one or more embodiments as described above, are depicted in schemes, as presented herein below.

For ease of reference, the reaction steps shown in the Schemes, are referred to by using general symbols namely 1.1, 1.2, 1.3, 1.4, 1.5, 1.6, 1.7, 1.8, 1.9, 1.10, 1.11, 2.1, 2.2, 2.3, 2.4, 2.5, 2.6, 2.7, 2.8, 2.9, 2.10, 2.11, 3.1, 3.2, 3.3, 3.4 and 3.5 respectively.

The compounds of the present invention were purified by either flash chromatography (ISCO Combiflash® chromatography instrument from Teledyne Isco, Inc.) or silica gel column chromatography. Mass spectrometry (MS) was performed using a Esquire 4000 Mass spectrometer (from Bruker Daltonics), Nuclear magnetic resonance spectroscopy (NMR) was performed using a Bruker Avance NMR spectrometer (for the $^1$H NMR spectra acquired at 300 MHz and 500 MHz) and the chemical shifts were reported in δ (ppm).

Scheme 1: Preparation of the compound of Formula I [referred to in Scheme 1 as compound 1a, 1b, 1c, 1d, 1e, 1f, 1g, 1h, 1i, 1j, 1k, 1l, 1m and 1n wherein $R^1$, $R^2$, $R^3$, m, n and p are as defined in any one of the embodiments of the compound of Formula I as described herein].

Scheme 1
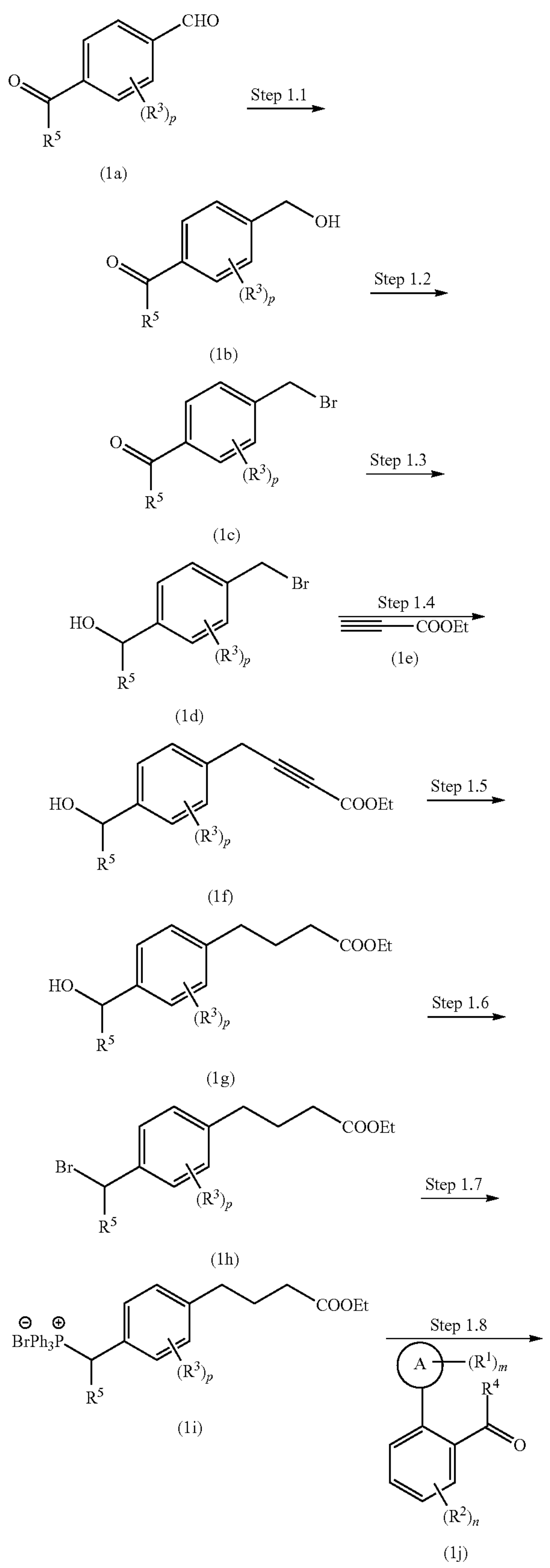
(1a) (1b) (1c) (1d) (1e) (1f) (1g) (1h) (1i) (1j)
-continued
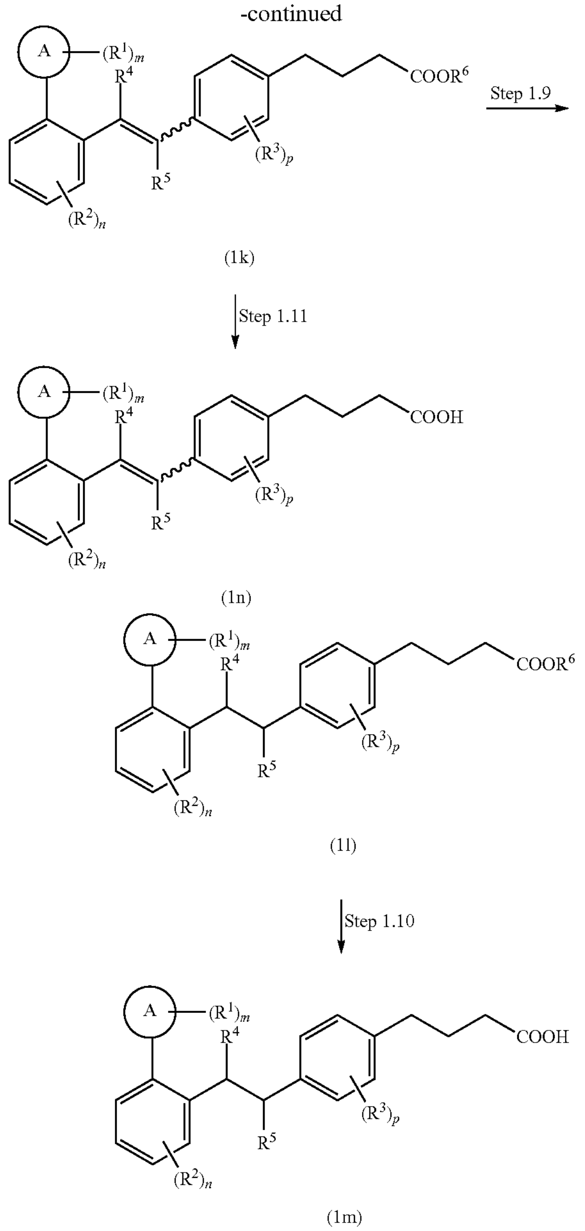
(1k) (1n) (1l) (1m)
Preparation of 1j
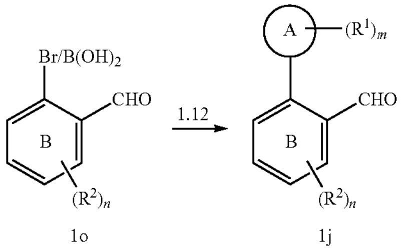
1o 1j
Reaction Conditions:
Step 1.1: $NaBH_4$(Sodium borohydride), THF:Ethanol (40:28) at −5° C. for 6 hours.
Step 1.2: $PBr_3$ (Phosphorus tribromide) at 0° C. for 0.5 hours.
Step 1.3: $NaBH_4$ (Sodium borohydride), Methanol at −5° C. for 0.5 hours Step 1.4: CuI (Copper Iodide), TBAI (Tetrabutylammonium iodide), $K_2CO_3$ (Potassium carbonate), ACN (Acetonitrile), 40° C. for 24 hours.

Step 1.5: $H_2$, Pd/C, Methanol

Step 1.6: $PBr_3$ (Phosphorus tribromide) at 0° C. for 0.5 hours.

Step 1.7: $PPh_3$ (Triphenylphosphine), Toluene, 60° C. for 2 hours

Step 1.8: NaOMe (Sodium methoxide), Methanol, 1 hour

Step 1.9: $H_2$, Pd, C, Methanol

Step 1.10: LiOH.$H_2$O/THF:MeOH (4:1), 24 hours.

Step 1.11: LiOH.$H_2$O/THF:MeOH (4:1), 24 hours.

Step 1.12: Suzuki coupling: Tetrakis(triphenylphosphine) palladium(0), Sodium bicarbonate, water, dioxane, DMF (Dimethylformamide)

Step 1.1:

Compound 1a (wherein $R^5$ is hydrogen or methyl; $R^3$ and p are as defined in any one of the embodiments of the compound of Formula I described herein) is reacted with 0.25 equivalents of $NaBH_4$ (Sodium borohydride) and a solvent mixture THF:Ethanol (40:28) at a temperature of −5° C. for 6 hours to obtain the compound 1b (wherein $R^5$, $R^3$ and p are as defined for compound 1a).

Step 1.2:

In this process step, the compound 1b is treated with 0.4 equivalents of $PBr_3$ (Phosphorus tribromide) at a temperature of 0° C. for 0.5 hours to obtain the compound 1c (wherein $R^5$; $R^3$ and p are as defined for compound 1a).

Step 1.3:

In this process step, the compound 1c is treated with $NaBH_4$ (Sodium borohydride) and a solvent such as methanol at a temperature of −5° C. for 0.5 hours to obtain the compound 1d (wherein $R^5$; $R^3$ and p are as defined for compound 1a).

Step 1.4:

In this process step, the compound 1d is subjected to Sonogashira coupling. Compound 1d is treated with a compound of formula 1e, 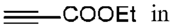 in the presence of copper(I) iodide, a base such as TBAI (tetrabutylammonium iodide), $K_2CO_3$ (potassium carbonate) and a solvent such as acetonitrile to obtain the compound 1f (wherein $R^5$; $R^3$ and p are as defined for compound 1a).

Step 1.5:

The compound 1f is treated with hydrogen, palladium catalyst in a solvent such as methanol to obtain compound 1g (wherein $R^5$; $R^3$ and p are as defined for compound 1a).

Step 1.6:

The compound 1g is treated with 0.4 equivalents of $PBr_3$ (Phosphorus tribromide) at a temperature of 0° C. for 0.5 hours to obtain the compound 1h (wherein $R^5$, $R^3$ and p are as defined for compound 1a).

Step 1.7:

Treatment of the compound 1h with triphenylphosphine and toluene at a temperature of 60° C. for 2 hours resulted in compound of formula 1i, a Wittig salt (wherein $R^5$; $R^3$ and p are as defined for compound 1a).

Step 1.8:

In this process step, the compound 1i is treated with a compound of formula 1j, (1j)

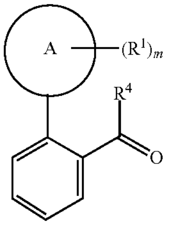

in the presence of NaOMe (Sodium methoxide) and a solvent such as methanol for 1 hour to obtain compound 1k (wherein $R^4$ and $R^5$ are hydrogen or methyl; $R^1$, $R^2$, $R^3$, m and p are as defined in any one of the embodiments of the compound of Formula I described herein).

Step 1.9:

The compound 1k is treated with Pd/C under hydrogen in a solvent such as methanol to obtain compound 11 (wherein $R^4$ and $R^5$ are hydrogen or methyl; $R^1$, $R^2$, $R^3$, m and p are as defined in any one of the embodiments of the compound of Formula I described herein).

Step 1.10:

The compound 11 is treated lithium hydroxide in a solvent mixture such as THF:methanol (4:1) for 24 hours to obtain compound 1m (wherein $R^4$ and $R^5$ are hydrogen or methyl; $R^1$, $R^2$, $R^3$, m and p are as defined in any one of the embodiments of the compound of Formula I described herein).

Step 1.11:

The compound 1k is treated with lithium hydroxide in a solvent mixture such as THF:methanol (4:1) for 24 hours to obtain compound 1n (wherein $R^4$ and $R^5$ are hydrogen or methyl; $R^1$, $R^2$, $R^3$, m and p are as defined in any one of the embodiments of the compound of Formula I described herein).

Step 1.12:

Preparation of compound of formula 1j: Suzuki coupling reaction of substituted bromobenzaldehyde compound (1o) (wherein $R^2$ and n are as defined in any one of the embodiments of the compound of Formula I described herein) using tetrakis(triphenylphosphine)palladium(0), sodium bicarbonate in water, in solvent dioxane, DMF (dimethylformamide) resulted in compound (1j) (wherein $R^1$, $R^2$, m and n are as defined in any one of the embodiments of the compound of Formula I described herein).

Scheme 2: Preparation of the compound of Formula I [referred in Scheme 2 as the compound 2n (wherein $R^4$ and $R^5$ are hydrogen or methyl; $R^1$, $R^2$, $R^3$, m and p are as defined in any one of the embodiments of the compound of Formula I described herein)].

Scheme 2

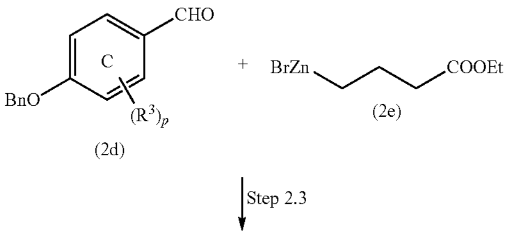

(2d) (2e)

-continued
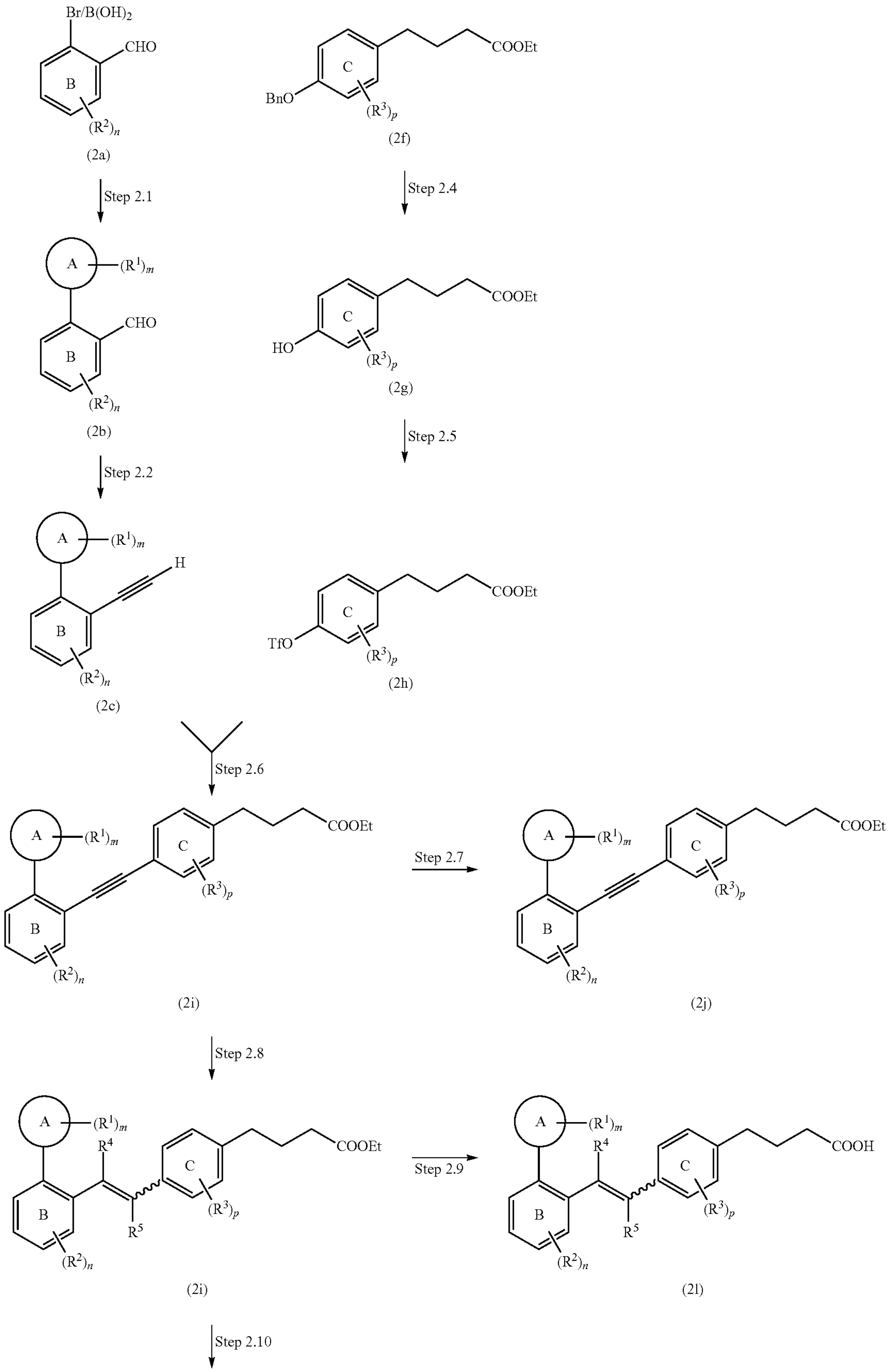

-continued

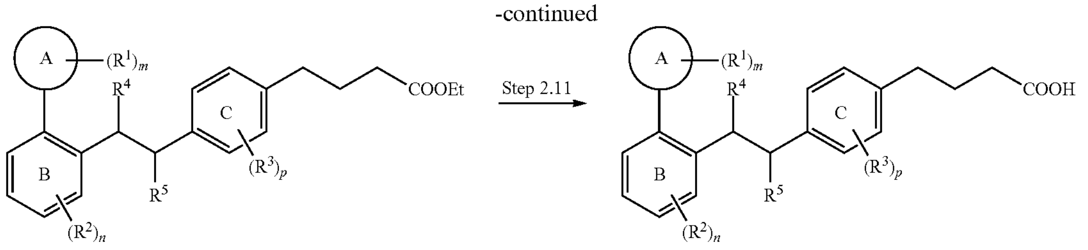

(2m) (2n)

Ring C =

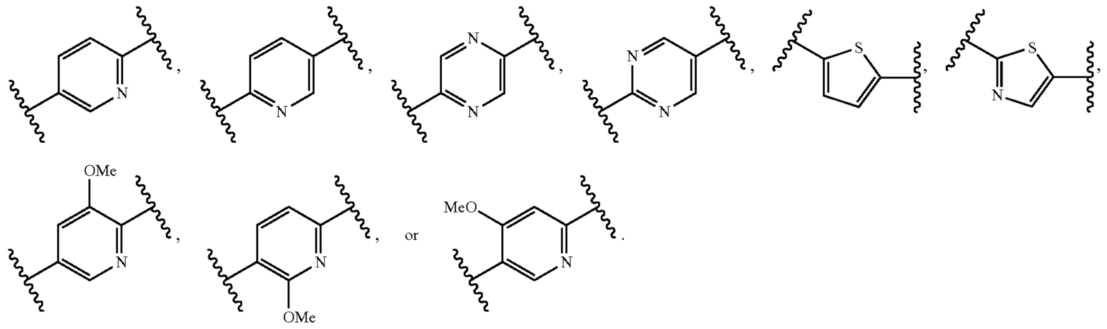

Reaction Condition:

Step 2.1: Suzuki coupling, Tetrakis(triphenylphosphine)palladium(0), Sodium bicarbonate, water, dioxane, DMF (Dimethylformamide)

Step 2.2: Dimethyl (1-diazo-2-oxopropyl)phosphonate, $K_2CO_3$ (potassium carbonate), methanol.

Step 2.3: PEPPSI-IPr catalyst [1,3-Bis(2,6-Diisopropylphenyl)imidazol-2-ylidene](3-chloropyridyl)palladium(II) dichloride or Pd(0).

Step 2.4: Hydrogen, Pd/C, ethanol

Step 2.5: Trifluoromethanesulfonic anhydride ($Tf_2O$), Pyridine

Step 2.6: CuI (Copper Iodide), LiCl (Lithium chloride), TEA (Triethanolamine), $Pd(PPh_3)_2C_2$ (Bis(triphenylphosphine) palladium(II) dichloride)

Step 2.7: $LiOH.H_2O$, THF:methanol (4:1) for 24 hours.

Step 2.8: $H_2$, Lindlar catalyst, 5% palladium on calcium carbonate; poisoned with lead.

Step 2.9: $LiOH.H_2O$, THF:methanol (4:1), 24 hours.

Step 2.10: $H_2$, Pd/C

Step 2.11: $LiOH.H_2O$, THF:methanol (4:1), 24 hours.

Step 2.1:

Suzuki coupling reaction of substituted bromobenzaldehyde compound (2a) (wherein $R^2$ and n are as defined in any one of the embodiments of the compound of Formula I described herein) with a suitably substituted boronic acid compound, using tetrakis(triphenylphosphine)palladium(0) resulted in compound (2b) (wherein $R^1$, $R^2$, m and n are as defined in any one of the embodiments of the compound of Formula I described herein).

Step 2.2:

In this process step, the compound 2b is treated with dimethyl (1-diazo-2-oxopropyl)phosphonate or trimethylsilyldiazomethane, LDA (Lithium diisopropylamide) in the presence of a base selected from $K_2CO_3$ or $NaHCO_3$ in THF and a solvent such as methanol to obtain an ethynyl compound (2c) (wherein $R^1$, $R^2$, m and n are as defined in any one of the embodiments of the compound of Formula I described herein).

Step 2.3:

In this process step, bromo compound of formula (2d) (wherein $R^3$ and p are as defined in any one of the embodiments of the compound of Formula I described herein) is subjected to Negishi Coupling with (4-ethoxy-4-oxobutyl) zinc(II) bromide compound (2e) in the presence of PEPPSI-IPr catalyst [1,3-Bis(2,6-diisopropylphenyl)imidazol-2-ylidene](3-chloropyridyl)palladium(II) dichloride or Pd(0), under argon atmosphere in THF to obtain compound (2f) (wherein $R^3$ and p are as defined in any one of the embodiments of the compound of Formula I described herein).

Step 2.4:

In this process step, the compound 2f is treated with Pd/C under hydrogen in ethanol to obtain the corresponding hydroxyl compound (2g) (wherein $R^3$ and p are as defined in any one of the embodiments of the compound of Formula I described herein).

Step 2.5:

The Compound 2g is reacted with triflic anhydride and pyridine under an inert atmosphere to obtain compound 2h (wherein $R^3$ and p are as defined in any one of the embodiments of the compound of Formula I described herein).

Step 2.6:

The ethynyl compound 2c obtained in the process step 2.2 was reacted with the compound 2h, which is obtained in process step 2.5, in the presence of copper(I) iodide, LiCl (Lithium chloride), TEA (Triethanolamine), $Pd(PPh_3)_2Cl_2$ (Bis(triphenylphosphine)palladium(II) dichloride) to obtain an ester compound 2i (wherein $R^5$ is hydrogen or methyl; $R^3$ and p are as defined in any one of the embodiments of the compound of Formula I described herein).

Step 2.7:

The compound 2i was hydrolyzed using $LiOH.H_2O$ and a solvent THF:MeOH (4:1) for 24 hours to obtain the corresponding acid compound 2j (wherein $R^1$, $R^2$, $R^3$, p, m and n are as defined in any one of the embodiments of the compound of Formula I described herein).

Step 2.8:

In this process step, the compound 2i was subjected to reduction using Lindlar catalyst and hydrogen to obtain compound 2k (wherein $R^4$ and $R^5$ are hydrogen or methyl;

$R^1$, $R^2$, $R^3$, m and p are as defined in any one of the embodiments of the compound of Formula I described herein).

Step 2.9:

The compound 2k was hydrolyzed using $LiOH.H_2O$ and a solvent mixture such as THF:MeOH (4:1) for 24 hours to obtain compound of formula 2l (wherein $R^4$ and $R^5$ are hydrogen or methyl; $R^1$, $R^2$, $R^3$, m and p are as defined in any one of the embodiments of the compound of Formula I described herein).

Step 2.10:

In this process step, the compound 2k is treated with Pd/C under hydrogen in ethanol to obtain compound (2m) (wherein $R^4$ and $R^5$ are hydrogen or methyl; $R^1$, $R^2$, $R^3$, m and p are as defined in any one of the embodiments of the compound of Formula I described herein).

Step 2.11:

The compound 2m is treated with lithium hydroxide and a solvent mixture such as THF:methanol (4:1) for 24 hours to obtain compound 2n (wherein $R^4$ and $R^5$ are hydrogen or methyl; $R^1$, $R^2$, $R^3$, m and p are as defined in any one of the embodiments of the compound of Formula I described herein).

Scheme 3: Preparation of the compound of Formula I [referred to in Scheme 3 as the compound 3g (wherein $R^1$, $R^2$, $R^3$ and p are as defined in any one of the embodiments of the compound of Formula I described herein)].

Scheme 3

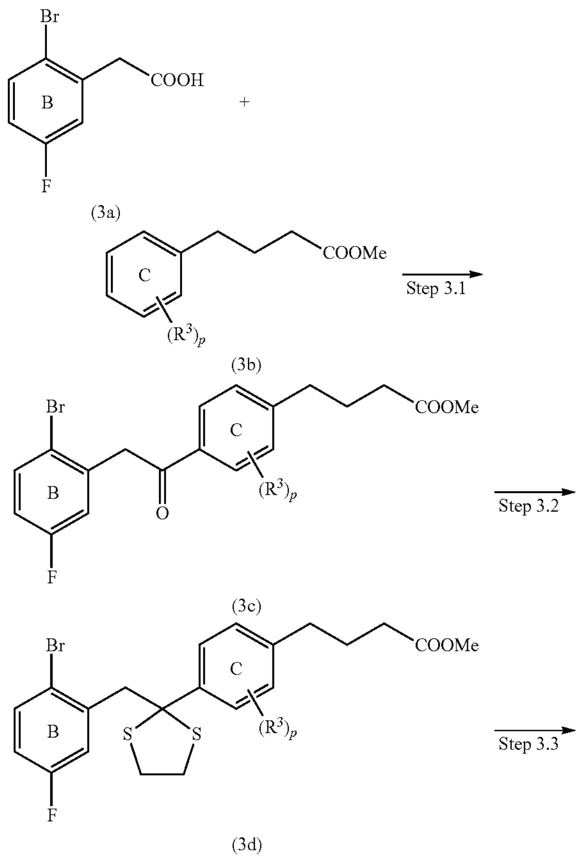

(3a) (3b) (3c) (3d)

-continued

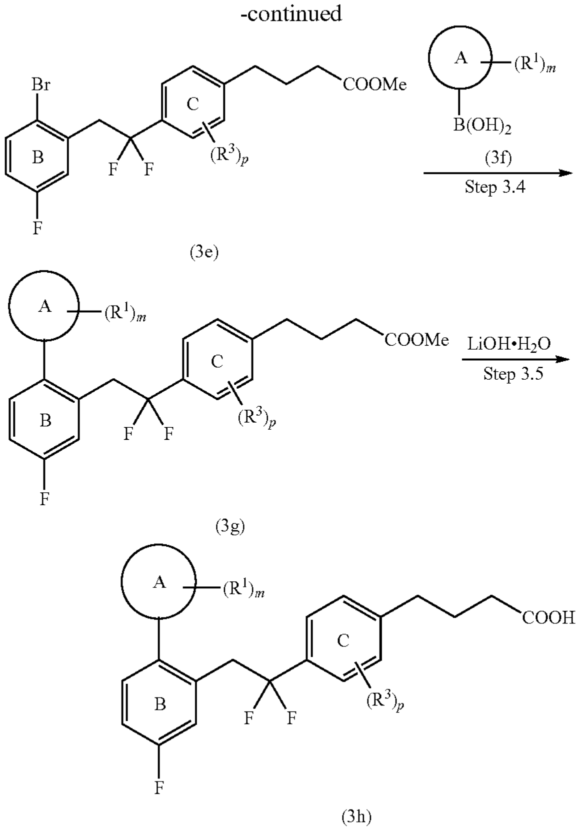

(3e) (3f) (3g) (3h)

Reaction Conditions:

Step 3.1: $AlCl_3$ (Aluminium chloride)

Step 3.2: Ethane-1,3-dithiol, $BF_3$-Etherate (Boron trifluoride diethyl etherate), DCM (dichloromethane), room temperature, overnight.

Step 3.3: 30% HF, Pyridine solution; N-iodosuccinamide, DCM (dichloromethane), −78° C.

Step 3.4: Suzuki coupling: Tetrakis(triphenylphosphine)palladium(0), Sodium bicarbonate, water, dioxane, DMF (Dimethylformamide)

Step 3.5: $LiOH.H_2O$, THF:MeOH (4:1), 6 hours.

Step 3.1:

Compound (3a) is reacted with the compound (3b) (wherein $R^3$ and p are as defined in any one of the embodiments of the compound of Formula I described herein) with $AlCl_3$ (Aluminium chloride) to obtain compound (3c) (wherein $R^3$ and p are as defined for the compound (3b)).

Step 3.2:

The compound (3c) obtained in step 3.1 is treated with ethane-1,2-dithiol, boron trifluoride diethyl etherate and a solvent DCM (dichloromethane) at room temperature for overnight to obtain compound (3d) (wherein $R^3$ and p are as defined for the compound (3b)).

Step 3.3:

The compound (3d) is treated with Olah's Reagent (hydrofluoric acid-pyridine solution), N-iodosuccinamide and a solvent such as DCM (dichloromethane) at −78° C. to obtain compound (3e) (wherein $R^3$ and p are as defined for the compound (3b)).

Step 3.4:

Suzuki coupling reaction of compound (3e) (wherein $R^3$ and p are as defined in any one of the embodiments of the compound of Formula I described herein) with the compound of formula 3f, using tetrakis(triphenylphosphine)

palladium(0), sodium bicarbonate in water and solvent dioxane and DMF (Dimethylformamide) resulted in compound (3g) (wherein $R^1$, $R^3$, m and p are as defined in any one of the embodiments of the compound of Formula I described herein).

Step 3.5:

The compound (3g) is hydrolysed with LiOH and a solvent mixture such as THF:MeOH (4:1) for 6 hours to obtain the compound (3h) (wherein $R^1$, $R^3$ and p are as defined for the compound (3b)).

The compounds of formula (I) encompassed in the present invention as recited in one or more embodiments as described above can be converted into their pharmaceutically acceptable salts by following procedure known to persons skilled in the art.

The pharmaceutically acceptable salt of the compounds of Formula (I) are prepared with relatively non-toxic acids or bases, depending on the particular substituents found on the compound described herein. When the compounds of Formula (I) of the present invention contain an acidic group they can form an addition salt with a suitable base. For example, pharmaceutically acceptable base addition salts of the compounds of the present invention may include their alkali metal salts such as sodium, potassium, calcium, magnesium, ammonium or an organic base addition salt. Examples of pharmaceutically acceptable organic base addition salts of the compounds of the present invention include those derived from organic bases like lysine, arginine, guanidine, diethanolamine, metformin or other organic bases known to the person skilled in the art.

When the compounds of Formula (I) of the present invention contain one or more basic groups, they can form an addition salt with an inorganic or an organic acid. Examples of pharmaceutically acceptable acid addition salts include those derived from inorganic acids like boric acid, perchloric acid, hydrochloric acid, hydrobromic acid, hydrofluoric acid, hydriodic acid, nitric acid, carbonic acid, monohydrogencarbonic acid, phosphoric acid, monohydrogenphosphoric acid, dihydrogenphosphoric acid, sulfuric acid, monohydrogensulfuric acid, phosphorous acids or other inorganic acids known to the person skilled in the art. Furthermore, examples of pharmaceutically acceptable acid addition salts include the salts derived from organic acids such as acetic acid, propionic acid, isobutyric acid, oxalic acid, malic acid acid, tartaric acid, citric acid, ascorbic acid, maleic acid, malonic acid, benzoic acid, succinic acid, suberic acid, fumaric acid, mandelic acid, phthalic acid, benzenesulfonic acid, toluenesulfonic acid, methanesulfonic acid, glucuronic acid, galacturonic acid, naphthoic acid, camphoric acid or other organic acids known to the person skilled in the art. Certain specific compounds of the present invention contain both basic and acidic functionalities that allow the compounds to be converted into either base or acid addition salts.

The pharmaceutically acceptable salts of the present invention can be synthesized from the subject compound i.e. the compound of Formula (I) which contains a basic or acidic moiety by conventional chemical methods. Generally, the salts are prepared by contacting the free base or acid with an appropriate salt-forming inorganic or organic acid or a base in a suitable solvent or dispersant or by anion exchange or cation exchange with other salts. Suitable solvents are, for example, ethyl acetate, ethers, alcohols, acetone, or mixtures of these solvents.

The compounds encompassed in the present invention can be regenerated from their corresponding salts by contacting the said salt with an appropriate base or acid depending on the type of salt and isolating the parent compound in the conventional manner. The corresponding salts of the compounds differ from their parent compounds with respect to certain physical properties, for example solubility.

In an embodiment of the present invention, the compound of Formula (I) or the compound of Formula (IA) or the compound of Formula (IB) or the compound of Formula (IC) is provided as its corresponding pharmaceutically acceptable salt.

Those skilled in the art will recognize that the compounds of Formula (I) of the present invention contain asymmetric or chiral centres, and therefore exist in different stereoisomeric forms, as racemic mixtures of enantiomers, mixtures of diastereomers or enantiomerically or optically pure compounds. The term "chiral" refers to molecules which have the property of non-superimposability of the mirror image cohort, while the term "achiral" refers to molecules which are superimposable on their mirror image partner. It is intended that all stereoisomeric forms of the compounds of the invention, including but not limited to, diastereomers and enantiomers, as well as mixtures thereof such as racemic mixtures, geometric isomers form part of the present invention.

When the compounds of Formula (I) of the present invention contain one chiral centre, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers can be synthesized by asymmetric synthesis using optically active reagents, substrates, catalysts or solvents, or by converting one enantiomer into the other by asymmetric transformation. Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%. When a compound of Formula (I) of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

In one embodiment, the compounds of Formula (I) exist as tautomers, and it is intended to encompass all the tautomeric forms of the compounds within the scope of the present invention.

The present invention furthermore includes all the solvates of the compounds of Formula (I), for example, hydrates and the solvates formed with other solvents of crystallisation, selected from alcohols such as methanol, ethanol, 1-propanol or 2-propanol, ethers such as diethyl ether, isopropyl ether or tetrahydrofuran, esters such as methyl acetate or ethyl acetate, ketone such as acetone or their mixtures thereof. Certain compounds of the present invention can exist in unsolvated forms as well as solvated forms, including hydrated forms.

It is further intended to encompass various polymorphs of the compounds of Formula (I) within the scope of the present invention. Various polymorphs of the compounds of the present invention can be prepared by standard crystallisation procedures known in the art. The crystallisation technique employed can utilize various solvents or their mixtures, temperature conditions and various modes of cooling, ranging from very fast to very slow cooling. The presence of polymorphs can be determined by IR (Infra-red) spectroscopy, solid probe NMR (Nuclear Magnetic Resonance) spectroscopy, differential scanning calorimetry, powder X-ray diffraction or such other standard techniques.

Furthermore, the present invention also includes prodrugs of the compounds of Formula (I). The prodrugs of the compounds of the present invention are derivatives of the aforesaid compounds of the invention which upon administration to a subject in need thereof undergoes chemical conversion by metabolic or chemical processes to release the parent drug in vivo from which the prodrug is derived. The preferred prodrugs are pharmaceutically acceptable ester derivatives e.g., alkyl esters, cycloalkyl esters, alkenyl esters, benzyl esters, mono- or di-substituted alkyl esters convertible by solvolysis under physiological conditions to the parent carboxylic acid, and those conventionally used in the art.

The present invention further relates to carboxylic acid isosteres of the compounds of Formula (I).

The present invention also relates to N-oxide derivatives of the compounds of Formula (I).

The present invention also relates to S-oxide derivatives of the compounds of Formula (I).

In one aspect of the present invention, the compounds of Formula (I) are GPR120 agonists.

In an embodiment of the present invention, the compounds of Formula (I) find use in the treatment or prophylaxis of a disease or a disorder mediated by GPR120.

In another aspect, the present invention relates to a method for the treatment or prophylaxis of a disease or a disorder mediated by GPR120, comprising administering to a subject in need thereof, a therapeutically effective amount of a compound of Formula (I) or a stereoisomer, a tautomer or a pharmaceutically acceptable salt thereof.

In an embodiment, the present invention relates to use of the compound of Formula (I) or a stereoisomer, a tautomer or a pharmaceutically acceptable salt thereof; for the treatment or prophylaxis of a disease or a disorder mediated by GPR120.

According to one embodiment, the present invention relates to use of the compounds of Formula (I) or a stereoisomer, a tautomer or a pharmaceutically acceptable salt thereof; in the manufacture of a medicament for the treatment or prophylaxis of a disease or a disorder mediated by GPR120.

In an embodiment of the invention, the disease or disorder mediated by GPR120 is selected from the group consisting of diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, polycystic ovary syndrome, ketoacidosis, thrombotic disorders, diabetic nephropathy, diabetic neuropathy, diabetic retinopathy, sexual dysfunction, fatty liver development, dermatopathy, dyspepsia, hypoglycemia, cancer, edema, pancreatic beta cell degeneration, and a disorder associated with pancreatic beta cell degeneration.

In an embodiment of the invention, the disease or disorder mediated by GPR120 is selected from the group consisting of diabetes, obesity, insulin resistance, hyperglycemia, glucose intolerance, hypercholesterolemia, hypertriglylceridemia, dyslipidemia, hyperlipoproteinemia, hyperinsulinemia, atherosclerosis, diabetic nephropathy, diabetic neuropathy, diabetic retinopathy, metabolic syndrome, syndrome X, hypertension and pancreatic beta cell degeneration.

In an embodiment of the invention, the disease or disorder mediated by GPR120 is selected from the group consisting of diabetes, obesity, insulin resistance, hyperglycemia, glucose intolerance, metabolic syndrome, syndrome X and pancreatic beta cell degeneration.

In an embodiment, diabetes is Type 2 diabetes.

In an embodiment, the disease or disorder mediated by GPR120 is a metabolic disorder which refers to one or more diseases or disorders as identified above.

In an embodiment, the disease or disorder mediated by GPR120 is an inflammatory disorder.

Accordingly, the present invention relates to a method for the treatment or prophylaxis of a metabolic disorder, comprising administering to a subject in need thereof a therapeutically amount of a compound of Formula (I) or a stereoisomer, a tautomer or a pharmaceutically acceptable salt thereof.

In an embodiment, the present invention provides use of the compound of Formula (I) or a stereoisomer, a tautomer or a pharmaceutically acceptable salt thereof; for the treatment or prophylaxis of a metabolic disorder.

According to one embodiment, the present invention relates to use of the compound of Formula (I) or a pharmaceutically acceptable salt thereof in the manufacture of a medicament, for the treatment or prophylaxis of a metabolic disorder.

In one embodiment, the metabolic disorder is selected from the group consisting of diabetes, obesity, cardiovascular disease, hypertension, ketoacidosis, insulin resistance, glucose intolerance, hyperglycemia, hypertriglylceridemia, polycystic ovary syndrome, hypercholesterolemia, hyperlipoproteinemia, dyslipidemia, metabolic syndrome, syndrome X, hyperlipidemia, diabetic nephropathy, diabetic neuropathy, diabetic retinopathy, edema and related disorders associated with abnormal plasma lipoprotein, triglycerides, pancreatic beta cell degeneration; and a disorder associated with pancreatic beta cell degeneration.

In an embodiment, the metabolic disorder is selected from the group consisting of diabetes, obesity, insulin resistance, hyperglycemia, glucose intolerance, hypercholesterolemia, hypertriglylceridemia, dyslipidemia, hyperlipoproteinemia, hyperinsulinemia, atherosclerosis, diabetic nephropathy, diabetic neuropathy, diabetic retinopathy, metabolic syndrome, syndrome X, hypertension and pancreatic beta cell degeneration.

In an embodiment, the metabolic disorder is selected from the group consisting of diabetes, obesity, insulin resistance, glucose intolerance, dyslipidemia, hyperinsulinemia, syndrome X, metabolic syndrome and pancreatic beta cell degeneration.

In an embodiment, the metabolic disorder is Type 2 diabetes.

The present invention furthermore relates to pharmaceutical compositions that contain a therapeutically effective amount of at least one compound of Formula (I) or its pharmaceutically acceptable salt in addition to a customary pharmaceutically acceptable carrier, and to a process for the production of a pharmaceutical composition, which includes bringing at least one compound of Formula (I), into a suitable administration form using a pharmaceutically suitable and physiologically tolerable excipient and, if appropriate, further additives or auxiliaries.

According to one embodiment, the present invention relates to a pharmaceutical composition comprising the compound of Formula (I) or a pharmaceutically acceptable salt thereof; and one or more pharmaceutically acceptable excipients; for use in the treatment or prophylaxis of a disease or a disorder mediated by GPR120.

It is further intended to include within the scope of the present invention the use of the compounds of Formula (I) or its pharmaceutically acceptable salts thereof in combination with at least one further therapeutically active agent.

According to one embodiment, the present invention provides a pharmaceutical composition, comprising a therapeutically effective amount of a compound of Formula (I) or a pharmaceutically acceptable salt thereof; and at least one further therapeutically active agent, together with a pharmaceutically acceptable excipient.

In an embodiment, the present invention relates to use of the compound of Formula (I) or a pharmaceutically acceptable salt thereof; in combination with a further therapeutically active compound, in the treatment or prophylaxis of a disease or a disorder mediated by GPR120.

The therapeutically active agent used in combination with one or more of the compounds of Formula (I) can be selected from the compounds or therapeutically active substances known to be used in the treatment of diabetes and other conditions/disorders such as obesity, insulin resistance, hyperglycemia, glucose intolerance, hypercholesterolemia, hypertriglylceridemia, dyslipidemia, hyperlipoproteinemia, hyperinsulinemia or atherosclerosis. According to the present invention, the therapeutically active agent, used in combination with the compounds of Formula (I) of the present invention can be selected from, but not limited to, insulin, sulfonylureas, biguanidines, meglitinides, oxadiazolidinediones, thiazolidinediones, glucosidase inhibitors, inhibitors of glycogen phosphorylase, glucagon antagonists, HMGCoA reductase inhibitor, GLP-1 (Glucogen-like peptide-1) agonists, potassium channel openers, inhibitors of dipeptidylpeptidase IV (DPP-IV), diglyceride acyltransferase (DGAT) inhibitor, insulin sensitizers, modulators of glucose uptake, modulators of glucose transport and modulators of glucose reabsorption, modulators of the sodium-dependent glucose transporter 1 or 2 (SGLT1, SGLT2), compounds which alter lipid metabolism such as antihyperlipidemic active ingredients and antilipidemic active ingredients, PPARgamma agonists and agents with combined PPARalpha and gamma activity and active ingredients which act on the ATP-dependent potassium channel of the beta cells.

In an embodiment, the compound of Formula (I) can be used in combination with a PPAR gamma agonist selected from rosiglitazone, pioglitazone, rivoglitazone, and the like.

In an embodiment, the compound of Formula (I) can be used in combination with a HMGCoA reductase inhibitor selected from simvastatin, fluvastatin, pravastatin, lovastatin, atorvastatin, cerivastatin, rosuvastatin, and the like.

In an embodiment, the compound of Formula (I) can be used in combination with a sulfonylurea selected from tolbutamide, glibenclamide, glipizide, glimepiride, and the like.

In another embodiment, the compound of the Formula (I) can be used in combination with a meglitinide selected from repaglinide, nateglinide, mitiglinide, and the like.

In another embodiment, the compound of the Formula (I) can be used in combination with GLP-1 agonist selected from exenatide, liraglutide, taspoglutide albiglutide, lixisenatide, and the like.

In another embodiment, the compound of the Formula (I) can be used in combination with DPP-IV inhibitor selected from alogliptin, gemigliptin, linagliptin, saxagliptin, sitagliptin, vildagliptin, and the like.

Accordingly, in an embodiment the further therapeutically active agent that can be used in combination with one or more compounds of Formula (I) encompassed in the present invention, can be selected from one or more of the agents including, but not limited to, insulin, rosiglitazone, pioglitazone, rivoglitazone, simvastatin, fluvastatin, pravastatin, lovastatin, atorvastatin, cerivastatin, rosuvastatin, tolbutamide, glibenclamide, glipizide, glimepiride, repaglinide, nateglinide, mitiglinide, exenatide, liraglutide, taspoglutide albiglutide, lixisenatide, alogliptin, gemigliptin, linagliptin, saxagliptin, sitagliptin, vildagliptin, and the like.

The pharmaceutical compositions according to the present invention are prepared in a manner known and familiar to one skilled in the art. Pharmaceutically acceptable inert inorganic and/or organic carriers and/or additives can be used in addition to the compound of Formula (I) and/or its pharmaceutically acceptable salts. For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

Further, the pharmaceutical composition of the present invention can also contain additives such as fillers, antioxidants, emulsifiers, preservatives, flavours, solubilisers or colourants. The pharmaceutical composition of the present invention may also contain two or more compounds of Formula (I) and/or its pharmaceutically acceptable salts, the pharmaceutical compositions can also contain one or more other therapeutically or prophylactically active ingredients.

The pharmaceutical compositions normally contain about 1 to 99%, for example, about 10 to 80%, by weight of the compounds of Formula (I) or their pharmaceutically acceptable salts.

The amount of the active ingredient i.e. the compound of Formula (I) or its pharmaceutically acceptable salt in the pharmaceutical compositions can, for example, vary from about 1 to 500 mg. In case of higher body weight of the mammal in need of the treatment, the pharmaceutical composition may contain the compound of Formula (I) or its pharmaceutically acceptable salt in an amount ranging from 5 mg to 1000 mg. The desirable dosage of the compounds of Formula (I) or its pharmaceutically acceptable salt can be selected over a wide range. The daily dosage to be administered is selected to achieve the desired therapeutic effect in subjects being treated for metabolic disorders. A dosage of about 0.05 to 50 mg/kg/day of the compounds of Formula (I) or its pharmaceutically acceptable salt may be administered. In case of higher body weight of the mammal in need of the treatment, a dosage of about 0.1 to 100 mg/kg/day of the compound of Formula (I) or its pharmaceutically acceptable salt may be administered. If required, higher or lower daily dosages can also be administered. Actual dosage levels of the active ingredients in the pharmaceutical composition of this present invention can be varied so as to obtain an amount of the active ingredient, which is effective to achieve the desired therapeutic response for a particular patient (subject), composition, and mode of administration without being toxic to the patient. The selected dosage level can be readily determined by a skilled medical practitioner in the light of the relevant circumstances, including the condition (diseases or disorder) to be treated, the chosen route of administration depending on a number of factors, such as age, weight and physical health and response of the individual patient, pharmacokinetics, severity of the disease and the like, factors known in the medical art.

The pharmaceutical compositions according to the present invention can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

It is understood that modifications that do not substantially affect the activity of the various embodiments of this invention are included within scope of the invention disclosed herein. Accordingly, the following examples are intended to illustrate but not to limit scope of the present invention.

EXPERIMENTAL

Nomenclature of the compounds exemplified in the present invention was derived from Chemdraw Ultra version 9.0.1 CambridgeSoft Corporation, Cambridge.

Reagents were purchased from commercial suppliers such as Combi-Blocks Inc., CA; and CombiPhos Catalysts, Inc; and were used as such.

Unless otherwise stated all temperatures are in degree celsius. Also, in these examples and elsewhere, abbreviations have the following meanings:

The abbreviations and terms that are used herein:

LIST OF ABBREVIATIONS

| | | | |
|---|---|---|---|
| Pd/C | Palladium on carbon | mmole | Millimoles |
| $CDCl_3$ | Deuterated chloroform | mL | Millilitre |
| ° C. | Degree celcius | nM | Nanomolar |
| DMF | N,N-dimethyl formamide | DMSO-$d_6$ | Deuterated dimethylsulfoxide |
| DMSO | Dimethyl sulfoxide | DCM | Dichloromethane |
| g | gram | μM | Micromolar |
| $LiOH{\bullet}H_2O$ | Lithium hydroxide monohydrate | $Pd(PPh_3)_2Cl_2$ | Bis(triphenylphosphine) palladium(II) dichloride |
| mg | milligram | RT | Room temperature |
| MeOH | Methanol | PET | Petroleum ether |
| mM | Millimolar | THF | Tetrahydrofuran |
| PEPPSI-IPr catalyst | [1,3-Bis(2,6-diisopropylphenyl)imidazol-2-ylidene](3-chloropyridyl) palladium(II) dichloride | | |

Example 1

4-(5-((5-Fluoro-2-(6-methoxypyridin-3-yl)phenyl) ethynyl)pyridin-2-yl)butanoic acid (Compound 1)

Step 1a

Synthesis of 5-(benzyloxy)-2-bromopyridine

To 6-bromopyridin-3-ol (10 g, 57.5 mmol) and cesium carbonate (28.1 g, 86 mmol) in acetonitrile (50 mL), benzyl bromide (8.20 mL, 69.0 mmol) was added and the reaction mass was allowed to stir at room temperature overnight. The reaction mass was quenched with water and extracted with ethyl acetate (2×100 mL), organic layer was dried over sodium sulphate and concentrated to give crude mass which was purified using column chromatography to provide 5-(benzyloxy)-2-bromopyridine (12.3 g, 46.1 mmol, 80% yield).

$^1H$ NMR (300 MHz, $CDCl_3$): δ 8.19 (d, J=1.5 Hz, 1H), 7.55 (d, J=8.7 Hz, 1H), 7.47-7.32 (m, 6H), 5.18 (s, 2H); LCMS (m/z): 265 (M+1).

Step 1b

Synthesis of ethyl 4-(5-(benzyloxy)pyridin-2-yl)butanoate 5-(Benzyloxy)-2-bromopyridine (6 g, 22.72 mmol) was stirred in dry THF (20 mL) under argon atmosphere. (4-Ethoxy-4-oxobutyl)zinc(II) bromide (50.0 mL, 24.99 mmol) in THF was added carefully under argon atmosphere followed by [1,3-bis(2,6-diisopropylphenyl)imidazol-2-ylidene](3-chloropyridyl)palladium(II) dichloride (Peppsi catalyst) (0.772 g, 1.136 mmol) and reaction stirred at room temperature overnight. Reaction mixture was quenched with saturated solution of ammonium chloride and extracted with ethyl acetate (2×25 mL). Organic layer was washed with brine (25 mL), dried and concentrated to obtain crude which was purified using column chromatography to provide ethyl 4-(5-(benzyloxy)pyridin-2-yl)butanoate. (4.3 g, 14.23 mmol, 62.6% yield).

$^1$H NMR (300 MHz, $CDCl_3$): δ 8.25 (d, J=3.0 Hz, 1H), 7.46-7.31 (m, 6H), 7.16 (d, J=8.4 Hz, 1H), 5.14 (s, 2H), 4.03 (q, J=6.9 Hz, 2H), 2.82 (t, J=7.2 Hz, 2H), 2.66 (t, J=7.2 Hz, 2H), 1.93-1.83 (m, 2H), 1.19 (t, J=6.9 Hz, 3H); LCMS (m/z): 300.1 (M+1).

Step 1c

Synthesis of ethyl 4-(5-hydroxypyridin-2-yl)butanoate

To a solution of ethyl 4-(5-(benzyloxy)pyridin-2-yl)butanoate (4.2 g, 14.03 mmol) in ethanol (25 mL), Pd/C (0.149 g, 1.403 mmol) was added and the flask was shaken under hydrogen atmosphere at 40 psi for 4 hours. After completion of the reaction, it was filtered through celite and concentrated to provide ethyl 4-(5-hydroxypyridin-2-yl)butanoate. (2.7 g, 12.79 mmol, 91% yield).

$^1$H NMR (300 MHz, $CDCl_3$): δ 9.7 (s, 1H), 8.02 (d, J=2.1 Hz, 1H), 7.08-7.01 (m, 2H), 4.03 (q, J=6.0 Hz, 2H), 2.61 (t, J=7.5 Hz, 2H), 2.27 (t, J=7.5 Hz, 2H), 1.90-1.30 (m, 2H), 1.19 (t, J=6.9 Hz, 3H); MS (m/z): 210.1 (M+1).

Step 1d

Synthesis of ethyl 4-(5-(((trifluoromethyl)sulfonyl)oxy)pyridin-2-yl)butanoate To a solution of ethyl 4-(5-hydroxypyridin-2-yl)butanoate (250 mg, 1.195 mmol) in DCM (10 mL) was added pyridine (0.773 mL, 9.56 mmol), triflic anhydride (0.505 mL, 2.99 mmol) under nitrogen atmosphere and allowed to stir overnight. After completion of reaction, the reaction mass was concentrated and purified using column chromatography to provide ethyl 4-(5-(((trifluoromethyl)sulfonyl)oxy)pyridin-2-yl)butanoate. (0.315 g, 0.917 mmol, 77% yield).

$^1$H NMR (300 MHz, $CDCl_3$): δ 8.68 (d, J=2.7 Hz, 1H), 7.95 (dd, J=3.0 Hz, J=5.7 Hz, 1H), 7.48 (d, J=7.2 Hz, 1H), 4.07 (q, J=7.2 Hz, 2H), 2.82 (t, J=5.7 Hz, 2H), 2.33 (t, J=7.5 Hz, 2H), 1.93 (m, 2H), 1.71 (t, J=6.9 Hz, 3H); MS (m/z): 342.1 (M+1).

Step 1e

Synthesis of 5-fluoro-2-(6-methoxypyridin-3-yl)benzaldehyde

2-Bromo-5-fluorobenzaldehyde (2 g, 9.85 mmol) was added to a stirred solution of (6-methoxypyridin-3-yl)boronic acid (1.808 g, 11.82 mmol), sodium bicarbonate (1.655 g, 19.70 mmol) in 1,4-dioxane:water (16 mL:4 mL). The reaction mass was degassed and flushed with nitrogen, tetrakis(triphenylphosphine)palladium(0) (1.138 g, 0.985 mmol) was then added. It was flushed with nitrogen and stirred at 111° C. for 3 hours. Reaction mixture was cooled, diluted with water and extracted with ethyl acetate (2×25 mL).

Ethyl acetate layer was washed with brine (25 mL), dried over sodium sulphate and concentrated to get crude. The crude obtained was purified by column chromatography to provide 5-fluoro-2-(6-methoxypyridin-3-yl)benzaldehyde. (1.7 g, 7.35 mmol, 74.6% yield).

$^1$H NMR (300 MHz, $CDCl_3$): δ 9.85 (d, J=3.0 Hz, 1H), 8.23 (d, J=2.1 Hz, 1H), 7.84 (dd, J=2.4 Hz, J=6.3 Hz, 1H), 7.69-7.57 (m, 3H), 6.95 (d, J=8.4 Hz, 1H), 3.92 (s, 3H); MS (m/z): 232.1 (M+1).

Step 1f

Synthesis of 5-(2-ethynyl-4-fluorophenyl)-2-methoxypyridine

Dimethyl (1-diazo-2-oxopropyl)phosphonate (1.246 mL, 0.519 mmol) was added dropwise to a solution of 5-fluoro-2-(6-methoxypyridin-3-yl)benzaldehyde (100 mg, 0.432 mmol) and potassium carbonate (120 mg, 0.865 mmol) in dry methanol (5 mL) at room temperature under argon, and the mixture was stirred at room temperature for 15 minutes. The reaction was quenched with brine (15 mL), and the mixture was extracted with ethyl acetate (2×25 mL). The combined organic layer was washed with brine (30 mL), dried over $Na_2SO_4$. Solvent was removed under reduced pressure and the crude obtained was purified by column chromatography to provide 5-(2-ethynyl-4-fluorophenyl)-2-methoxypyridine. (0.071 g, 0.309 mmol, 75.1% yield).

$^1$H NMR (300 MHz, $CDCl_3$): δ 8.31 (d, J=2.1 Hz, 1H), 7.88 (dd, J=2.4 Hz, J=6.0 Hz, 1H), 7.51-7.46 (m, 2H), 7.40-7.57 (m, 1H), 6.90 (d, J=8.7 Hz, 1H), 4.33 (s, 1H), 3.90 (s, 3H); MS (m/z): 228.0 (M+1).

Step 1g

Synthesis of ethyl 4-(5-((5-fluoro-2-(6-methoxypyridin-3-yl)phenyl)ethynyl)pyridin-2-yl)butanoate To a solution of ethyl 4-(5-(((trifluoromethyl)sulfonyl)oxy)pyridin-2-yl)butanoate (50 mg, 0.146 mmol), 5-(2-ethynyl-4-fluorophenyl)-2-methoxypyridine (56.6 mg, 0.249 mmol), lithium chloride (9.32 mg, 0.220 mmol), copper (I) iodide (1.395 mg, 7.32 μmol), triethanolamine (0.306 mL, 2.197 mmol) in DMF (2 mL) was added bis(triphenylphosphine)palladium(II) chloride (2.057 mg, 2.93 μmol) under nitrogen atmosphere. The reaction vessel was degassed, flushed with nitrogen and heated at 60° C. overnight. The reaction mass was distilled off and the crude was purified using column chromatography to provide ethyl 4-(5-((5-fluoro-2-(6-methoxypyridin-3-yl)phenyl)ethynyl)pyridin-2-yl)butanoate. (0.053 g, 0.124 mmol, 84% yield).

$^1$H NMR (300 MHz, $CDCl_3$): δ 8.52 (s, 1H), 8.36 (d, J=2.1 Hz, 1H), 7.88 (dd, J=2.4 Hz, J=6.3 Hz, 1H), 7.57 (dd, J=1.8 Hz, J=6.0 Hz, 1H), 7.39-7.35 (m, 2H), 7.19-7.12 (m, 2H), 6.85 (d, J=8.4 Hz, 1H), 4.14 (q, J=7.2 Hz, 2H), 4.01 (s, 3H), 2.85 (t, J=7.5 Hz, 2H), 2.36 (t, J=7.5 Hz, 2H), 2.12-2.02 (m, 2H), 1.27 (t, J=7.2 Hz, 3H); MS (m/z): 419.1 (M+1).

Step 1h

Synthesis of 4-(5-((5-fluoro-2-(6-methoxypyridin-3-yl)phenyl)ethynyl)pyridin-2-yl)butanoic acid To a solution of ethyl 4-(5-((5-fluoro-2-(6-methoxypyridin-3-yl)phenyl)ethynyl)pyridin-2-yl)butanoate (50 mg, 0.119 mmol) in THF (4 mL), methanol (1.0 mL) was added LiOH (17.17 mg, 0.717 mmol) and allowed to stir at RT overnight. The reaction mass was distilled under vacuum, quenched with water (25 mL) and brine (25 mL) and extracted with ethyl acetate (2×25 mL). Combined organic layer was dried over sodium sulphate and concentrated to provide 4-(5-((5-fluoro-2-(6-methoxypyridin-3-yl)phenyl)ethynyl)pyridin-2-yl)butanoic acid. (0.032 g, 0.082 mmol, 68.5% yield).

$^1H$ NMR (300 MHz, $CDCl_3$): δ 12.09 (s, 1H), 8.48 (s, 1H), 8.37 (d, J=2.1 Hz, 1H), 8.03 (dd, J=2.4 Hz, J=6.3 Hz, 1H), 7.70 (dd, J=2.1 Hz, J=6.0 Hz, 1H), 7.59-7.54 (m, 2H), 7.43-7.38 (m, 1H), 7.31 (d, J=8.1 Hz, 1H), 6.96 (d, J=6.7 Hz, 1H), 3.91 (s, 3H), 2.76 (t, J=7.5 Hz, 2H), 2.23 (t, J=7.5 Hz, 2H), 1.90-1.88 (m, 2H); MS (m/z): 391.1 (M+1).

Example 2

4-(5-(5-Fluoro-2-(6-methoxypyridin-3-yl)phenethyl)pyridin-2-yl)butanoic acid (Compound 2)

Step 2a

Synthesis of ethyl 4-(5-(5-fluoro-2-(6-methoxypyridin-3-yl)phenethyl)pyridin-2-yl)butanoate To a solution of ethyl 4-(5-((5-fluoro-2-(6-methoxypyridin-3-yl)phenyl)ethynyl)pyridin-2-yl)butanoate (70 mg, 0.167 mmol) in ethanol (25 mL), Pd/C (1.780 mg, 0.017 mmol) was added and the flask was stirred under hydrogen atmosphere at RT overnight. After completion of reaction, reaction mixture was filtered through celite and concentrated to provide ethyl 4-(5-(5-fluoro-2-(6-methoxypyridin-3-yl)phenethyl)pyridin-2-yl)butanoate. (0.060 g, 0.137 mmol, 82% yield).

$^1H$ NMR (300 MHz, $CDCl_3$): δ 8.08 (s, 1H), 8.01 (d, J=1.8 Hz, 1H), 7.59 (dd, J=2.4 Hz, J=6.3 Hz, 1H), 7.30-7.06 (m, 5H), 6.86 (d, J=9.0 Hz, 1H), 4.02 (q, J=9.0 Hz, 2H), 3.89 (s, 3H), 2.86-2.61 (m, 6H), 2.28 (t, J=6.0 Hz, 2H), 1.91-1.82 (m, 2H), 1.16 (t, J=6.0 Hz, 3H); MS (m/z): 423.1 (M+1).

Step 2b

Synthesis of 4-(5-(5-fluoro-2-(6-methoxypyridin-3-yl)phenethyl)pyridin-2-yl)butanoic acid The title compound was prepared in an analogous manner as the compound of Step 1h of Example 1, by using ethyl 4-(5-(5-fluoro-2-(6-methoxypyridin-3-yl)phenethyl)pyridin-2-yl)butanoate (50 mg, 0.118 mmol) instead of ethyl 4-(5-((5-fluoro-2-(6-methoxypyridin-3-yl)phenyl)ethynyl)pyridin-2-yl)butanoate to obtain 4-(5-(5-fluoro-2-(6-methoxypyridin-3-yl)phenethyl)pyridin-2-yl)butanoic acid. (0.015 g, 0.036 mmol, 30.2% yield).

$^1H$ NMR ($CDCl_3$, 300 MHz): δ 8.16 (s, 1H), 7.96 (s, 1H), 7.42 (dd, J=2.4 Hz, J=6.0 Hz, 1H), 7.25 (s, 1H), 7.17-7.09 (m, 2H), 7.01 (d, J=6.0 Hz, 2H), 6.80 (s, 1H), 3.99 (s, 3H), 2.95-2.73 (m, 6H), 2.40 (t, J=6.0 Hz, 2H), 2.07 (t, J=6.0 Hz, 2H), 1.26 (t, J=3.0 Hz, 2H); MS (m/z): 395.2 (M+1).

Example 3

4-(5-((5-Fluoro-2-(5-methylthiophen-2-yl)phenyl)ethynyl)pyridin-2-yl)butanoic acid (Compound 3)

Step 3a

Synthesis of 5-fluoro-2-(5-methylthiophen-2-yl)benzaldehyde

2-Bromo-5-fluorobenzaldehyde (1 g, 4.93 mmol) was added to a stirred solution of 4,4,5,5-tetramethyl-2-(5-methylthiophen-2-yl)-1,3,2-dioxaborolane (1.987 g, 8.87 mmol) and sodium bicarbonate (0.828 g, 9.85 mmol) in 20 mL of 1,4-Dioxane:water (4:1). The reaction mass was degassed and flushed with nitrogen. Tetrakis(triphenylphosphine)palladium(0) (0.569 g, 0.493 mmol) was added to it and stirred at 111° C. for 3 hours. Reaction mixture was cooled, diluted with water and extracted with ethyl acetate (2×25 mL). The organic layer was washed with water (25 mL), brine (25 mL) and dried over sodium sulphate to obtain crude which was purified by column chromatography to provide 5-fluoro-2-(5-methylthiophen-2-yl)benzaldehyde. (0.650 g, 2.82 mmol, 57.2% yield).

$^1H$ NMR (300 MHz, $CDCl_3$): δ 10.04 (d, J=3.3 Hz, 1H), 7.66-7.57 (m, 3H), 7.05 (d, J=3.3 Hz, 1H), 6.91 (d, J=2.4 Hz, 1H), 2.51 (s, 3H); MS (m/z): 221 (M+1).

Step 3b

Synthesis of 2-(2-ethynyl-4-fluorophenyl)-5-methylthiophene

Dimethyl (1-diazo-2-oxopropyl)phosphonate (2.62 mL, 1.090 mmol) was added dropwise to a solution of 5-fluoro-2-(5-methylthiophen-2-yl)benzaldehyde (200 mg, 0.908 mmol) and potassium carbonate (251 mg, 1.816 mmol) in dry methanol (2 mL) at RT under argon, and the mixture was stirred at room temperature for 15 minutes. The reaction was quenched with brine (15 mL), and the mixture extracted with ethyl acetate (2×25 mL). The combined organic layer was washed with brine (30 mL), dried over $Na_2SO_4$. Solvent was removed under reduced pressure and crude residue was purified by column chromatography to provide 2-(2-ethynyl-4-fluorophenyl)-5-methylthiophene. (0.143 g, 0.658 mmol, 72.5% yield).

$^1H$ NMR ($CDCl_3$, 300 MHz): δ 7.58-7.54 (m, 1H), 7.42 (dd, J=6.6 Hz, J=2.7 Hz, 1H), 7.31-7.27 (m, 2H), 6.83 (d, J=2.7 Hz, 1H), 4.52 (s, 1H), 2.51 (s, 3H); MS (m/z): 217 (M+1).

Step 3c

Synthesis of ethyl 4-(5-((5-fluoro-2-(5-methylthiophen-2-yl)phenyl)ethynyl)pyridin-2-yl)butanoate To a solution of ethyl 4-(5-(((trifluoromethyl)sulfonyl)oxy)pyridin-2-yl)butanoate (50 mg, 0.146 mmol), 2-(2-ethynyl-4-fluorophenyl)-5-methylthiophene (53.9 mg, 0.249 mmol), lithium chloride (9.32 mg, 0.220 mmol), copper(I) iodide (1.395 mg, 7.32 μmol), triethylamine (0.306 mL, 2.197 mmol) in dimethylformamide (2 mL), bis(triphenylphosphine)palladium(II) chloride (2.057 mg, 2.93 μmol) was added under nitrogen atmosphere. The reaction vessel was degassed and flushed with nitrogen and heated at 60° C. overnight. The reaction mass was distilled off and the crude was purified using column chromatography to provide ethyl 4-(5-((5-fluoro-2-(5-methylthiophen-2-yl)phenyl)ethynyl)pyridin-2-yl)butanoate. (0.055 g, 0.131 mmol, 89.0% yield).

$^1H$ NMR (300 MHz, $CDCl_3$): δ 8.66 (s, 1H), 8.04 (s, 1H), 7.70 (dd, J=6.0 Hz, J=2.1 Hz, 1H), 7.51 (q, J=5.7 Hz, 1H), 7.33 (d, J=3.9 Hz, 1H), 7.18 (d, J=8.1 Hz, 1H), 7.12-7.05 (m, 1H), 6.78 (d, J=3.6 Hz, 1H), 4.15 (q, J=7.2 Hz, 2H), 2.86 (d, J=7.8 Hz, 2H), 2.55 (s, 3H), 2.39 (t, J=7.5 Hz, 2H), 2.15-2.05 (m, 2H), 1.28 (t, J=7.2 Hz, 3H); HPLC (%): 96.81%; MS (m/z): 408.1 (M+1).

Step 3d

Synthesis of 4-(5-((5-fluoro-2-(5-methylthiophen-2-yl)phenyl)ethynyl)pyridin-2-yl)butanoic acid To a solution of ethyl 4-(5-((5-fluoro-2-(5-methylthiophen-2-yl)phenyl)ethynyl)pyridin-2-yl)butanoate (40 mg, 0.098 mmol) in THF (4 mL) and methanol (1.0 mL), LiOH (14.10 mg, 0.589 mmol) was added and allowed to stir at RT overnight. The reaction mass was concentrated under vacuum, quenched with water (25 mL) and brine (25 mL) and extracted with ethyl acetate (2×25 mL). Combined organic layer was dried over sodium sulphate and concentrated to provide 4-(5-((5-fluoro-2-(5-methylthiophen-2-yl) phenyl)ethynyl)pyridin-2-yl)butanoic acid. (0.011 g, 0.029 mmol, 29.5% yield).

$^1$H NMR (300 MHz, $CDCl_3$): δ 12.05 (s, 1H), 8.64 (s, 1H), 7.86 (dd, J=2.7 Hz, J=6.0 Hz, 1H), 7.67 (q, J=5.7 Hz, 1H), 7.53 (q, J=6.0 Hz, 1H), 7.44 (d, J=3.6 Hz, 1H), 7.37-7.32 (m, 2H), 6.88 (d, J=2.7 Hz, 1H), 3.81 (s, 3H), 2.79 (t, J=7.2 Hz, 2H), 2.26 (t, J=7.2 Hz, 2H), 1.99-1.88 (s, 2H); MS (m/z): 380.1 (M+1).

Example 4

4-(5-(5-Fluoro-2-(5-methylthiophen-2-yl)phenethyl) pyridin-2-yl)butanoic acid (Compound 4)

Step 4a

Synthesis of ethyl 4-(5-(5-fluoro-2-(5-methylthiophen-2-yl)phenethyl)pyridin-2-yl)butanoate To a solution of ethyl 4-(5-((5-fluoro-2-(5-methylthiophen-2-yl)phenyl)ethynyl)pyridin-2-yl)butanoate (45 mg, 0.110 mmol) in ethanol (25 mL), Pd/C (1.175 mg, 0.011 mmol) was added and the flask was shaken under hydrogen atmosphere at RT overnight. After completion of reaction, it was filtered through celite and concentrated to provide ethyl 4-(5-(5-fluoro-2-(5-methylthiophen-2-yl)phenethyl)pyridin-2-yl)butanoate. (0.040 g, 0.095 mmol, 86% yield).

$^1$H NMR (300 MHz, $CDCl_3$): δ 8.27 (s, 1H), 7.43-7.42 (m, 1H), 7.34-7.31 (m, 1H), 7.20 (d, J=7.8 Hz, 1H), 6.96-6.63 (m, 2H), 6.73-6.71 (m, 2H), 4.14 (q, J=7.2 Hz, 2H), 3.06-2.80 (m, 6H), 2.54 (s, 3H), 2.39 (t, J=7.5 Hz, 2H), 2.12-2.07 (m, 2H), 1.27 (t, J=7.2 Hz, 3H); MS (m/z): 411.5 (M+1).

Step 4b

Synthesis of 4-(5-(5-fluoro-2-(5-methylthiophen-2-yl)phenethyl)pyridin-2-yl)butanoic acid To a solution of ethyl 4-(5-(5-fluoro-2-(5-methylthiophen-2-yl)phenethyl)pyridin-2-yl)butanoate (35 mg, 0.085 mmol) in THF (4 mL) and methanol (1.000 mL) was added LiOH (12.22 mg, 0.510 mmol) and allowed to stir at RT overnight. The reaction mass was distilled under vacuum, quenched with water (10 mL) and brine (10 mL) and extracted with ethyl acetate (2×25 mL). Combined organic layer was dried over sodium sulphate and concentrated to provide 4-(5-(5-fluoro-2-(5-methylthiophen-2-yl)phenethyl)pyridin-2-yl)butanoic acid. (0.021 g, 0.054 mmol, 63.4% yield).

$^1$H NMR (300 MHz, $CDCl_3$): δ 8.22 (s, 1H), 7.29-7.28 (m, 2H), 7.15 (d, J=8.1 Hz, 1H), 6.93 (d, J=8.7 Hz, 2H), 6.73 (s, 2H), 3.04-2.95 (m, 4H), 2.82 (t, J=8.7 Hz, 2H), 2.41 (t, J=8.2 Hz, 2H), 2.07 (s, 3H), 1.25-1.27 (m, 2H); MS (m/z): 384.3 (M+1).

Example 5

4-(4-(1,1-Difluoro-2-(5-fluoro-2-(5-methylthiophen-2-yl)phenyl)ethyl)phenyl)butanoic acid (Compound 5)

Step 5a

Synthesis of 2-(3-bromophenyl)acetyl chloride

To a solution 2-(3-bromophenyl)acetic acid (3.5 g, 16.28 mmol) in THF (20 mL), catalytic dimethylformamide was added followed by addition of oxalyl chloride (1.396 mL, 16.28 mmol), the reaction mixture was allowed to stir for 2 hours followed by concentration under reduced pressure to provide 2-(3-bromophenyl)acetyl chloride as yellow oil (3.6 g, 15.42 mmol, 95% yield).

Step 5b

Synthesis of methyl 4-(4-(2-(2-bromo-5-fluorophenyl)acetyl)phenyl)butanoate

To a solution of methyl 4-phenylbutanoate (2.2 g, 12.34 mmol) in anhydrous 1-ethyl-3-(3-dimethylaminopropyl)carbodiimide (10 ml), Aluminium chloride (1.975 g, 14.81 mmol) was added at −30° C. {obtained with dry ice and excess of ethyl acetate}. Reaction mixture was allowed to stir for 30 minutes at this temperature. To the resulting suspension 2-(2-bromo-5-fluorophenyl)acetyl chloride (3.10 g, 12.34 mmol) was added in anhydrous 1-ethyl-3-(3-dimethylaminopropyl)carbodiimide (10 mL) and reaction was allowed to stir for 3 hours then at RT overnight. After complete consumption of starting material, reaction mixture was poured into crushed ice and extracted with dichloromethane. Organic layer was washed with brine, dried over sodium sulphate and concentrated. The residue obtained was purified by column chromatography to provide methyl 4-(4-(2-(2-bromo-5-fluorophenyl)acetyl)phenyl)butanoate (1.7 g, 4.32 mmol, 35.0% yield) as white solid.

$^1$H NMR (300 MHz, $CDCl_3$): δ 8.00 (d, J=6.2 Hz, 2H), 7.58 (dd, J=5.4 Hz, 8.7 Hz, 1H), 7.34 (d, J=8.7 Hz, 2H), 7.04 (dd, J=2.7 Hz, 8.7 Hz, 1H), 6.92 (t, J=2.7 Hz, 8.4 Hz, 1H), 4.43 (s, 2H), 3.70 (s, 3H), 2.75 (t, J=7.5 Hz, 2H), 2.37 (t, J=7.50 Hz, 2H), 2.01 (t, J=7.50, 2H); MS (m/z): 395 (M+2).

Step 5c

Synthesis of methyl 4-(4-(2-(2-bromo-5-fluorobenzyl)-1,3-dithiolan-2-yl)phenyl)butanoate To a solution of methyl 4-(4-(2-(2-bromo-5-fluorophenyl) acetyl)phenyl)butanoate (3 g, 7.63 mmol), ethane-1,2-dithiol (0.934 g, 9.92 mmol) in dichloromethane (10 mL), Boron trifluoride diethyl etherate (1.257 mL, 9.92 mmol) was added. Reaction was allowed to stir at room temperature overnight. After complete consumption of starting material, reaction mixture was concentrated and purified by column chromatography to provide methyl 4-(4-(2-(2-bromo-5-fluorobenzyl)-1,3-dithiolan-2-yl)phenyl)butanoate (3.2 g, 6.82 mmol, 89% yield) as yellow solid.

$^1$H NMR (300 MHz, $CDCl_3$): δ 7.56 (d, J=6.2 Hz, 2H), 7.48-7.43 (dd, J=5.4 Hz, 8.7 Hz, 1H), 7.13 (d, J=8.7 Hz, 2H), 6.84-6.79 (m, 2H), 3.73 (s, 2H), 3.69 (s, 3H), 3.37-3.20 (m, 4H), 2.66 (t, J=7.5 Hz, 2H), 2.34 (t, J=7.50 Hz, 2H), 2.01-1.92 (m, J=7.50, 2H); MS (m/z): 370 (M+1).

Step 5d

Synthesis of methyl 4-(4-(2-(2-bromo-5-fluorophenyl)acetyl)phenyl)butanoate

To a suspension of 1-iodopyrrolidine-2,5-dione (613 mg, 2.73 mmol) and methyl 4-(4-(2-(2-bromo-5-fluorobenzyl)-1,3-dithiolan-2-yl)phenyl)butanoate (320 mg, 0.682 mmol) in dichloromethane (10 mL) was added pyridine, hydrogen fluoride 30% solution (772 mg, 5.45 mmol) at −78° C. and reaction mixture was allowed to stir at same temperature for 4 hours. The reaction mixture was then allowed to stir overnight at RT after which reaction mass was quenched with addition of saturated sodium bicarbonate. Reaction mixture was extracted with dichloromethane, washed with brine, dried over sodium sulphate and concentrated to give crude which was purified using column chromatography to provide methyl 4-(4-(2-(2-bromo-5-fluorophenyl)acetyl)phenyl)butanoate (10 mg, 0.025 mmol, 3.73% yield) along with formation of methyl 4-(4-methoxyphenyl)-4-oxobutanoate.

$^1$H NMR (300 MHz, $CDCl_3$): δ 7.51 (dd, J=5, 4 Hz, 1H), 7.35 (d, J=8.1 Hz, 2H), 7.23 (d, J=8.1 Hz, 2H), 7.12 (dd, J=2.4 Hz, 8.7 Hz, 1H), 6.93 (t, J=2.7 Hz, 8.7 Hz, 1H), 3.69 (s, 3H), 3.61 (t, J=15.6 Hz, HF coupling, 2H), 2.72 (t, J=7.5 Hz, 2H), 2.34 (t, J=7.5 Hz, 2H), 2.02-1.92 (m, 2H); MS (m/z): 415 (M+1).

Step 5e

Synthesis of methyl 4-(4-(1,1-difluoro-2-(5-fluoro-2-(5-methylthiophen-2-yl)phenyl)ethyl)phenyl)butanoate In a mixture of methyl 4-(4-(2-(2-bromo-5-fluorophenyl)-1,1-difluoroethyl)phenyl)butanoate (30.6 mg, 0.074 mmol), 4,4,5,5-tetramethyl-2-(5-methylthiophen-2-yl)-1,3,2-dioxaborolane (33.0 mg, 0.147 mmol) and sodium bicarbonate (12.38 mg, 0.147 mmol) in dioxane:water (4:1), tetrakis(triphenylphosphine)palladium(0) (1.064 mg, 3.68 μmol) was added. Reaction mixture was heated in microwave at 111° C. for 11 minutes and was quenched with water (10 mL) and extracted with ethyl acetate (2×25 mL). Combined organic layer was dried and concentrated. Crude residue obtained was purified by column chromatography using 5% ethyl acetate in petroleum ether to provide methyl 4-(4-(1,1-difluoro-2-(5-fluoro-2-(5-methylthiophen-2-yl)phenyl)ethyl)phenyl)butanoate. (10 mg, 0.035 mmol, 31.3% yield)

$^1$H NMR (300 MHz, $CDCl_3$): δ 7.31 (d, J=5.4 Hz, 1H), 7.22-7.14 (m, 5H), 7.03 (dd, J=2.7 Hz, 8.1 Hz, 1H), 6.67 (d, J=2.4 Hz, 1H), 6.51 (d, J=2.7 Hz, 1H), 3.69 (s, 3H), 3.60 (t, J=15.6 Hz, 2H), 2.67 (t, J=7.5 Hz, 2H), 2.50 (s, 3H), 2.32 (t, J=7.5 Hz, 2H), 2.08-1.92 (m, 2H); MS (m/z): 433.1 (M+1).

Step 5f

Synthesis of 4-(4-(1,1-difluoro-2-(5-fluoro-2-(5-methylthiophen-2-yl)phenyl)ethyl)phenyl)butanoic acid To solution of methyl 4-(4-(1,1-difluoro-2-(5-fluoro-2-(5-methylthiophen-2-yl)phenyl)ethyl)phenyl)butanoate (20 mg, 0.046 mmol) in THF:methanol (4:1) was added lithium hydroxide hydrate (185 μL, 0.277 mmol) at RT. Reaction mixture was allowed to stir at RT for 4 hours. After complete consumption of starting material, solvent was evaporated under reduced pressure and was washed with 5% ethyl acetate in petroleum ether. Reaction mixture was then quenched with addition of saturated ammonium chloride and extracted with ethyl acetate. Organic layer was dried over sodium sulphate and concentrated to provide 4-(4-(1,1-difluoro-2-(5-fluoro-2-(5-methylthiophen-2-yl)phenyl)ethyl)phenyl)butanoic acid (13 mg, 0.031 mmol, 67.2% yield).

$^1$H NMR (300 MHz, $CDCl_3$): δ 7.31 (d, J=5.4 Hz, 1H), 7.22-7.14 (m, 5H), 7.03 (dd, J=2.7 Hz, 8.1 Hz, 1H), 6.67 (d, J=2.4 Hz, 1H), 6.51 (d, J=2.7 Hz, 1H), 3.55 (t, J=15.6 Hz, 2H), 2.73 (t, J=7.5 Hz, 2H), 2.50 (s, 3H), 2.32 (t, J=7.5 Hz, 2H), 2.08-1.92 (m, 2H); MS (m/z): 419.1 (M+1).

Example 6

4-(4-(1,1-Difluoro-2-(5-fluoro-2-(5-(1-methylcyclopropyl)thiophen-2-yl)phenyl)ethyl)phenyl)butanoic acid (Compound 6)

Step 6a

Synthesis of methyl 4-(4-(1,1-difluoro-2-(5-fluoro-2-(5-(1-methylcyclopropyl)thiophen-2-yl)phenyl)ethyl)phenyl)butanoate A solution of methyl 4-(4-(2-(2-bromo-5-fluorophenyl)-1,1-difluoroethyl)phenyl)butanoate (70 mg, 0.169 mmol), 4,4,5,5-tetramethyl-2-(5-(1-methylcyclopropyl)thiophen-2-yl)-1,3,2-dioxaborolane (111 mg, 0.421 mmol), sodium bicarbonate (28.3 mg, 0.337 mmol) in dioxane and water (4:1, 4 mL) was degassed under argon. To the resulting mixture tetrakis(triphenylphosphine)palladium(0) (2.435 mg, 8.43 μmol) was added and reaction mixture was heated in microwave at 111° C. for 10 min. Reaction mixture was concentrated under reduced pressure and the crude product was purified by column chromatography to provide methyl 4-(4-(1,1-difluoro-2-(5-fluoro-2-(5-(1-methylcyclopropyl)thiophen-2-yl)phenyl)ethyl)phenyl)butanoate (35 mg, 0.074 mmol, 43.9% yield).

$^1$H NMR (300 MHz, $CDCl_3$): δ 7.30-7.25 (m, 1H) 7.21-7.14 (m, 5H), 7.01 (t, J=2 Hz, 8 Hz, 1H), 6.65 (d, J=2.2 Hz, 1H), 6.48 (d, J=2.2 Hz, 1H), 3.69 (s, 3H), 3.54 (t, J=12.2 Hz, 2H), 2.68 (t, J=6 Hz, 2H), 2.32 (d, J=2.2 Hz, 2H), 2.02-1.94 (m, 2H), 1.60 (3H), 0.95-0.94 (m, 2H), 0.88-0.87 (m, 2H); MS (m/z): 473.

Step 6b

Synthesis of 4-(4-(1,1-difluoro-2-(5-fluoro-2-(5-(1-methylcyclopropyl)thiophen-2-yl)phenyl)ethyl)phenyl)butanoic acid To a solution of methyl 4-(4-(1,1-difluoro-2-(5-fluoro-2-(5-(1-methylcyclopropyl)thiophen-2-yl)phenyl)ethyl)phenyl)butanoate (20 mg, 0.042 mmol) in THF (4 mL) and methanol (1 mL), aqueous lithium hydroxide (6.08 mg, 0.254 mmol) was added and allowed to stir at RT for 6 hours. Reaction mixture was concentrated, quenched with dilute ammonium chloride and extracted with ethyl acetate. Organic layer was dried over sodium sulfate and concentrated. The residue obtained was diluted with ethyl acetate (1 mL) followed by precipitation with n-hexane. The precipitate was dried under vacuum to obtain desired 4-(4-(1,1- difluoro-2-(5-fluoro-2-(5-(1-methylcyclopropyl)thiophen-2-yl)phenyl)ethyl)phenyl)butanoic acid (12 mg, 0.026 mmol, 61.8% yield).

$^{1}$H NMR (300 MHz, $CDCl_3$): δ 7.30-7.14 (m, 6H), 7.20 (t, J=8 Hz, 2.5 Hz, 1H), 6.66 (d, J=2.2 Hz, 1H), 6.48 (d, J=2.2 Hz, 1H), 3.49 (t, J=13 Hz, 2H), 2.70 (t, J=6.2 Hz, 2H), 2.35 (t, J=6.5 Hz, 2H), 2.02-1.94 (m, J=6.4 Hz, 2H), 1.27 (s, 3H), 0.95-0.94 (m, 2H), 0.8-0.87 (m, 2H); MS (m/z): 459 (M+1).

Example 7

4-(4-(1,1-Difluoro-2-(4-fluoro-4'-methyl-[1,1'-biphenyl]-2-yl)ethyl)phenyl)butanoic acid (Compound 7)

Step 7a

Synthesis of methyl 4-(4-(1,1-difluoro-2-(4-fluoro-4'-methyl-[1,1'-biphenyl]-2-yl)ethyl)phenyl)butanoate To a degassed solution of methyl 4-(4-(2-(2-bromo-5-fluorophenyl)-1,1-difluoroethyl)phenyl)butanoate (80 mg, 0.193 mmol), 4,4,5,5-tetramethyl-2-(p-tolyl)-1,3,2-dioxaborolane (84 mg, 0.385 mmol), sodium bicarbonate (32.4 mg, 0.385 mmol) in dioxane:water (4 mL:1 mL), tetrakis (triphenylphosphine)palladium(0) (5.57 mg, 0.019 mmol) was added and the reaction mass was heated in microwave at 111° C. for 10 minutes. Reaction mixture was then concentrated and purified by column chromatography to obtain methyl 4-(4-(1,1-difluoro-2-(4-fluoro-4'-methyl-[1,1'-biphenyl]-2-yl)ethyl)phenyl)butanoate. (65 mg, 0.152 mmol, 79% yield)

$^{1}$H NMR (300 MHz, $CDCl_3$): δ 7.20-7.00 (m, 8H), 6.87-6.84 (m, 3H), 3.69 (s, 3H), 3.45 (t, J=15.9 Hz, 2H), 2.69 (t, J=7.5 Hz, 2H), 2.40 (s, 3H), 2.37 (t, J=7.5 Hz, 2H), 1.99-1.94 (m, 2H); MS (m/z): 449 (M+Na).

Step 7b

Synthesis of 4-(4-(1,1-difluoro-2-(4-fluoro-4'-methyl-[1,1'-biphenyl]-2-yl)ethyl)phenyl)butanoic acid To a solution of methyl 4-(4-(1,1-difluoro-2-(4-fluoro-4'-methyl-[1,1'-biphenyl]-2-yl)ethyl)phenyl)butanoate (58 mg, 0.136 mmol) in 4 mL of THF:Methanol (4:1) was added lithium hydroxide monohydrate (453 μL, 0.680 mmol) and the reaction mixture was allowed to stir at RT overnight. After complete consumption of starting material, solvent was removed under reduced pressure. The reaction mixture was neutralized with saturated ammonium chloride and extracted with ethyl acetate, dried over sodium sulphate to obtain 4-(4-(1,1-difluoro-2-(4-fluoro-4'-methyl-[1,1'-biphenyl]-2-yl)ethyl)phenyl)butanoic acid (56 mg, 0.136 mmol) $^{1}$H NMR (300 MHz, DMSO-$d_6$): δ 7.16-7.13 (m, 7H), 7.08 (d, J=8.1 Hz, 2H), 6.94 (d, J=7.8 Hz, 2H), 3.60 (t, J=14.4 Hz, 2H), 2.62 (t, J=7.2 Hz, 2H), 2.34 (s, 3H), 2.23 (t, J=7.2 Hz, 2H), 1.81-1.76 (m, 2H); MS (m/z): 413 (M+1).

Example 8

4-(4-(2-(2-(5-Cyclopropylthiophen-2-yl)-5-fluorophenyl)-1,1-difluoroethyl)phenyl)butanoic acid (Compound 8)

Step 8a

Synthesis of methyl 4-(4-(2-(2-(5-cyclopropylthiophen-2-yl)-5-fluorophenyl)-1,1-difluoroethyl)phenyl)butanoate To a degassed solution of methyl 4-(4-(2-(2-bromo-5-fluorophenyl)-1,1-difluoroethyl)phenyl)butanoate (80 mg, 0.193 mmol), 2-(5-cyclopropylthiophen-2-yl)-4,4,5,5-tetramethyl-1,3,2-dioxaborolane (96 mg, 0.385 mmol), sodium bicarbonate (32.4 mg, 0.385 mmol) in dioxane (4 mL):water (1 mL), tetrakis(triphenylphosphine)palladium (0) (5.57 mg, 0.019 mmol) was added and the reaction mixture was heated in microwave at 111° C. for 10 minutes. Reaction mixture was concentrated and purified by column chromatography to provide methyl 4-(4-(2-(2-(5-cyclopropylthiophen-2-yl)-5-fluorophenyl)-1,1-difluoroethyl)phenyl)butanoate (72 mg, 0.157 mmol, 82% yield).

$^{1}$H NMR (300 MHz, DMSO-$d_6$): δ 7.32-7.30 (m, 1H), 7.22-7.15 (m, 6H), 6.76 (d, J=3 Hz, 1H), 6.67 (d, J=3.3 Hz, 1H), 3.70 (t, J=13.5 Hz, 2H), 3.58 (s, 3H), 2.64 (t, J=7.5 Hz, 2H), 2.33 (t, J=7.5 Hz, 2H), 2.11-2.10 (m, 1H), 1.85-1.80 (m, 2H), 1.02-0.99 (m, 2H), 0.68-0.66 (m, 2H); MS (m/z): 481 (M+Na).

Step 8b

Synthesis of 4-(4-(2-(2-(5-cyclopropylthiophen-2-yl)-5-fluorophenyl)-1,1-difluoroethyl)phenyl)butanoic acid To a solution of methyl 4-(4-(2-(2-(5-cyclopropylthiophen-2-yl)-5-fluorophenyl)-1,1-difluoroethyl)phenyl)butanoate (62 mg, 0.135 mmol) in 4 mL of THF:methanol (4:1) was added lithium hydroxide monohydrate (451 μL, 0.676 mmol) and the reaction mixture was allowed to stir at RT overnight. After complete consumption of starting material, solvent was removed under reduced pressure. The reaction mixture was neutralized with saturated ammonium chloride and extracted with ethyl acetate, dried over sodium sulphate to obtain 4-(4-(2-(2-(5-cyclopropylthiophen-2-yl)-5-fluorophenyl)-1,1-difluoroethyl)phenyl)butanoic acid (60 mg, 0.135 mmol).

$^{1}$H NMR (300 MHz, DMSO-$d_6$): δ 12.12 (s, 1H), 7.32-7.15 (m, 7H), 6.75-6.66 (m, 2H), 3.70 (t, J=16.8 Hz, 2H), 2.61 (t, J=7.5 Hz, 2H), 2.24-2.11 (m, 3H), 1.82-1.77 (m, 2H), 1.01-0.98 (m, 2H), 0.68-0.66 (m, 2H); MS (m/z): 443 (M+1).

Example 9

4-(4-(2-(2-(2,3-Dihydrobenzofuran-5-yl)-5-fluorophenyl)-1,1-difluoroethyl)phenyl)butanoic acid (Compound 9)

Step 9a

Synthesis of methyl 4-(4-(2-(2-(2,3-dihydrobenzofuran-5-yl)-5-fluorophenyl)-1,1-difluoroethyl)phenyl)butanoate To a degassed solution of methyl 4-(4-(2-(2-bromo-5-fluorophenyl)-1,1-difluoroethyl)phenyl)butanoate (80 mg, 0.193 mmol), (2,3-dihydrobenzofuran-5-yl)boronic acid (63.2 mg, 0.385 mmol), sodium bicarbonate (32.4 mg, 0.385 mmol) in dioxane (4 mL):water (1 mL), tetrakis(triphenylphosphine)palladium(0) (5.57 mg, 0.019 mmol) was added and the reaction mixture was heated in microwave at 111° C. for 10 minutes. Reaction mixture was concentrated and purified by column chromatography to provide methyl 4-(4-(2-(2-(2,3-dihydrobenzofuran-5-yl)-5-fluorophenyl)-1,1-difluoroethyl)phenyl)butanoate (58 mg, 0.128 mmol, 66.2% yield).

$^1$H NMR (300 MHz, $CDCl_3$): δ 7.42-6.96 (m, 7H), 6.74-6.65 (m, 3H), 4.65 (t, J=8.7 Hz, 2H), 3.68 (s, 3H), 3.44 (t, J=15.9 Hz, 2H), 3.23 (t, J=8.7 Hz, 2H), 2.69 (t, J=7.5 Hz, 2H), 2.37 9 (t, J=7.5 Hz, 2H), 2.01-1.91 (m, 2H); MS (m/z): 477 (M+Na).

Step 9b

Synthesis of 4-(4-(2-(2-(2,3-dihydrobenzofuran-5-yl)-5-fluorophenyl)-1,1-difluoroethyl)phenyl)butanoic acid To a solution of methyl 4-(4-(2-(2-(2,3-dihydrobenzofuran-5-yl)-5-fluorophenyl)-1,1-difluoroethyl)phenyl)butanoate (58 mg, 0.128 mmol) in 4 mL of THF:Methanol (4:1) was added lithium hydroxide monohydrate (26.8 mg, 0.638 mmol) and the reaction mixture was allowed to stir at RT overnight. After complete consumption of starting material, solvent was removed under reduced pressure. The reaction mixture was neutralized with saturated ammonium chloride and extracted with ethyl acetate, dried over sodium sulphate to provide 4-(4-(2-(2-(2,3-dihydrobenzofuran-5-yl)-5-fluorophenyl)-1,1-difluoroethyl)phenyl)butanoic acid (43 mg, 0.098 mmol, 76% yield).

$^1$H NMR (300 MHz, DMSO-$d_6$): δ 12.10 (s, 1H), 7.21-7.13 (m, 5H), 7.07-7.04 (m, 2H), 6.72 (s, 3H), 4.58 (t, J=8.7 Hz, 2H), 3.54 (t, J=16.5 Hz, 2H), 3.19 (t, J=8.7 Hz, 2H), 2.63 (t, J=7.5 Hz, 2H), 2.23 (t, J=7.5 Hz, 2H), 1.81-1.76 (m, 2H); MS (m/z): 439 (M−1).

Example 10

4-(4-(2-(4'-Cyclopropyl-4-fluoro-[1,1'-biphenyl]-2-yl)-1,1-difluoroethyl)phenyl)butanoic acid (Compound 10)

Step 10a

Synthesis of methyl 4-(4-(2-(4'-cyclopropyl-4-fluoro-[1,1'-biphenyl]-2-yl)-1,1-difluoroethyl)phenyl)butanoate To a degassed solution of methyl 4-(4-(2-(2-bromo-5-fluorophenyl)-1,1-difluoroethyl)phenyl)butanoate (80 mg, 0.193 mmol), sodium bicarbonate (32.4 mg, 0.385 mmol), (4-cyclopropylphenyl)boronic acid (62.4 mg, 0.385 mmol) in dioxane (4 mL) and water (1 mL), tetrakis(triphenylphosphine)palladium(0) (5.57 mg, 0.019 mmol) was added and the reaction mass was heated in microwave at 111° C. for 10 minutes. Reaction mixture was concentrated and purified by column chromatography to provide methyl 4-(4-(2-(4'-cyclopropyl-4-fluoro-[1,1'-biphenyl]-2-yl)-1,1-difluoroethyl)phenyl)butanoate (73 mg, 0.161 mmol, 84% yield).

$^1$H NMR (300 MHz, $CDCl_3$): δ 7.19-6.96 (m, 9H), 6.86 (d, J=8.1 Hz, 2H), 3.69 (s, 3H), 3.45 (t, J=15.9 Hz, 2H), 2.69 (t, J=7.2 Hz, 2H), 2.37 (t, J=7.2 Hz, 2H), 2.01-1.89 (m, 3H), 1.06-0.99 (m, 2H), 0.77-0.72 (m, 2H); MS (m/z): 475 (M+Na).

Step 10b

Synthesis of 4-(4-(2-(4'-cyclopropyl-4-fluoro-[1,1'-biphenyl]-2-yl)-1,1-difluoroethyl)phenyl)butanoic acid To a solution of methyl 4-(4-(2-(4'-cyclopropyl-4-fluoro-[1,1'-biphenyl]-2-yl)-1,1-difluoroethyl)phenyl)butanoate (70 mg, 0.155 mmol) in 4 mL of THF:Methanol (4:1) was added lithium hydroxide monohydrate (32.5 mg, 0.773 mmol) and the reaction mixture was allowed to stir at RT overnight. After complete consumption of starting material, solvent was removed under reduced pressure. The reaction mixture was neutralized with saturated ammonium chloride and extracted with ethyl acetate, dried over sodium sulphate to provide 4-(4-(2-(4'-cyclopropyl-4-fluoro-[1,1'-biphenyl]-2-yl)-1,1-difluoroethyl)phenyl)butanoic acid (46 mg, 0.105 mmol, 67.8% yield).

$^1$H NMR (300 MHz, DMSO-$d_6$): δ 12.18 (s, 1H), 7.19-7.05 (m, 9H), 6.92 (d, J=7.4 Hz, 2H), 3.55 (t, J=16.5 Hz, 2H), 2.62 (t, J=7.2 Hz, 2H), 2.23 (t, J=7.2 Hz, 2H), 1.94-1.76 (m, 3H), 0.98-0.96 (m, 2H), 0.71-0.69 (m, 2H); MS (m/z): 437 (M+1).

Example 11

4-(4-((2-(5-(1-Cyanocyclopropyl)thiophen-2-yl)-5-fluorophenyl)ethynyl)phenyl)butanoic acid (Compound 11)

Step 11a

Synthesis of 1-(5-(4-fluoro-2-formylphenyl)thiophen-2-yl)cyclopropanecarbonitrile To a degassed solution of 5-fluoro-2-(4,4,5,5-tetramethyl-1,3,2-dioxaborolan-2-yl)benzaldehyde (411 mg, 1.644 mmol), 1-(5-bromothiophen-2-yl)cyclopropanecarbonitrile (250 mg, 1.096 mmol) and sodium bicarbonate (184 mg, 2.192 mmol) in dioxane (4 mL):water (1 mL), tetrakis (triphenylphosphine)palladium(0) (31.7 mg, 0.110 mmol) was added and reaction mass was heated in microwave at 111° C. for 10 minutes. The reaction mixture was then concentrated and purified by column chromatography to provide 1-(5-(4-fluoro-2-formylphenyl)thiophen-2-yl)cyclopropanecarbonitrile (297 mg, 1.095 mmol).

$^1$H NMR (300 MHz, DMSO-$d_6$): δ 10.13 (s, 1H), 7.72-7.71 (m, 1H), 7.69-7.68 (m, 2H), 6.52-6.51 (m, 2H), 1.85 (s, 2H), 1.53 (s, 2H); MS (m/z): 272 (M+1).

Step 11b

Synthesis of 1-(5-(2-ethynyl-4-fluorophenyl)thiophen-2-yl)cyclopropanecarbonitrile To a solution of 1-(5-(4-fluoro-2-formylphenyl)thiophen-2-yl)cyclopropanecarbonitrile (0.050 g, 0.184 mmol) in dry methanol (5 ml) was added potassium carbonate (0.051 g, 0.369 mmol) and dimethyl (1-diazo-2-oxopropyl)phosphonate (0.531 mL, 0.221 mmol) at RT under argon, and the mixture was stirred at RT for 1 hour. The reaction was quenched with brine (15 mL), and the mixture extracted with ethyl acetate (2×25 mL). The combined organic layer was washed with brine (30 mL), dried over sodium sulfate. Solvent was removed under reduced pressure to give crude which was purified by column chromatography to give 1-(5-(2-ethynyl-4-fluorophenyl)thiophen-2-yl)cyclopropanecarbonitrile (0.035 g, 0.131 mmol, 71.0% yield) as liquid.

$^1$H NMR (300 MHz, $CDCl_3$): δ 7.46-7.41 (m, 1H), 7.45-7.41 (m, 1H), 7.37-7.35 (m, 1H), 7.32-7.31 (m, 1H), 7.13-7.04 (m, 1H), 3.32 (s, 1H), 1.80-1.78 (m, 2H), 1.51-1.48 (m, 2H); MS (m/z): 268 (M+1).

Step 11c

Synthesis of methyl 4-(4-((2-(5-(1-cyanocyclopropyl)thiophen-2-yl)-5-fluorophenyl)ethynyl)phenyl) butanoate To a solution of methyl 4-(4-iodophenyl)butanoate (150 mg, 0.493 mmol), 1-(5-(2-ethynyl-4-fluorophenyl)thiophen-2-yl)cyclopropanecarbonitrile (158 mg, 0.592 mmol) in DMF, triethylamine (0.207 ml, 1.480 mmol) was added and the reaction mixture was degassed with argon and bis(triphenylphosphine)palladium(II) dichloride (34.6 mg, 0.049 mmol) added followed by addition of copper(I) iodide (9.39 mg, 0.049 mmol). Reaction was stirred at 85° C. for 4 hours. After completion of reaction, reaction mass was concentrated to give crude, which was purified column chromatography to provide methyl4-(4-((2-(5-(1-cyanocyclopropyl)thiophen-2-yl)-5-fluorophenyl)ethynyl)phenyl) butanoate (185 mg, 0.417 mmol, 85% yield).

$^1$H NMR (300 MHz, $CDCl_3$): δ 7.51-7.48 (m, 1H), 7.45-7.42 (m, 2H), 7.38 (dd, J=3.6, 8.4 Hz, 1H), 7.22 (d, J=7.8 Hz, 2H), 7.08-7.05 (m, 3H), 3.69 (s, 3H), 2.72 (t, J=7.2 Hz, 2H), 2.38 (t, J=7.5 Hz, 2H), 2.03-1.96 (m, 2H), 1.83-1.79 (m, 2H), 1.53-1.48 (m, 2H); MS (m/z): 444 (M+1).

Step 11d

Synthesis of 4-(4-((2-(5-(1-cyanocyclopropyl)thiophen-2-yl)-5-fluorophenyl)ethynyl)-phenyl) butanoic acid To a solution of methyl 4-(4-((2-(5-(1-cyanocyclopropyl) thiophen-2-yl)-5-fluorophenyl)ethynyl)phenyl)butanoate (30 mg, 0.068 mmol) in 4 mL of THF:methanol (4:1), $LiOH.H_2O$ (225 μL, 0.338 mmol) was added and the reaction mixture was allowed to stir at RT overnight. After complete consumption of starting material, solvent was removed under reduced pressure. The reaction mixture was neutralized with saturated ammonium chloride, extracted with ethyl acetate and dried over sodium sulphate to get 4-(4-((2-(5-(1-cyanocyclopropyl)thiophen-2-yl)-5-fluorophenyl)ethynyl)phenyl)butanoic acid (25 mg, 0.058 mmol, 86% yield).

$^1$H NMR (300 MHz, DMSO-$d_6$): δ 7.73-7.70 (m, 1H), 7.51-7.49 (m, 4H), 7.34-7.27 (m, 3H), 7.15 (d, J=3.6 Hz, 1H), 2.63 (t, J=7.2 Hz, 2H), 2.24 (t, J=7.5 Hz, 2H), 1.86-1.80 (m, 2H), 1.83-1.79 (m, 2H), 1.53-1.48 (m, 2H); MS (m/z): 430.1 (M+1).

Compounds 12 to 22 were prepared analogous to Compounds 1 to 11 and are provided in Table 1

TABLE 1

| | |
|---|---|
| Compound 12 | 4-(4-(5-fluoro-2-(4,5,6,7-tetrahydrobenzo[d]thiazol-2-yl)phenethyl)phenyl)butanoic acid 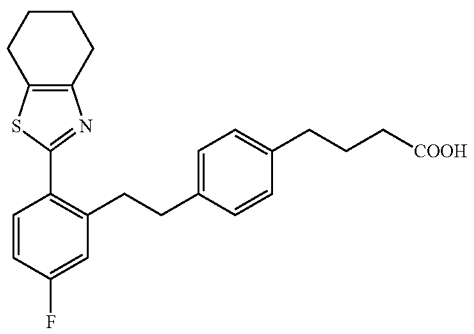 |
| Compound 13 | 4-(4-(2-(5-cyclopropylthiophen-2-yl)-5-fluorophenethyl)phenyl)butanoic acid 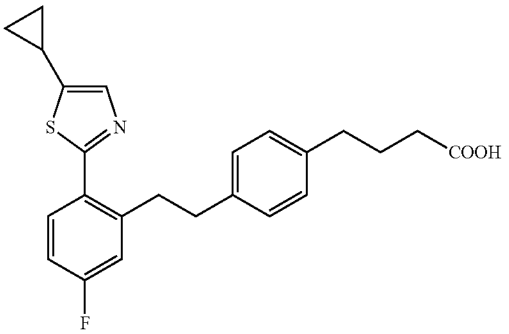 |
| Compound 14 | 4-(4-(5-fluoro-2-(5-(1-methylcyclopropyl)thiophen-2-yl)styryl)phenyl)butanoic acid 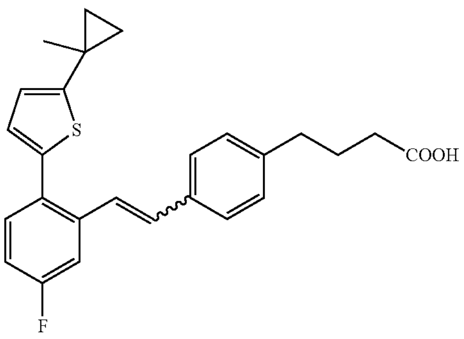 |

TABLE 1-continued

Compound 15 4-(4-(2-(5-(1-cyanocyclopropyl)thiophen-2-yl)-5-fluorostyryl)phenyl)butanoic acid

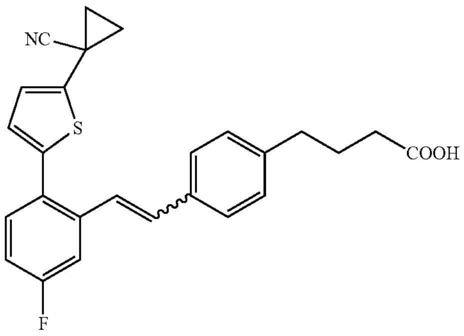

Compound 16 4-(4-(5-fluoro-2-(4,5,6,7-tetrahydrobenzo[b]thiophen-2-yl)styryl)phenyl)butanoic acid

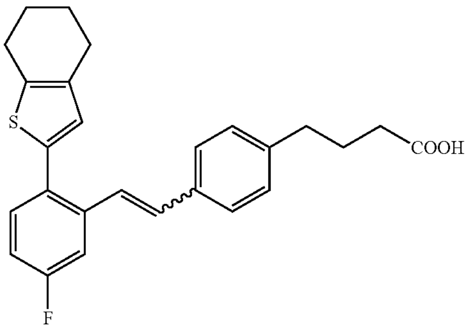

Compound 17 4-(4-(5-fluoro-2-(4,5,6,7-tetrahydrobenzo[d]thiazol-2-yl)styryl)phenyl)butanoic acid

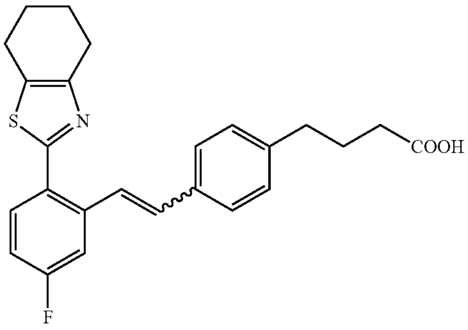

Compound 18 4-(4-((2-(5-cyclopropylthiophen-2-yl)-5-fluorophenyl)ethynyl)phenyl)butanoic acid

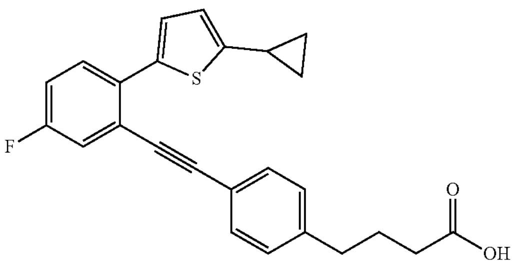

TABLE 1-continued

Compound 19 4-(4-((5-fluoro-2-(4,5,6,7-tetrahydrobenzo[d]thiazol-2-yl)phenyl)ethynyl)phenyl)butanoic acid

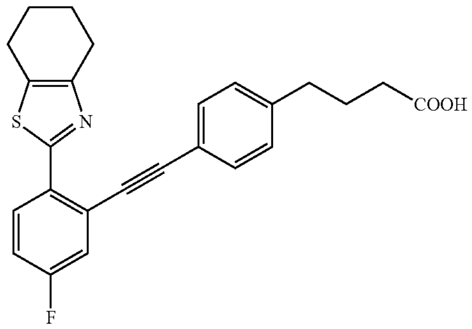

Compound 20 4-(4-(1,1-difluoro-2-(5-fluoro-2-(6-methoxypyridin-3-yl)phenyl)ethyl)phenyl)butanoic acid

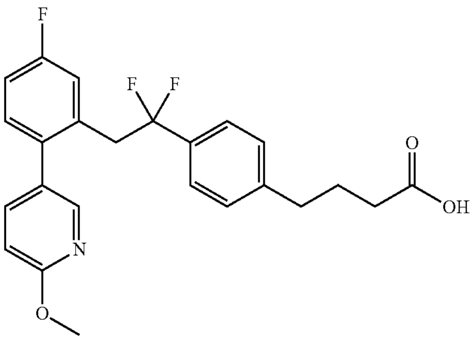

Compound 21 4-(4-(1,1-difluoro-2-(5-fluoro-2-(5,6,7,8-tetrahydronaphthalen-2-yl)phenyl)ethyl)phenyl)butanoic acid

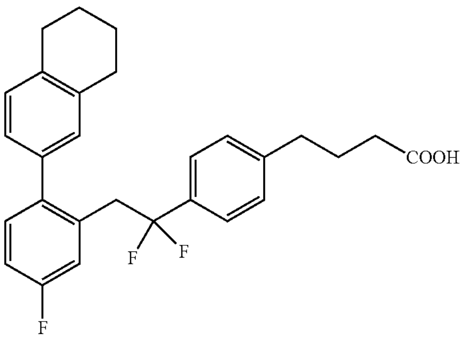

TABLE 1-continued

Compound 22 — 4-(4-(2-(2-(bicyclo[4.2.0]octa-1(6),2,4-trien-3-yl)-5-fluorophenyl)-1,1-difluoroethyl)phenyl)butanoic acid

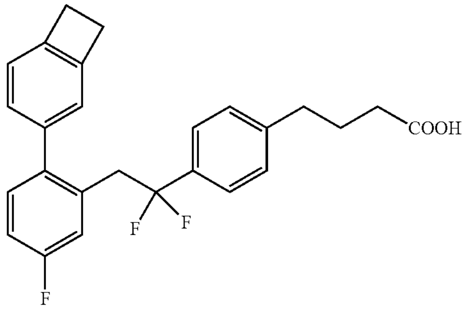

Biological Assays

Representative compounds of Formula (I) of the present invention (referred to as test compounds) were tested for their activity using the assays and the methods described below.

Beta (β) arrestin 2 Interaction Assay (BRET assay) was performed using CHO-$K_1$ cells stably expressing the GPR120L (Long Isoform) receptor using β-galactosidase (Beta gal) enzyme fragment complementation assay. The measurement of GPR120 activation upon agonist activation was directly provided by β-arrestin recruitment. One day before the β-arrestin 2 assay, CHO-K1 cells were seeded and incubated overnight at 37° C. in a 5% $CO_2$ humidified atmosphere. Cells were treated with the test compounds in various concentrations ranging from 30 μM to 1 nM and incubated for 2 hours for GPCR (GPR120) activation. Extent of Arrestin recruitment was measured by adding detection reagents for Beta gal complementation assay, and was further incubated for 1 hour. The chemiluminescent signal was detected on Polar Star (BMG Labtech). The dose-response curve was analyzed using Sigma Plot/Graph Pad. The $EC_{50}$ (concentration of the test compounds where 50% of compounds' maximal activity is observed) values were calculated from the dose-response curve. Similar procedure was followed for HEK 293 cells and results obtained are tabulated in Table 2.

TABLE 2

$EC_{50}$ values of compounds of Examples

| Compound No. | $EC_{50}$ (nM) |
|---|---|
| Compound 3 | + |
| Compound 5 | +++ |
| Compound 6 | ++ |
| Compound 11 | ++ |
| Compound 12 | +++ |
| Compound 13 | ++ |
| Compound 14 | +++ |
| Compound 18 | +++ |
| Compound 20 | +++ |

The $EC_{50}$ (nM) values of the compounds are presented in Table 1 wherein:
+++ corresponds to $EC_{50}$ ranging from 50 nM to 500 nM;
++ corresponds to $EC_{50}$ ranging from 500 nM to 5000 nM;
+ corresponds to $EC_{50}$ ranging from 5000 nM to 10000 nM;
Conclusion: The $EC_{50}$ values determined for the compounds of the present invention is indicative of GPR120 agonist activity of the compounds of the present invention.

We claim:

1. A compound of formula (I);

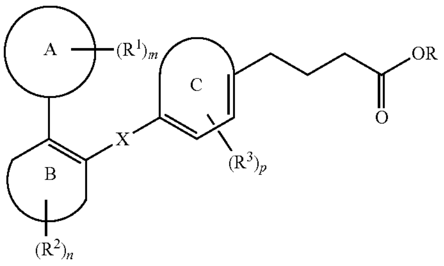

(I)

wherein,

Ring A is selected from the group consisting of a 3- to 10-membered cycloalkyl, a 5- to 12-membered heterocycloalkyl, $(C_6-C_{10})$aryl, and a 5- to 12-membered heteroaryl, wherein the heterocycloalkyl and the heteroaryl contain 1, 2, 3 or 4 heteroatoms independently selected from the group consisting of N, O and S;

Ring B and Ring C are independently selected from a $(C_6-C_{10})$aryl or a 5- to 12-membered heteroaryl containing 1, 2 or 3 heteroatoms independently selected from the group consisting of N, O and S;

X is selected from

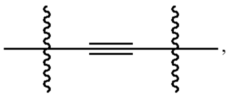

,

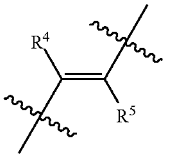

and

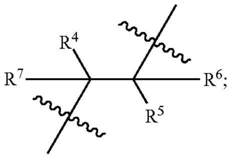

;

wherein  represents a point of attachment;

R is hydrogen or a $(C_1-C_6)$alkyl;

$R^1$, $R^2$, and $R^3$ at each occurrence are independently selected from the group consisting of hydrogen, a halogen, a $(C_1-C_6)$alkyl, a halo$(C_1-C_6)$alkyl, a 3- to 10-membered cycloalkyl and 5- to 12-membered heterocycloalkyl; or two $R^1$ are combined together with Ring A to form a 3- to 6-membered cycloalkyl or a 5- to 12-membered heterocycloalkyl;

$R^4$ and $R^7$ are independently selected from hydrogen or a $(C_1-C_6)$alkyl;

$R^5$ and $R^6$ are independently selected from the group consisting of hydrogen, a halogen and a $(C_1-C_6)$alkyl; and m, n and p are each integer independently selected from 1, 2 and 3;

wherein, the $(C_1-C_6)$alkyl is unsubstituted or substituted with one or more groups independently selected from the group consisting of halogen, hydroxy, cyano, nitro, $(C_1-C_6)$ alkyl, halo$(C_1-C_6)$alkyl, —O$(C_1-C_6)$alkyl, $(C_3-C_8)$cycloalkyl, $(C_6-C_{10})$aryl, heterocycloalkyl, and heteroaryl;

the cycloalkyl is a 3- to 10-membered ring, which is unsubstituted or substituted with one or more groups independently selected from the group consisting of ($C_1$-$C_6$)alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino, and cyano;

the heteroaryl is a 5- to 12-membered ring, which is unsubstituted or substituted with one or more groups independently selected from the group consisting of ($C_1$-$C_6$)alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino, and cyano;

the heterocycloalkyl is a 5- to 12-membered ring, which is unsubstituted or substituted with one or more groups independently selected from the group consisting of ($C_1$-$C_6$)alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino, and cyano;

the halogen is selected from chlorine, bromine, iodine, and fluorine; or a stereoisomer, a tautomer, or a pharmaceutically acceptable salt thereof.

2. The compound of Formula (I) according to claim 1, wherein Ring A is unsubstituted or substituted 3- to 10-membered cycloalkyl or unsubstituted or substituted 5- to 12-membered heterocycloalkyl containing 1, 2, 3 or 4 heteroatoms independently selected from the group consisting of N, O and S, or unsubstituted or substituted ($C_6$-$C_{10}$) aryl, or 5- to 12-membered heteroaryl containing 1, 2, 3 or 4 heteroatoms independently selected from the group consisting of N, O and S, an or unsaturated or partially unsaturated ($C_6$-$C_{10}$)aryl or unsaturated or partially unsaturated 5- to 12-membered heteroaryl.

3. The compound of Formula (I) according to claim 1, wherein Ring A is selected from

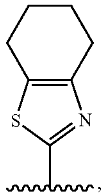,
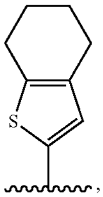,
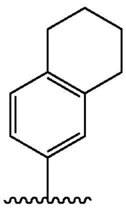
or
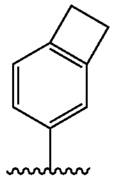

wherein represents a point of attachment to Ring B.

4. The compound of Formula (I) according to claim 1, wherein Ring B is selected from the group consisting of an unsubstituted or substituted ($C_6$-$C_{10}$)aryl and a 5- to 12-membered heteroaryl containing 1, 2 or 3 heteroatoms independently selected from the group consisting of N, O and S.

5. The compound of Formula (I) according to claim 4, wherein Ring B is an unsubstituted or substituted phenyl.

6. The compound of Formula (I) according to claim 4, wherein Ring B is an unsubstituted or substituted phenyl and $R^2$ is located at a para position to Ring A and n is 1.

7. The compound of Formula (I) according to claim 4, wherein Ring B is phenyl and $R^2$ is a halogen located at a para position to Ring A and n is 1.

8. The compound of Formula (I) according to claim 1, wherein Ring C is selected from the group consisting of an unsubstituted or substituted ($C_6$-$C_{10}$)aryl and a 5- to 12-membered heteroaryl containing 1, 2 or 3 heteroatoms independently selected from the group consisting of N, O and S.

9. The compound of Formula (I) according to claim 8, wherein Ring C is selected from the group consisting of an unsubstituted or substituted phenyl, and an unsubstituted or substituted 5- to 6-membered heteroaryl.

10. The compound of Formula (I) according to claim 1, wherein two $R^1$ are combined together with Ring A to form a 3- to 6-membered cycloalkyl or a 5- to 12-membered heterocycloalkyl.

11. The compound of Formula (I) according to claim 1, wherein Ring B is an unsubstituted or substituted phenyl; Ring C is selected from the group consisting of an unsubstituted or substituted phenyl, and an unsubstituted or substituted 5- to 6-membered heteroaryl; $R^2$ is located at a para position to Ring A; $R^3$ is hydrogen; and m & n are 1.

12. The compound of Formula (I) according to claim 1, wherein Ring B is an unsubstituted or substituted phenyl; Ring C is an unsubstituted or substituted phenyl, $R^2$ is a halogen located at a para position to Ring A; $R^3$ is hydrogen; and m & n are 1.

13. The compound of Formula (I) according to claim 1, wherein Ring B is an unsubstituted or substituted phenyl; Ring C is an unsubstituted or substituted 5- to 6-membered heteroaryl; $R^2$ is located at a para position to Ring A; $R^3$ is hydrogen; and m & n are 1.

14. The compound of Formula (I) according to claim 1, wherein Ring B is an unsubstituted or substituted ($C_6$-$C_{10}$) aryl or an 5- to 12-membered heteroaryl; Ring C is an unsubstituted or substituted ($C_6$-$C_{10}$)aryl or a 5- to 12-membered heteroaryl; and Ring A is a saturated or partially unsaturated 5- to 12-membered bicyclic heteroaryl or a 5- to 12-membered bicyclic heterocycloalkyl.

15. The compound of Formula (I) according to claim 1, wherein Ring B is an unsubstituted or substituted ($C_6$-$C_{10}$) aryl or a 5- to 12-membered heteroaryl; Ring C is an unsubstituted or substituted ($C_6$-$C_{10}$)aryl or a 5- to 12-membered heteroaryl; Ring A is a 5- to 6-membered monocyclic heteroaryl; and $R^1$ is a 3- to 10-membered cycloalkyl.

16. A compound of Formula IA;

Formula IA (IA)

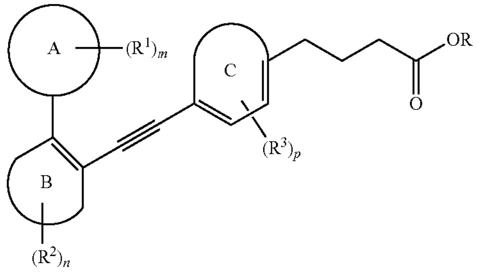

wherein,

Ring A is selected from the group consisting of a 3- to 10-membered cycloalkyl, a 5- to 12-membered heterocycloalkyl, a ($C_6$-$C_{10}$)aryl, and a 5- to 12-membered heteroaryl, wherein the heterocycloalkyl and the heteroaryl contain 1, 2, 3 or 4 heteroatoms independently selected from the group consisting of N, O and S;

Ring B and Ring C are independently selected from a $(C_6-C_{10})$aryl and a 5- to 12-membered heteroaryl containing 1, 2 or 3 heteroatoms independently selected from the group consisting of N, O and S;

R is hydrogen or a $(C_1-C_6)$alkyl;

$R^1$, $R^2$, and $R^3$ at each occurrence are independently selected from the group consisting of hydrogen, a halogen, a $(C_1-C_6)$alkyl, a halo$(C_1-C_6)$alkyl, a 3- to 10-membered cycloalkyl, and a 5- to 12-membered heterocycloalkyl; and m, n and p are each an integer independently selected from 1, 2 and 3;

wherein, the $(C_1-C_6)$alkyl is unsubstituted or substituted with one or more groups independently selected from the group consisting of halogen, hydroxy, cyano, nitro, $(C_1-C_6)$alkyl, halo$(C_1-C_6)$alkyl, —O$(C_1-C_6)$alkyl, $(C_3-C_{10})$cycloalkyl, $(C_6-C_{10})$aryl, heterocycloalkyl, and heteroaryl;

the cycloalkyl is a 3- to 10-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino, and cyano;

the heteroaryl is a 5- to 12-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino, and cyano;

the heterocycloalkyl is a 5- to 12-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino, and cyano;

the halogen is selected from chlorine, bromine, iodine, and fluorine; or a stereoisomer, a tautomer, or a pharmaceutically acceptable salt thereof.

17. A compound of Formula IB;

Formula IB (IB)

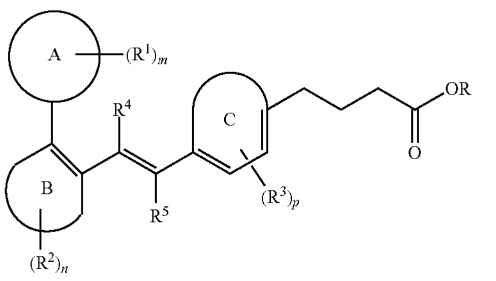

Ring A is selected from the group consisting of a 3- to 10-membered cycloalkyl, a 5- to 12-membered heterocycloalkyl, a $(C_6-C_{10})$aryl, and a 5- to 12-membered heteroaryl, wherein the heterocycloalkyl and the heteroaryl contain 1, 2, 3 or 4 heteroatoms independently selected from the group consisting of N, O and S;

Ring B and Ring C are independently selected from the group consisting of $(C_6-C_{10})$aryl, and a 5- to 12-membered heteroaryl containing 1, 2 or 3 heteroatoms independently selected from the group consisting of N, O and S;

R is hydrogen or a $(C_1-C_6)$alkyl;

$R^1$, $R^2$, and $R^3$ at each occurrence are independently selected from the group consisting of hydrogen, a halogen, a $(C_1-C_6)$alkyl, a halo$(C_1-C_6)$alkyl, a 3- to 10-membered cycloalkyl, and a 5- to 12-membered heterocycloalkyl;

$R^4$ is independently selected from hydrogen or a $(C_1-C_6)$alkyl;

$R^5$ is independently selected from hydrogen, a halogen or a $(C_1-C_6)$alkyl; and m, n and p are each an integer independently selected from 1, 2 and 3;

wherein, the $(C_1-C_6)$alkyl is unsubstituted or substituted with one or more groups independently selected from the group consisting of halogen, hydroxy, cyano, nitro, $(C_1-C_6)$alkyl, halo$(C_1-C_6)$alkyl, —O$(C_1-C_6)$alkyl, $(C_3-C_{10})$cycloalkyl, $(C_6-C_{10})$aryl, heterocycloalkyl, and heteroaryl;

the cycloalkyl is a 3- to 10-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino, and cyano;

the heteroaryl is a 5- to 12-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino, and cyano;

the heterocycloalkyl is a 5- to 12-membered ring, which is unsubstituted or substituted with one or more groups independently selected from the group consisting of $(C_1-C_6)$alkyl, halogen, hydroxy, —O—$(C_1-C_6)$alkyl, $(C_3-C_{10})$cycloalkyl, $(C_6-C_{10})$aryl, heterocycloalkyl, heteroaryl, amino, and cyano;

the halogen is selected from chlorine, bromine, iodine, and fluorine; or a stereoisomer, a tautomer, or a pharmaceutically acceptable salt thereof.

18. A compound of Formula IC;

Formula IC (IC)

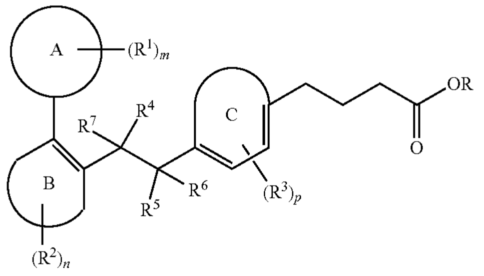

wherein,

Ring A is selected from the group consisting of a 3- to 10-membered cycloalkyl, a 5- to 12-membered heterocycloalkyl, a $(C_6-C_{10})$aryl, and a 5- to 12-membered heteroaryl, wherein the heterocycloalkyl and the heteroaryl contain 1, 2, 3 or 4 heteroatoms independently selected from the group consisting of N, O and S;

Ring B and Ring C are independently selected from the group consisting of a ($C_6$-$C_{10}$)aryl and a 5- to 12-membered heteroaryl containing 1, 2 or 3 heteroatoms independently selected from the group consisting of N, O and S;

R is hydrogen or a ($C_1$-$C_6$)alkyl;

$R^1$, $R^2$, and $R^3$ at each occurrence is independently selected from the group consisting of hydrogen, a halogen, a ($C_1$-$C_6$)alkyl, halo($C_1$-$C_6$)alkyl, a 3- to 10-membered cycloalkyl, and a 5- to 12-membered heterocycloalkyl;

$R^4$ and $R^7$ are independently selected from hydrogen or a ($C_1$-$C_6$)alkyl;

$R^5$ and $R^6$ are independently selected from the group consisting of hydrogen, a halogen and a ($C_1$-$C_6$)alkyl; and m, n and p are each an integer independently selected from 1, 2 or 3;

wherein, the ($C_1$-$C_6$)alkyl is unsubstituted or substituted with one or more groups independently selected from the group consisting of halogen, hydroxy, cyano, nitro, ($C_1$-$C_6$) alkyl, halo($C_1$-$C_6$)alkyl, —O($C_1$-$C_6$)alkyl, ($C_3$-$C_{10}$)cycloalkyl, ($C_6$-$C_{10}$)aryl, heterocyclyl, and heteroaryl;

the cycloalkyl is a 3- to 10-membered ring, which is unsubstituted or substituted with one or more groups independently selected from the group consisting of ($C_1$-$C_6$)alkyl, halogen, hydroxy, —O—($C_1$-$C_6$)alkyl, ($C_3$-$C_{10}$)cycloalkyl, ($C_6$-$C_{10}$)aryl, heterocyclyl, heteroaryl, amino, and cyano;

the heteroaryl is a 5- to 12-membered ring, which is unsubstituted or substituted with one or more groups independently selected from the group consisting of ($C_1$-$C_6$)alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino, and cyano;

the heterocycloalkyl is a 5- to 12-membered ring, which is unsubstituted or substituted with one or more groups independently selected from the group consisting of ($C_1$-$C_6$)alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino, and cyano;

the halogen is selected from chlorine, bromine, iodine, and fluorine; or a stereoisomer, a tautomer, a pharmaceutically acceptable salt thereof.

19. A compound of Formula ID;

Formula ID (ID)

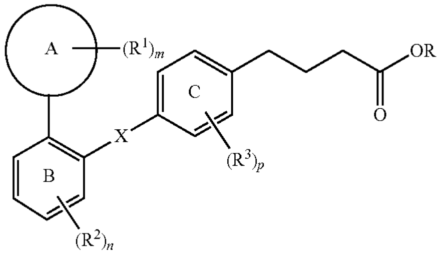

wherein,

Ring A is selected from the group consisting of a 3- to 10-membered cycloalkyl, 5- to 12-membered heterocycloalkyl, a ($C_6$-$C_{10}$)aryl, and a 5- to 12-membered heteroaryl, wherein the heterocycloalkyl and the heteroaryl contain 1, 2, 3 or 4 heteroatoms independently selected from the group consisting of N, O and S;

Ring B and Ring C are independently selected from a ($C_6$-$C_{10}$)aryl or a 5- to 12-membered heteroaryl containing 1, 2 or 3 heteroatoms independently selected from the group consisting of N, O and S;

X is selected from

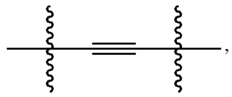, 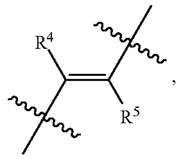, and

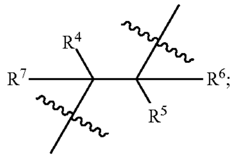

wherein  represents a point of attachment;

R is hydrogen or a ($C_1$-$C_6$)alkyl;

$R^1$, $R^2$, and $R^3$ at each occurrence are independently selected from the group consisting of hydrogen, a halogen, a ($C_1$-$C_6$)alkyl, a halo($C_1$-$C_6$)alkyl, a 3- to 10-membered cycloalkyl, and a 5- to 12-membered heterocycloalkyl;

$R^4$ and $R^7$ are independently selected from the group consisting of hydrogen and a ($C_1$-$C_6$)alkyl;

$R^5$ and $R^6$ are independently selected from the group consisting of hydrogen, a halogen, and a ($C_1$-$C_6$)alkyl; and m, n and p are each integer independently selected from 1, 2 and 3;

wherein, the ($C_1$-$C_6$)alkyl is unsubstituted or substituted with one or more groups independently selected from the group consisting of halogen, hydroxy, cyano, nitro, ($C_1$-$C_6$) alkyl, halo($C_1$-$C_6$)alkyl, —O($C_1$-$C_6$)alkyl, ($C_3$-$C_8$)cycloalkyl, ($C_6$-$C_{10}$)aryl, heterocycloalkyl, and heteroaryl;

the cycloalkyl is a 3- to 10-membered ring, which is unsubstituted or substituted with one or more groups independently selected from the group consisting of ($C_1$-$C_6$)alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino, and cyano;

the heteroaryl is a 5- to 12-membered ring, which is unsubstituted or substituted with one or more groups independently selected from the group consisting of ($C_1$-$C_6$)alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino, and cyano;

the heterocycloalkyl is a 5- to 12-membered ring, which is unsubstituted or substituted with one or more groups independently selected from the group consisting of ($C_1$-$C_6$)alkyl, halogen, hydroxy, —O—($C_1$-$C_6$)alkyl, ($C_3$-$C_{10}$)cycloalkyl, ($C_6$-$C_{10}$)aryl, heterocycloalkyl, heteroaryl, amino, and cyano;

the halogen is selected from chlorine, bromine, iodine, and fluorine; or a stereoisomer, a tautomer, a pharmaceutically acceptable salt thereof.

20. The compound according to claim 1, wherein the compound is selected from:

4-(5-((5-Fluoro-2-(6-methoxypyridin-3-yl)phenyl)ethynyl)pyridin-2-yl)butanoic acid;

4-(5-(5-Fluoro-2-(6-methoxypyridin-3-yl)phenethyl) pyridin-2-yl)butanoic acid;

4-(5-((5-Fluoro-2-(5-methylthiophen-2-yl)phenyl)ethynyl)pyridin-2-yl)butanoic acid;

4-(5-(5-Fluoro-2-(5-methylthiophen-2-yl)phenethyl)pyridin-2-yl)butanoic acid;

4-(4-(1,1-Difluoro-2-(5-fluoro-2-(5-methylthiophen-2-yl)phenyl)ethyl)phenyl)butanoic acid;

4-(4-(1,1-Difluoro-2-(5-fluoro-2-(5-(1-methylcyclopropyl)thiophen-2-yl)phenyl)ethyl)-phenyl)butanoic acid;

4-(4-(1,1-Difluoro-2-(4-fluoro-4'-methyl-[1,1'-biphenyl]-2-yl)ethyl)phenyl)butanoic acid, 4-(4-(2-(2-(5-Cyclopropylthiophen-2-yl)-5-fluorophenyl)-1,1-difluoroethyl)phenyl)-butanoic acid;

4-(4-(2-(2-(2,3-Dihydrobenzofuran-5-yl)-5-fluorophenyl)-1,1-difluoroethyl)phenyl)-butanoic acid;

4-(4-(2-(4'-Cyclopropyl-4-fluoro-[1,1'-biphenyl]-2-yl)-1,1-difluoroethyl)phenyl)butanoic acid;

4-(4-((2-(5-(1-Cyanocyclopropyl)thiophen-2-yl)-5-fluorophenyl)ethynyl)phenyl)-butanoic acid;

4-(4-(5-fluoro-2-(4,5,6,7-tetrahydrobenzo[d]thiazol-2-yl) phenethyl)phenyl)butanoic acid;

4-(4-(2-(5-cyclopropylthiophen-2-yl)-5-fluorophenethyl) phenyl)butanoic acid;

4-(4-(5-fluoro-2-(5-(1-methylcyclopropyl)thiophen-2-yl) styryl)phenyl)butanoic acid;

4-(4-(2-(5-(1-cyanocyclopropyl)thiophen-2-yl)-5-fluorostyryl)phenyl)butanoic acid;

4-(4-(5-fluoro-2-(4,5,6,7-tetrahydrobenzo[b]thiophen-2-yl)styryl)phenyl)butanoic acid;

4-(4-(5-fluoro-2-(4,5,6,7-tetrahydrobenzo[d]thiazol-2-yl) styryl)phenyl)butanoic acid;

4-(4-((2-(5-cyclopropylthiophen-2-yl)-5-fluorophenyl) ethynyl)phenyl)butanoic acid;

4-(4-((5-fluoro-2-(4,5,6,7-tetrahydrobenzo[d]thiazol-2-yl)phenyl)ethynyl)phenyl)-butanoic acid;

4-(4-(1,1-difluoro-2-(5-fluoro-2-(6-methoxypyridin-3-yl) phenyl)ethyl)phenyl)butanoic acid;

4-(4-(1,1-difluoro-2-(5-fluoro-2-(5,6,7,8-tetrahydronaphthalen-2-yl)phenyl)ethyl)phenyl)butanoic acid;

4-(4-(2-(2-(bicyclo[4.2.0]octa-1(6),2,4-trien-3-yl)-5-fluorophenyl)-1,1-difluoroethyl)phenyl)butanoic acid; and a stereoisomer, a tautomer, a pharmaceutically acceptable salt thereof.

21. A pharmaceutical composition comprising a therapeutically effective amount of the compound according to claim 1, or a stereoisomer, a tautomer, a pharmaceutically acceptable salt thereof; and at least one pharmaceutically acceptable carrier or excipient.

22. A method of inhibiting GPR120 comprising administering to a subject in need thereof, a therapeutically effective amount of the compound according to claim 1, or a stereoisomer, a tautomer, or a pharmaceutically acceptable salt thereof.

23. A compound according to claim 1 or a stereoisomer, a tautomer, or a pharmaceutically acceptable salt thereof; for use in the treatment or prophylaxis of a disease or a disorder mediated by GPR120.

* * * * *